United States Patent
Pfister et al.

(10) Patent No.: US 9,978,950 B2
(45) Date of Patent: May 22, 2018

(54) MATERIALS FOR ELECTRONIC DEVICES

(71) Applicant: Merck Patent GmbH, Darmstadt (DE)

(72) Inventors: Jochen Pfister, Alsbach-Haehnlein (DE); Frank Voges, Bad Duerkheim (DE); Elvira Montenegro, Weinheim (DE); Teresa Mujica-Fernaud, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 83 days.

(21) Appl. No.: 14/911,359

(22) PCT Filed: Jul. 24, 2014

(86) PCT No.: PCT/EP2014/002031
§ 371 (c)(1),
(2) Date: Feb. 10, 2016

(87) PCT Pub. No.: WO2015/022051
PCT Pub. Date: Feb. 19, 2015

(65) Prior Publication Data
US 2016/0190466 A1    Jun. 30, 2016

(30) Foreign Application Priority Data

Aug. 15, 2013 (EP) .................................... 13004061

(51) Int. Cl.
| | |
|---|---|
| *H01L 51/50* | (2006.01) |
| *H01L 51/00* | (2006.01) |
| *H05B 33/20* | (2006.01) |
| *C07D 307/94* | (2006.01) |
| *C07D 405/04* | (2006.01) |

(52) U.S. Cl.
CPC ........ *H01L 51/0061* (2013.01); *C07D 307/94* (2013.01); *C07D 405/04* (2013.01); *H01L 51/006* (2013.01); *H01L 51/0056* (2013.01); *H01L 51/0058* (2013.01); *H01L 51/0059* (2013.01); *H01L 51/0072* (2013.01); *H01L 51/0073* (2013.01); *H01L 51/5056* (2013.01); *H05B 33/20* (2013.01); *H01L 51/0052* (2013.01); *H01L 51/0085* (2013.01); *H01L 51/5088* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 8,334,058 | B2 | 12/2012 | Heil et al. |
| 8,852,756 | B2 | 10/2014 | Vestweber et al. |
| 9,461,249 | B2 | 10/2016 | Vestweber et al. |
| 2014/0332787 | A1 | 11/2014 | Hong et al. |

FOREIGN PATENT DOCUMENTS

| | | | | |
|---|---|---|---|---|
| TW | 200706636 | A | 2/2007 | |
| WO | WO-2006108497 | A1 | 10/2006 | |
| WO | WO-2006122630 | A1 | 11/2006 | |
| WO | WO 2013/100467 | * | 7/2013 | ............. C09K 11/06 |
| WO | WO-2013100467 | A1 | 7/2013 | |
| WO | WO-2014129846 | A1 | 8/2014 | |

OTHER PUBLICATIONS

International Search Report for PCT/EP2014/002031 dated Oct. 24, 2014.
U.S. Appl. No. 15/638,783, filed Jun. 30, 2017.
Taiwanese Office Action with English Translation for Taiwanese Application No. 103127619, dated Feb. 12, 2018.

* cited by examiner

*Primary Examiner* — Gregory D Clark
(74) *Attorney, Agent, or Firm* — Drinker Biddle & Reath LLP

(57) ABSTRACT

The present application relates to a compound of a formula (I) which contains a spirobifluorene basic structure condensed onto a benzofuran unit. The application furthermore relates to a process for the preparation of the compound of the formula (I), and to the use of the compound of the formula (I) in an electronic device.

17 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2014/002031, filed Jul. 24, 2014, which claims benefit of European Application No. 13004060.1, filed Aug. 15, 2013, both of which are incorporated herein by reference in their entirety.

The present application relates to a compound having a spirobifluorene basic structure and a benzofluorene unit condensed onto the latter. The compound is suitable for use in electronic devices, in particular in organic electroluminescent devices (OLEDs).

Electronic devices in the sense of this application are taken to mean so-called organic electronic devices which comprise organic semiconductor materials as functional materials. In particular, they are taken to mean OLEDs.

The structure of OLEDs in which organic compounds are employed as functional materials is described, for example, in U.S. Pat. No. 4,539,507, U.S. Pat. No. 5,151,629, EP 0676461 and WO 98/27136. In general, the term OLEDs is taken to mean electronic devices which contain one or more layers comprising organic compounds and emit light on application of an electrical voltage.

In the case of electronic devices, in particular OLEDs, there is considerable interest in an improvement in the performance data, in particular lifetime, efficiency and operating voltage. An entirely satisfactory solution has still not been found in these aspects.

The performance data of electronic devices are influenced to a great extent by layers having a hole-transporting function, such as, for example, hole-injecting layers, hole-transport layers, electron-blocking layers and also emitting layers. Novel materials having hole-transporting properties are continuously being sought for use in these layers.

It is known from the prior art to employ triarylamines as materials having hole-transporting properties in the above-mentioned layers. These can be monotriarylamines, as described, for example, in JP 1995/053955, WO 2006/123667 and JP 2010/222268, or bis- or other oligoamines, as described, for example, in U.S. Pat. No. 7,504,163 or US 2005/0184657. Known examples of triarylamine compounds as materials having hole-transporting properties for OLEDs are, inter alia, tris-p-biphenylamine, N,N'-di-1-naphthyl-N,N'-diphenyl-1,1'-biphenyl-4,4'-diamine (NPB) and 4,4',4"-tris-(3-methylphenylphenylamino)triphenylamine (MTDATA).

The prior art furthermore discloses the use of spirobifluorene-arylamino compounds in OLEDs, inter alia as hole-transport materials (WO 2012/034627 and WO 2013/120577).

Also known for this use are spirobifluorene derivatives which contain a benzofuran unit condensed onto the spirobifluorene basic structure and which contain one or more arylamino groups bonded to the spirobifluorene in the 2-position (WO 2013/100467).

In the course of investigations of novel materials for use in OLEDs, it has now been found, surprisingly, that compounds which contain a benzofuran unit condensed onto a spirobifluorene basic structure and which contain an arylamine or carbazole group bonded to the spirobifluorene in a certain position are highly suitable for use in OLEDs, in particular as materials having a hole-transporting function.

The compounds found have one or more properties selected from very good hole-conducting properties, very good electron-blocking properties, a high glass-transition temperature, high oxidation stability, good solubility and high temperature stability.

The present invention therefore relates to a compound of the formula (I)

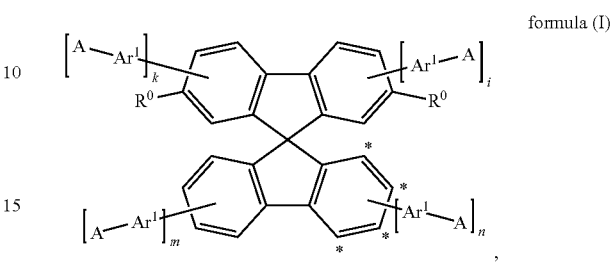

formula (I)

which contains a group of the formula (B)

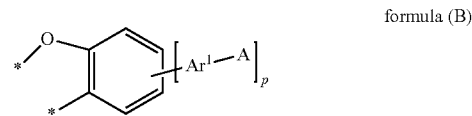

formula (B)

bonded to the basic structure of the formula (I) at two adjacent positions marked by *, where the condensation is such that a bond marked by * in formula (B) in each case links to a position marked by * on the basic structure of the formula (I);
  which may be substituted by a radical $R^1$ at one or more positions on the basic structure of the formula (I) and the group of the formula (B) which are depicted as unsubstituted; and
  which has the following definitions of the variables:
A is on each occurrence, identically or differently, a group of the formula (A1), (A2) or (A3), which is bonded via the bond marked by #;

formula (A1)

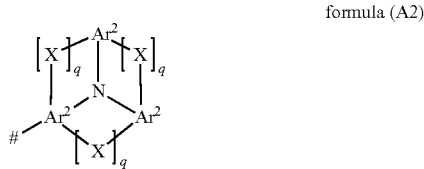

formula (A2)

formula (A3)

$Ar^1$ is on each occurrence, identically or differently, a single bond or an aromatic or heteroaromatic ring system having 6 to 30 aromatic ring atoms, which may be substituted by one or more radicals $R^2$;
$Ar^2$ is on each occurrence, identically or differently, an aromatic or heteroaromatic ring system having 6 to 30 aromatic ring atoms, which may be substituted by one or more radicals $R^2$;

X is on each occurrence, identically or differently, a single bond or a group selected from $BR^2$, $C(R^2)_2$, $Si(R^2)_2$, C=O, O, S, S=O, $SO_2$, $NR^2$, $PR^2$ or $P(=O)R^2$;

$R^0$ is on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by —$R^3C$=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$, or an aromatic or heteroaromatic aromatic ring system having 5 to 30 aromatic ring atoms, which may be substituted by one or more radicals $R^3$;

$R^1$, $R^2$ are on each occurrence, identically or differently, H, D, F, C(=O)$R^3$, CN, $Si(R^3)_3$, $N(Ar^3)_2$, $N(R^3)_2$, P(=O)($R^3)_2$, $OR^3$, S(=O)$R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by —$R^3C$=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$, or an aromatic or heteroaromatic ring system having 5 to 30 aromatic ring atoms, which may be substituted by one or more radicals $R^3$; two or more radicals $R^1$ or $R^2$ may be linked to one another and may form a ring;

$Ar^3$ is on each occurrence, identically or differently, an aromatic or heteroaromatic ring system having 5 to 30 aromatic ring atoms, which may be substituted by one or more radicals $R^3$;

$R^3$ is on each occurrence, identically or differently, H, D, F, C(=O)$R^4$, CN, $Si(R^4)_3$, $N(Ar^3)_2$, $N(R^4)_2$, P(=O)($R^4)_2$, $OR^4$, S(=O)$R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by —$R^4C$=$CR^4$—, —C≡C—, $Si(R^4)_2$, C=O, C=$NR^4$, —C(=O)O—, —C(=O)$NR^4$—, $NR^4$, P(=O)($R^4$), —O—, —S—, SO or $SO_2$, or an aromatic or heteroaromatic ring system having 5 to 30 aromatic ring atoms, which may be substituted by one or more radicals $R^4$; two or more radicals $R^3$ may be linked to one another and may form a ring;

$R^4$ is on each occurrence, identically or differently, H, D, F, CN or an aliphatic, aromatic or heteroaromatic organic radical having 1 to 20 C atoms, in which, in addition, one or more H atoms may be replaced by D, F or CN; two or more substituents $R^4$ may be linked to one another and may form a ring;

q is on each occurrence, identically or differently, 0 or 1, where at least one q in formula (A2) is equal to 1;

i, k, m, n and p are on each occurrence, identically or differently, 0 or 1, where at least one of these indices is equal to 1.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a single bond or by a non-aromatic unit, such as, for example, one or more optionally substituted C, Si, N, O or S atoms. The non-aromatic unit here preferably contains less than 10% of the atoms other than H, based on the total number of atoms other than H in the system. Thus, for example, systems such as 9,9'-spirobifluorene, 9,9'-diarylfluorene, triarylamine, diaryl ether and stilbene are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from the groups mentioned above under aryl and heteroaryl groups and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. Furthermore, however, the above-mentioned formulation is also intended to be taken to mean that, in the case where one of the two radicals represents hydrogen, the second radical is bonded at the position to which the hydrogen atom was bonded, with formation of a ring.

A is preferably a group of the formula (A-1) or (A-3), particularly preferably a group of the formula (A-1).

$Ar^1$ is preferably selected on each occurrence, identically or differently, from a single bond or a divalent group selected from benzene, biphenyl, terphenyl, fluorene, spirobifluorene, indenofluorene, carbazole, dibenzofuran, dibenzothiophene, each of which is optionally substituted by radicals $R^2$, or a combination of two or more of these groups, but where not more than 30 aromatic ring atoms may be present in $Ar^1$.

Groups $Ar^1$ are preferably selected from groups of the following formulae:

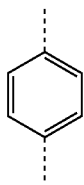

$Ar^1$-1

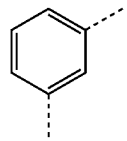

$Ar^1$-2

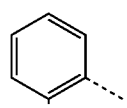

$Ar^1$-3

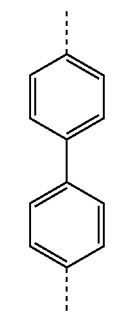

$Ar^1$-4

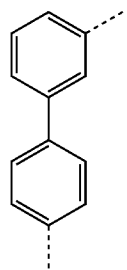

$Ar^1$-5

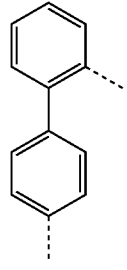

$Ar^1$-6

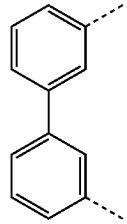

$Ar^1$-7

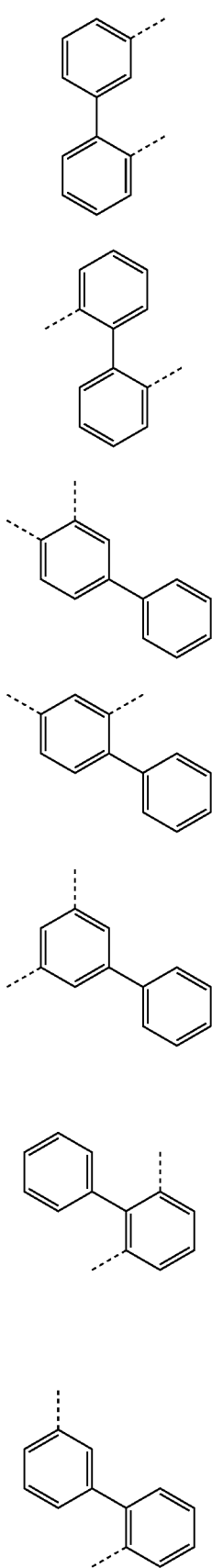
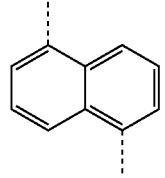
Ar¹-8
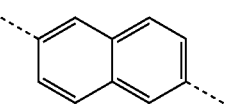
Ar¹-9
Ar¹-10
Ar¹-11
Ar¹-12
Ar¹-13
Ar¹-14
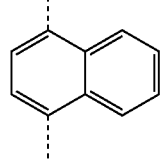
Ar¹-15
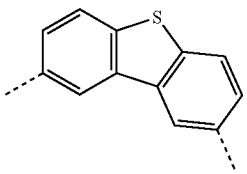
Ar¹-16
Ar¹-17
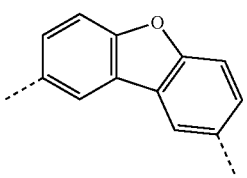
Ar¹-18
Ar¹-19
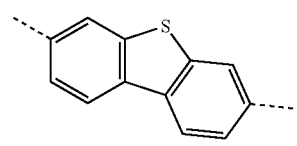
Ar¹-20
Ar¹-21
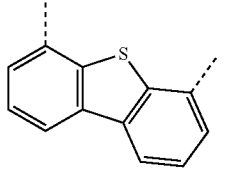
Ar¹-22
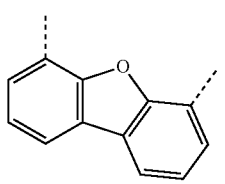
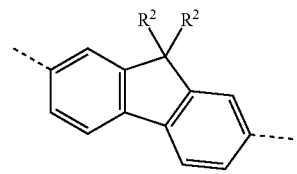
Ar¹-23

Ar¹-24 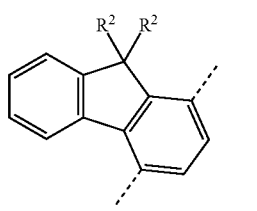

Ar¹-25 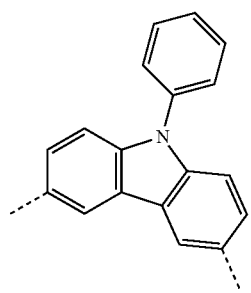

Ar¹-26 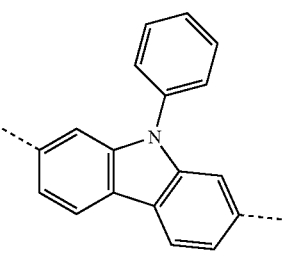

Ar¹-27 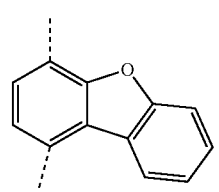

Arˢ-11

Ar¹-28 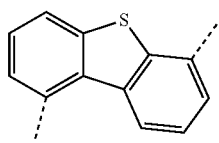

Ar¹-29 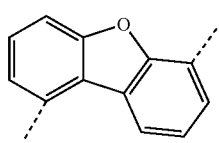

Ar¹-30 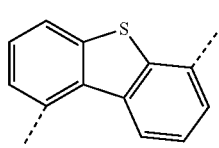

Ar¹-31 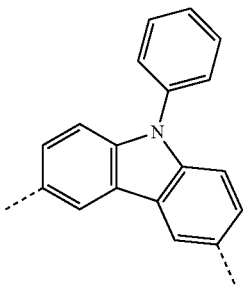

Ar¹-32 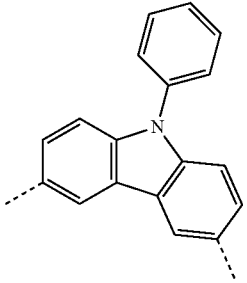

where the dashed bonds represent the bonds to the remaining parts of formula (I) and the groups may be substituted by one or more radicals R² at the free positions, but are preferably unsubstituted at the free positions.

R² in the groups of the formulae (Ar¹-23) and (Ar¹-24) preferably stands, identically or differently, for an alkyl group having 1 to 10 C atoms, in particular for methyl, or a phenyl group, which may be substituted by one or more radicals R³ and is preferably unsubstituted. Two alkyl groups R² here may also form a ring with formation of a spiro group, preferably a cyclohexyl ring or a cyclopentyl ring.

Ar² is preferably selected on each occurrence, identically or differently, from an aromatic or heteroaromatic ring system having 6 to 25 aromatic ring atoms, which may be substituted by one or more radicals R². Particular preference is given to phenyl, biphenyl, terphenyl, fluorenyl, spirobifluorenyl, indenofluorenyl, naphthyl, phenanthrenyl, furanyl, benzofuranyl, dibenzofuranyl, thiophenyl, benzothiophenyl, dibenzothiophenyl, carbazolyl, indolocarbazolyl and indenocarbazolyl, each of which may be substituted by one or more radicals R².

Groups Ar² are preferably selected, identically or differently on each occurrence, from groups of the following formulae:

Ar²-1 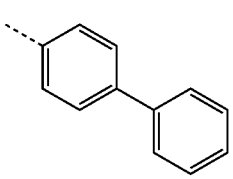

Ar²-2 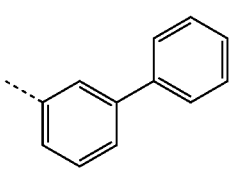

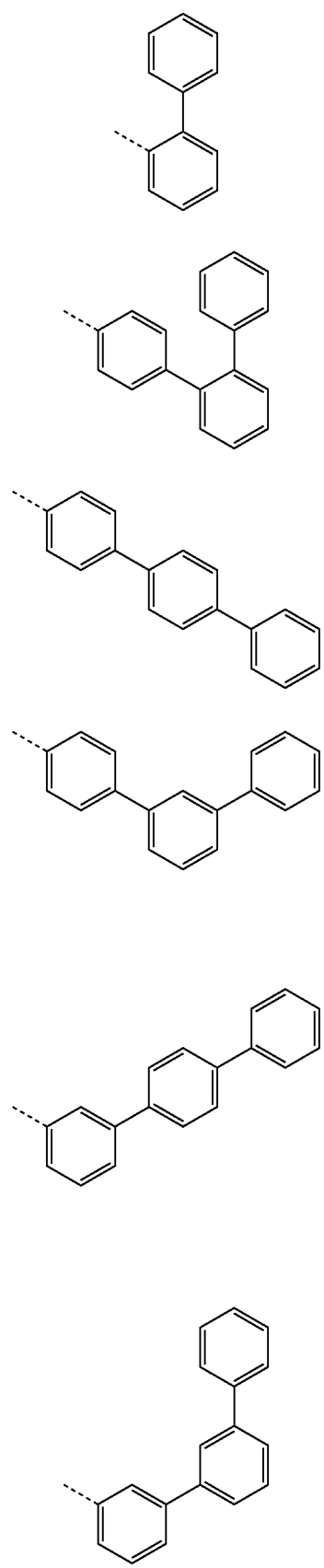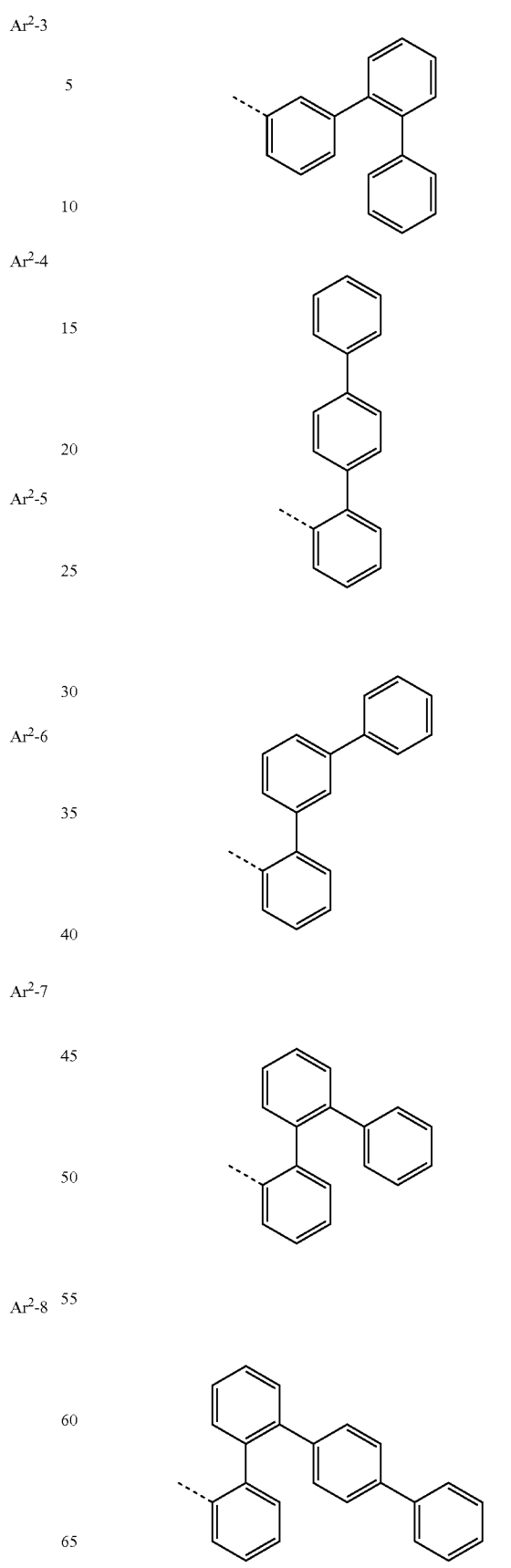

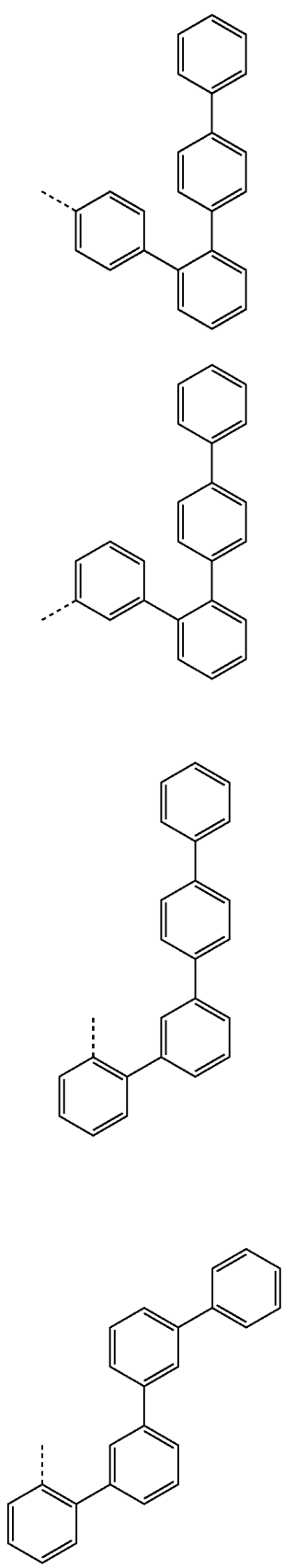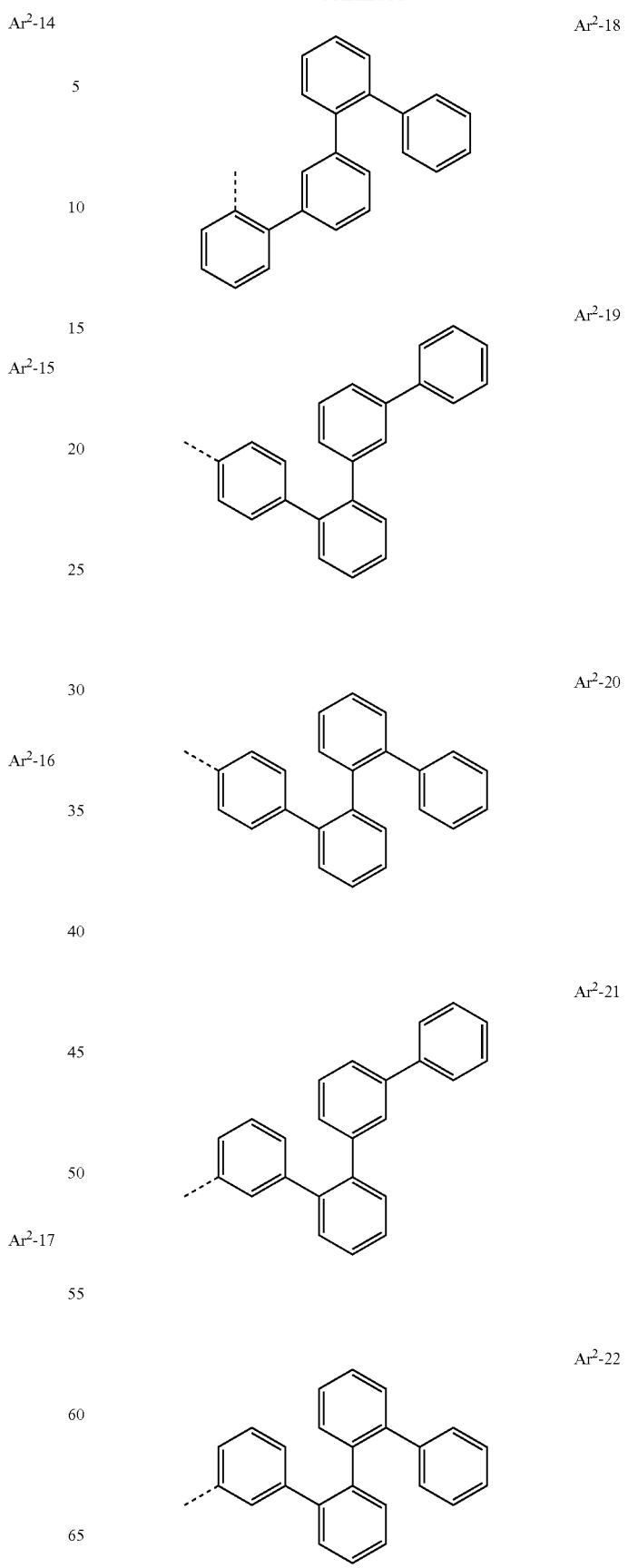

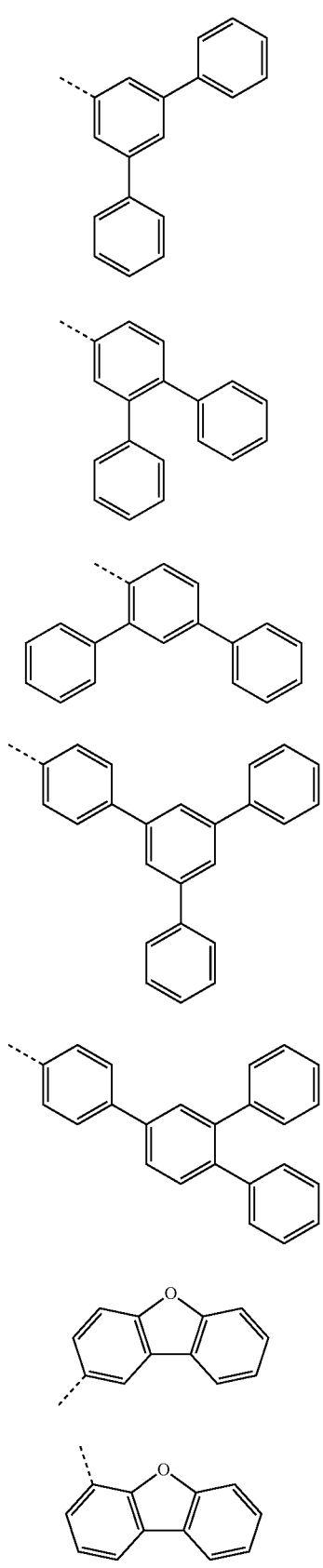
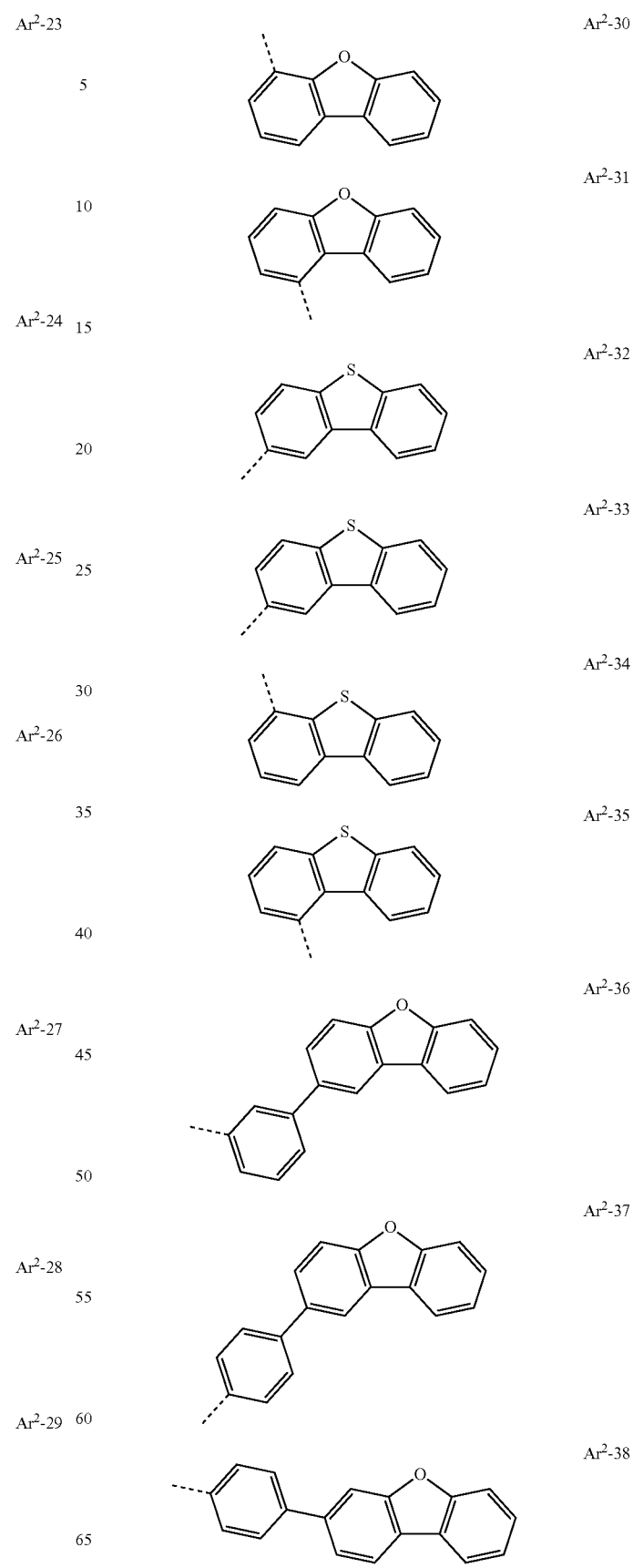

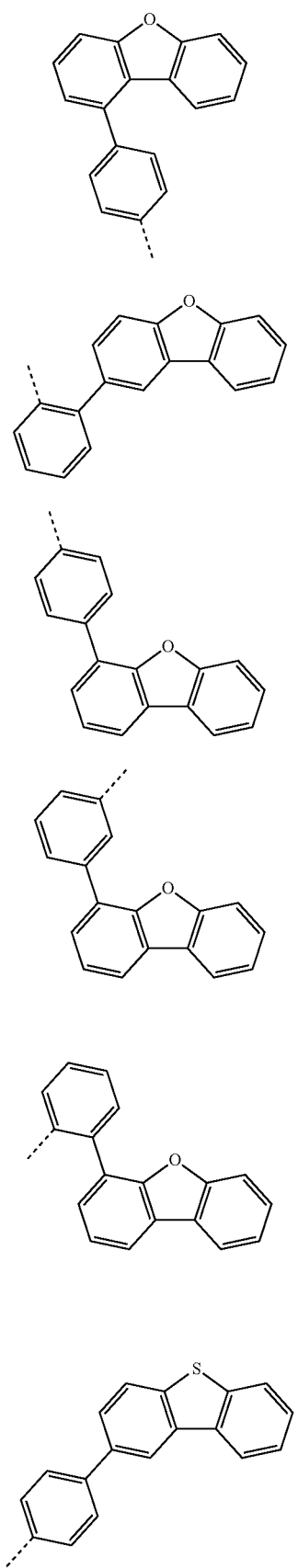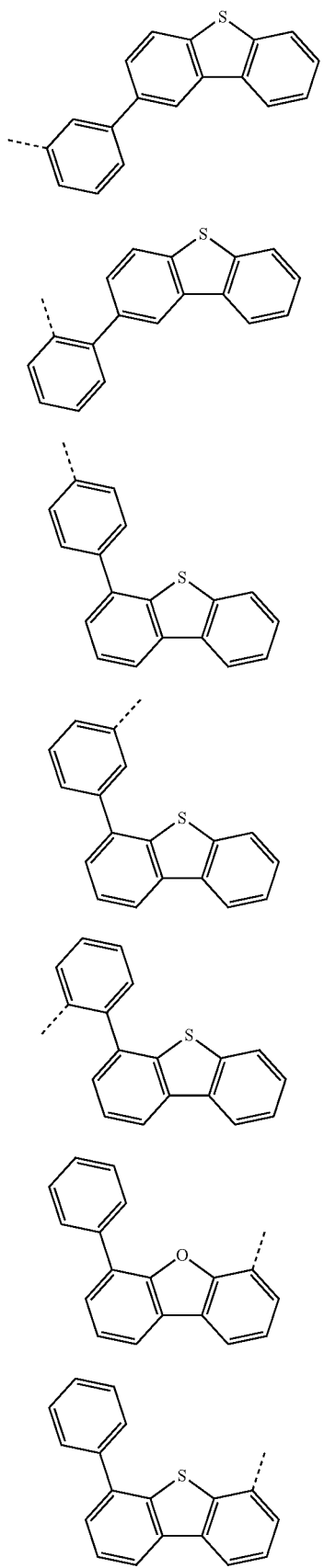

Ar²-52 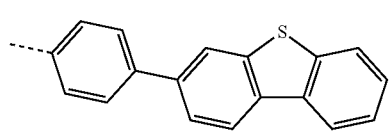
Ar²-53 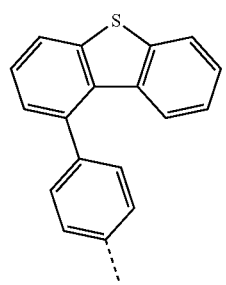
Ar²-54 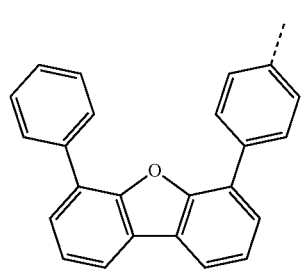
Ar²-55 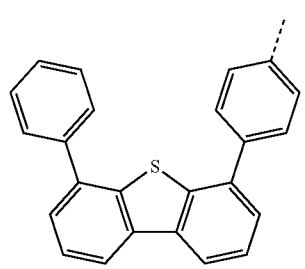
Ar²-56 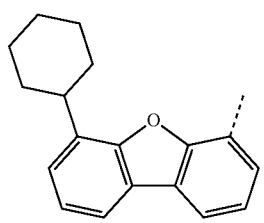
Ar²-57 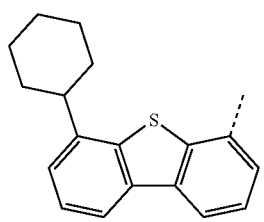
Ar²-58 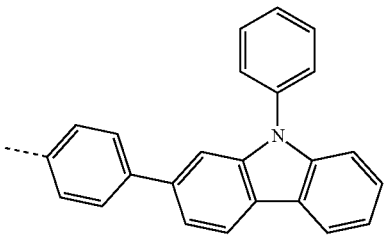
Ar²-59 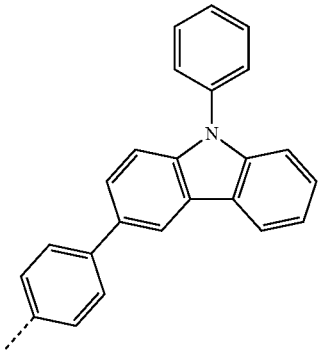
Ar²-60 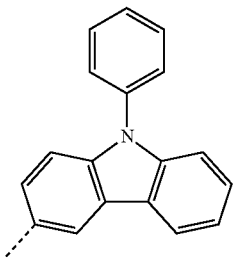
Ar²-61 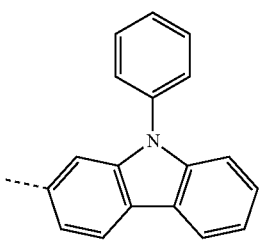
Ar²-62 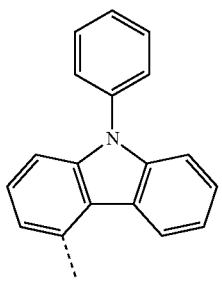

-continued
Ar²-63 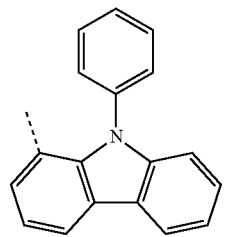
Ar²-64 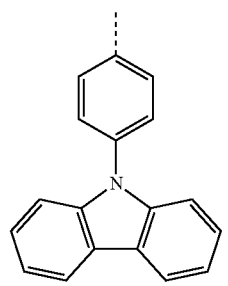
Ar²-65 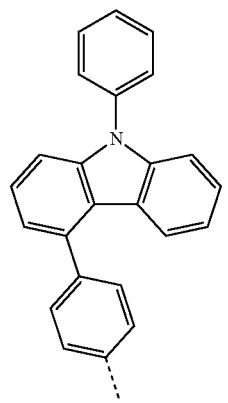
Ar²-66 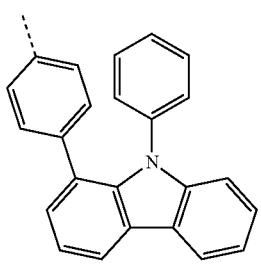
Ar²-67 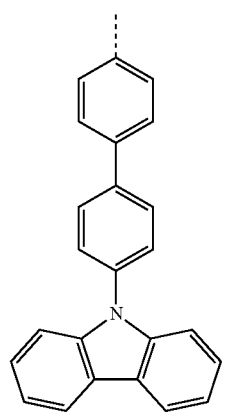
-continued
Ar²-68 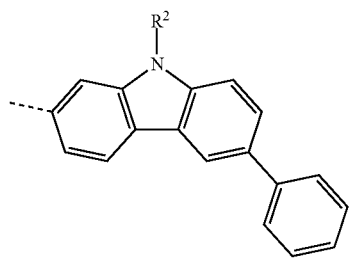
Ar²-69 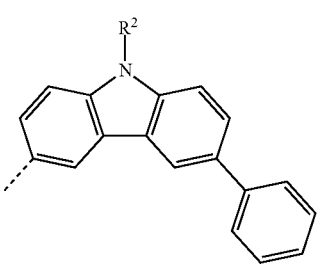
Ar²-70 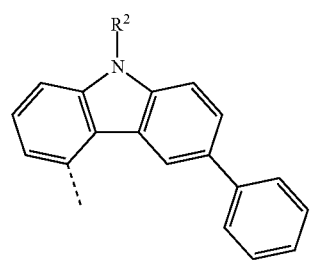
Ar²-71 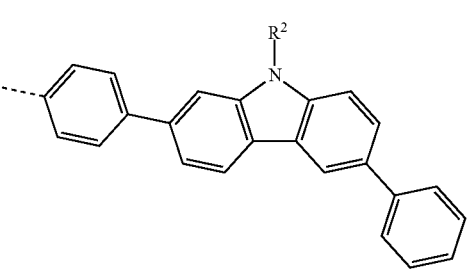
Ar²-72 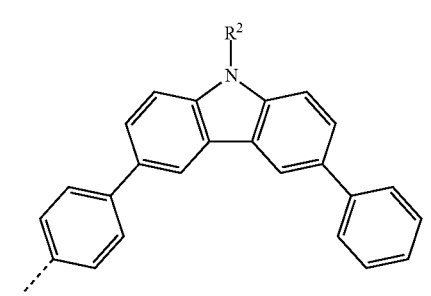

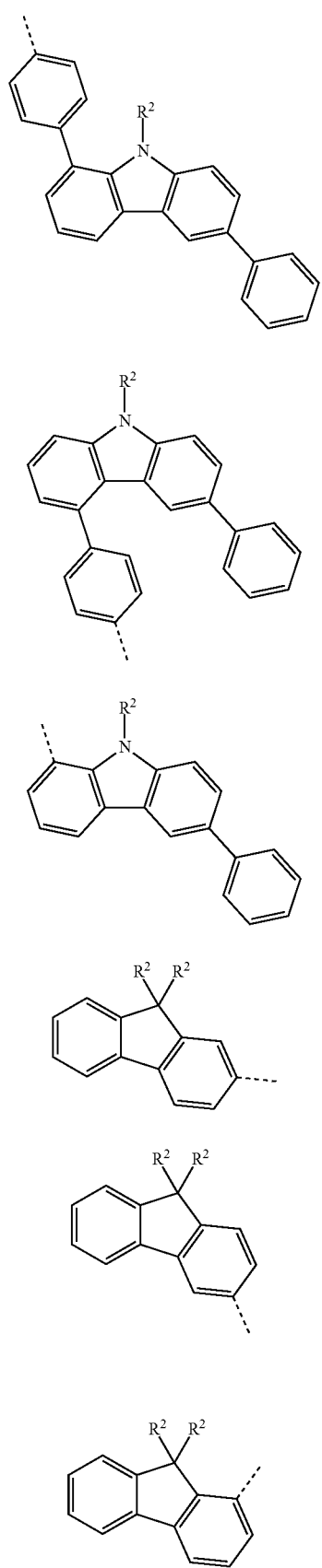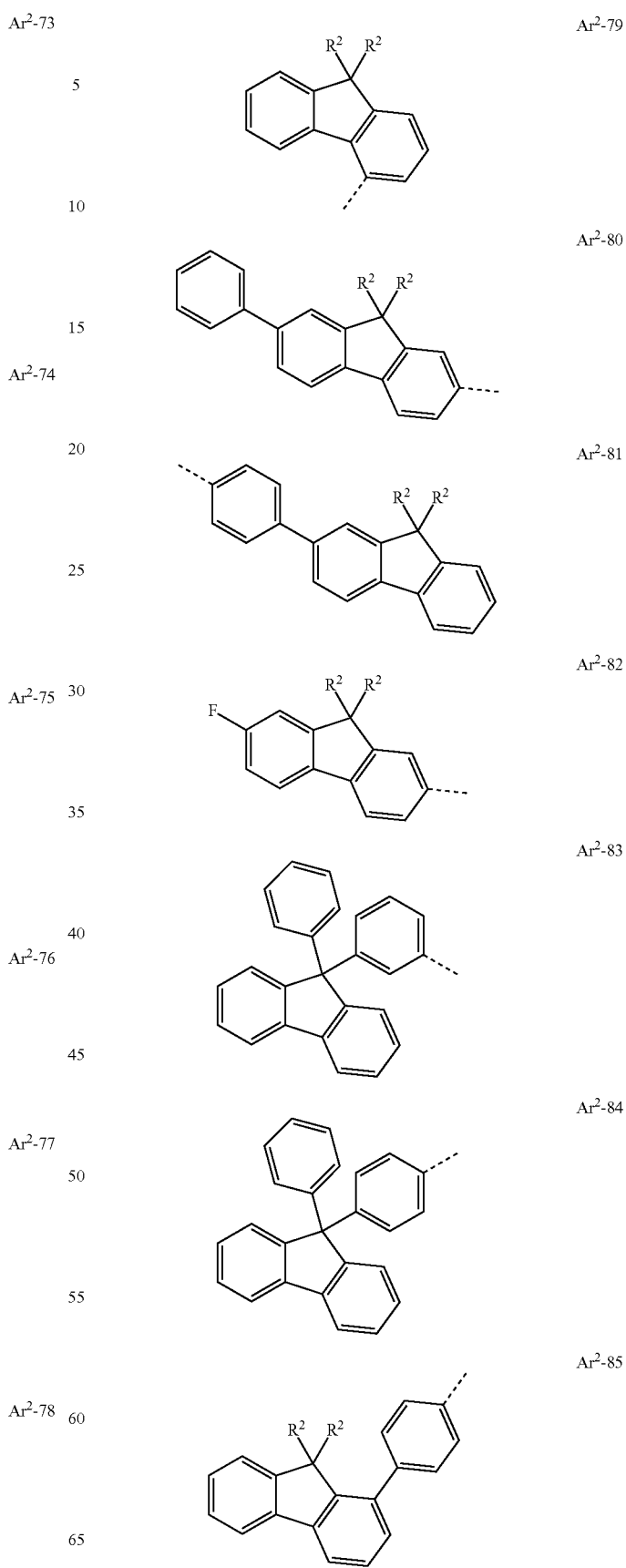

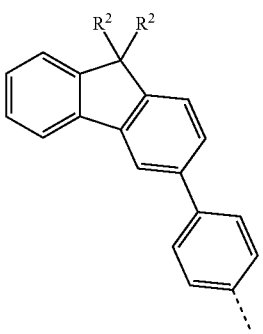 Ar²-86
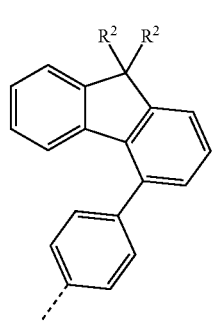 Ar²-87
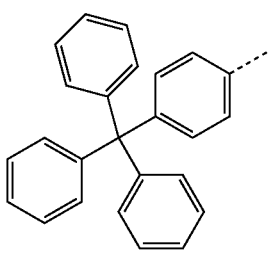 Ar²-88
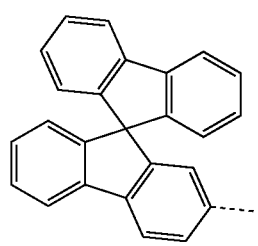 Ar²-89
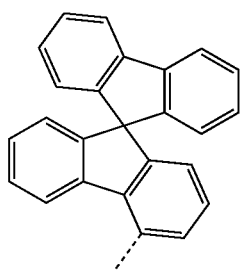 Ar²-90
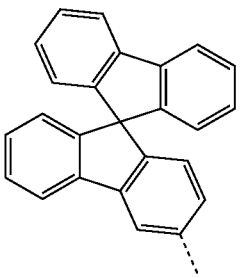 Ar²-91
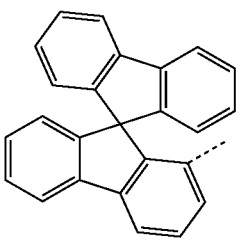 Ar²-92
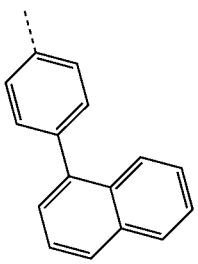 Ar²-93
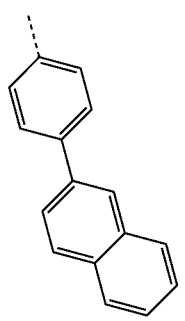 Ar²-94
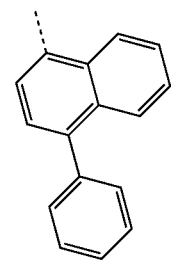 Ar²-95
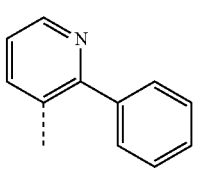 Ar²-96

-continued
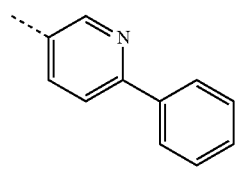
Ar²-97
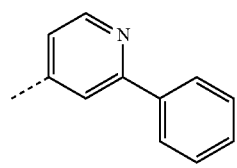
Ar²-98
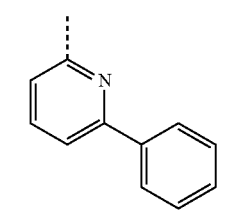
Ar²-99
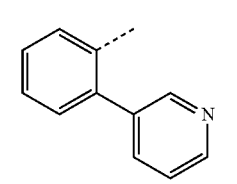
Ar²-100
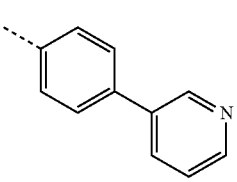
Ar²-101
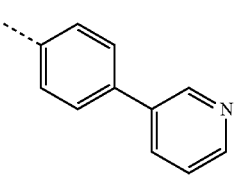
Ar²-102
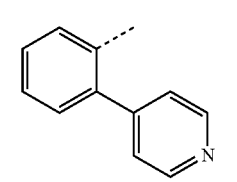
Ar²-103
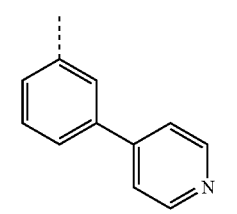
Ar²-104
-continued
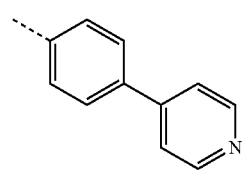
Ar²-105
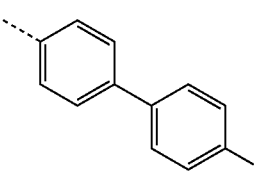
Ar²-106
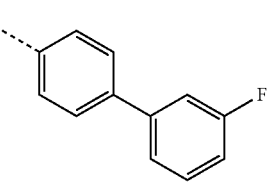
Ar²-107
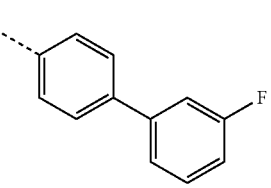
Ar²-108
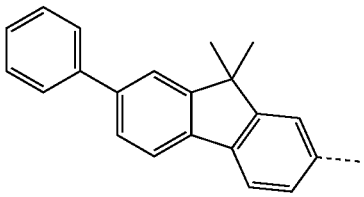
Ar²-109
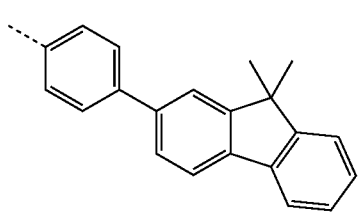
Ar²-110
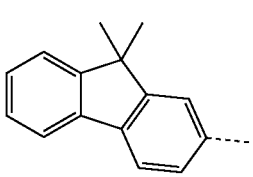
Ar²-111
Ar²-112

Ar²-113
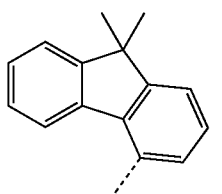

Ar²-114
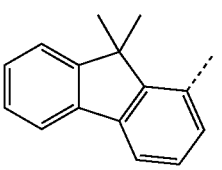

Ar²-115
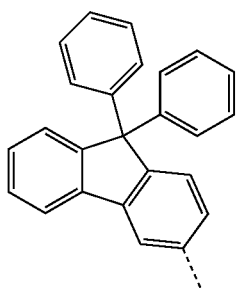

Ar²-116
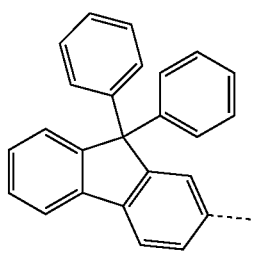

Ar²-117
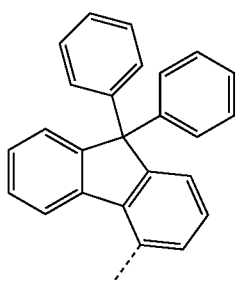

Ar²-118
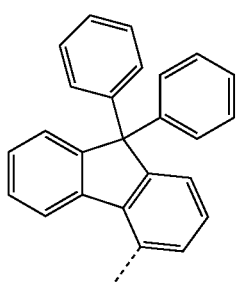

where the dashed bond represents the bond to the nitrogen and the groups may be substituted by one or more radicals R² at the free positions, but are preferably unsubstituted at the free positions.

R² in the groups of the formulae (Ar²-68) to (Ar²-82) and (Ar²-85) to (Ar²-87) preferably stands, identically or differently, for an alkyl group having 1 to 10 C atoms, in particular for methyl, or a phenyl group, which may be substituted by one or more radicals R³ and is preferably unsubstituted. Two alkyl groups R² here may also form a ring with formation of a spiro group, preferably a cyclohexyl ring or a cyclopentyl ring.

Preferred embodiments of the groups Ar³ correspond to those for groups Ar².

X is preferably selected on each occurrence, identically or differently, from a single bond or a group selected from $C(R^2)_2$, C=O, O, S and $NR^2$. X is particularly preferably a single bond.

R⁰ is preferably on each occurrence, identically or differently, H, D, F, a straight-chain alkyl or alkoxy group having 1 to 10 C atoms or a branched or cyclic alkyl or alkoxy group having 3 to 10 C atoms, where the above-mentioned groups may each be substituted by one or more radicals R³, or an aromatic or heteroaromatic ring system having 5 to 15 aromatic ring atoms. R⁰ is particularly preferably on each occurrence, identically or differently, H, F, a straight-chain alkyl group having 1 to 10 C atoms or a branched or cyclic alkyl group having 3 to 10 C atoms, where the above-mentioned groups may each be substituted by one or more radicals R³.

R¹ and R² are preferably on each occurrence, identically or differently, H, D, F, CN, $Si(R^3)_3$, $N(R^3)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals R³ and where one or more CH₂ groups in the above-mentioned groups may be replaced by —C≡C—, —R³C=CR³—, $Si(R^3)_2$, C=O, C=NR³, —NR³—, —O—, —S—, —C(=O)O— or —C(=O)NR³—, or an aromatic or heteroaromatic ring system having 5 to 30 aromatic ring atoms, which may in each case be substituted by one or more radicals R³, where two or more radicals R¹ or R² may be linked to one another and may form a ring. R¹ and R² are particularly preferably on each occurrence, identically or differently, H, D, F, CN, a straight-chain alkyl group having 1 to 10 C atoms or a branched or cyclic alkyl group having 3 to 10 C atoms, where the above-mentioned groups may each be substituted by one or more radicals R³, or an aromatic or heteroaromatic ring system having 6 to 25 aromatic ring atoms, which may in each case be substituted by one or more radicals R³.

R¹ is preferably on each occurrence, identically or differently, H, F, CN, a straight-chain alkyl group having 1 to 10 C atoms or a branched or cyclic alkyl group having 3 to 10 C atoms, where the above-mentioned groups may each be substituted by one or more radicals R³, or an aromatic or heteroaromatic ring system having 6 to 25 aromatic ring atoms, which may in each case be substituted by one or more radicals R³. Particularly preferred groups R¹ are H, F, CN, methyl, tert-butyl, phenyl, biphenyl, dibenzofuran, dibenzothiophene and carbazole.

If a radical R¹ bonded to the basic structure of the formula (I) does not represent H, it is preferably bonded in one of positions 4, 5, 4' and 5' of the spirobifluorene basic structure, where the numbering is as follows:

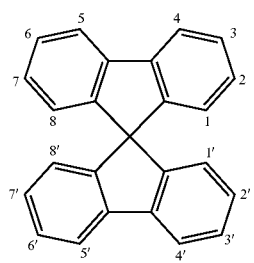

$R^3$ is preferably on each occurrence, identically or differently, H, D, F, CN, Si$(R^4)_3$, N$(Ar^3)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more CH$_2$ groups in the above-mentioned groups may be replaced by —C≡C—, —R$^4$C═CR$^4$—, Si$(R^4)_2$, C═O, C═NR$^4$, —NR$^4$—, —O—, —S—, —C(═O)O— or —C(═O)NR$^4$—, or an aromatic or heteroaromatic ring system having 5 to 30 aromatic ring atoms, which may in each case be substituted by one or more radicals $R^4$, where two or more radicals $R^3$ may be linked to one another and may form a ring. $R^3$ is particularly preferably on each occurrence, identically or differently, H, D, F, CN, N$(Ar^3)_2$, a straight-chain alkyl group having 1 to 10 C atoms or a branched or cyclic alkyl group having 3 to 10 C atoms, where the above-mentioned groups may each be substituted by one or more radicals $R^4$, or an aromatic or heteroaromatic ring system having 6 to 25 aromatic ring atoms, which may in each case be substituted by one or more radicals $R^4$.

p is preferably equal to 1.

k is preferably equal to 1.

n is preferably equal to 0.

Furthermore, the sum of the indices i, k, m, n and p is preferably equal to 1 or 2, particularly preferably equal to 1.

The sum of the indices p and m is preferably equal to 1.

These preferences relating to the indices i, k, m, n and p preferably occur in combination with one another.

A preferred embodiment of compounds of the formula (I) corresponds to the formula (I-A)

formula (I-A)

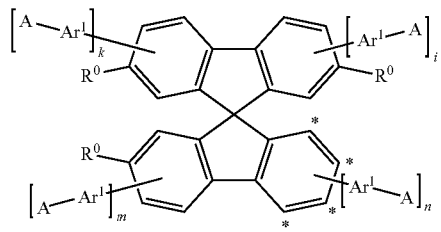

where the variables occurring are as defined for formula (I). The variables occurring preferably correspond to the embodiments indicated as preferred above.

A further preferred embodiment of compounds of the formula (I) corresponds to the formula (I-B)

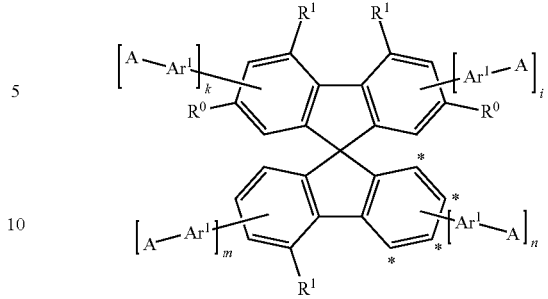

where the variables occurring are as defined for formula (I), with the exception that free positions are not substituted by radicals $R^1$. $R^1$ in formula (I-B) is preferably selected on each occurrence, identically or differently, from H, F, CN, straight-chain alkyl groups having 1 to 10 C atoms or branched or cyclic alkyl groups having 3 to 10 C atoms, where the above-mentioned groups may each be substituted by one or more radicals $R^3$, or aromatic or heteroaromatic ring systems having 6 to 25 aromatic ring atoms, which may in each case be substituted by one or more radicals $R^3$, particularly preferably from H, F, CN, methyl, tert-butyl, phenyl, biphenyl, dibenzofuran, dibenzothiophene and carbazole.

Furthermore, at least one radical $R^1$ in formula (I-B) is preferably selected from H, F, CN, straight-chain alkyl groups having 1 to 10 C atoms or branched or cyclic alkyl groups having 3 to 10 C atoms, where the above-mentioned groups may each be substituted by one or more radicals $R^3$, or aromatic or heteroaromatic ring systems having 6 to 25 aromatic ring atoms, which may in each case be substituted by one or more radicals $R^3$, particularly preferably from H, F, CN, methyl, tert-butyl, phenyl, biphenyl, dibenzofuran, dibenzothiophene and carbazole.

The preferred embodiments of the formulae (I-A) and (I-B) preferably occur in combination with one another.

$R^0$ here is particularly preferably on each occurrence, identically or differently, H, D, F, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$. $R^0$ here is especially preferably on each occurrence, identically or differently, H, F, a straight-chain alkyl group having 1 to 10 C atoms or a branched or cyclic alkyl group having 3 to 10 C atoms, where the above-mentioned groups may each be substituted by one or more radicals $R^3$.

Preferred embodiments of the compounds of the formula (I) correspond to the following formulae (I-1) to (I-18):

formula (I-1)

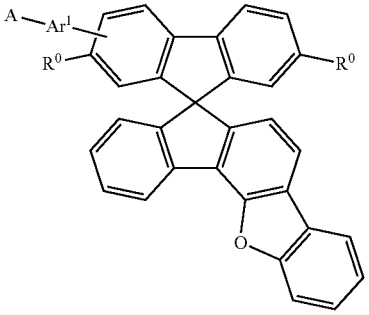

formula (I-2)
formula (I-3)
formula (I-4)
formula (I-5)
formula (I-6)
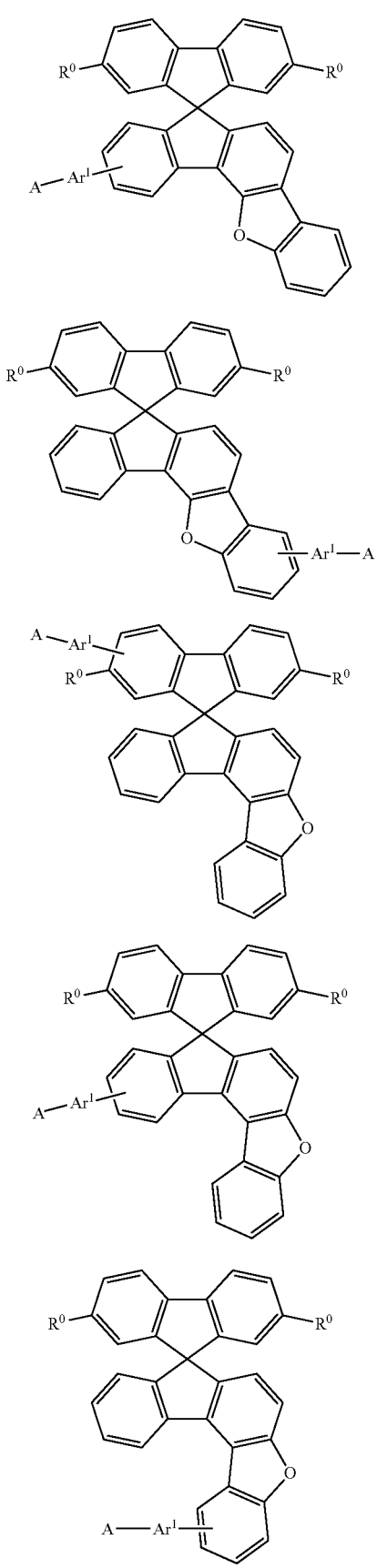
formula (I-7)
formula (I-8)
formula (I-9)
formula (I-10)
formula (I-11)
formula (I-12)
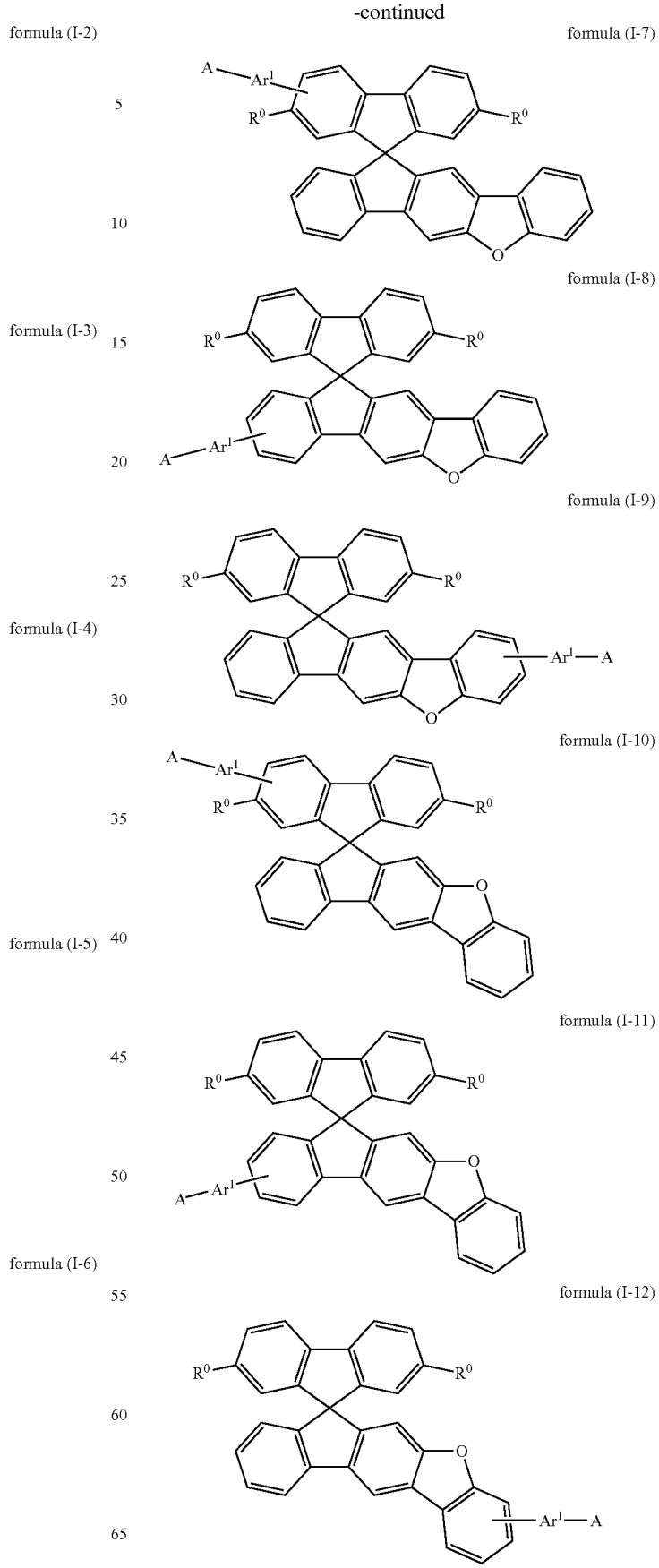

formula (I-13)

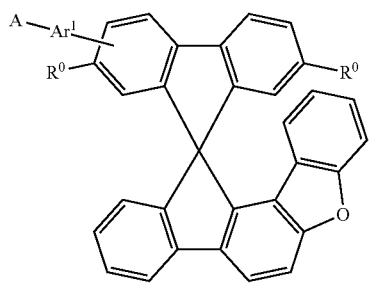

formula (I-14)

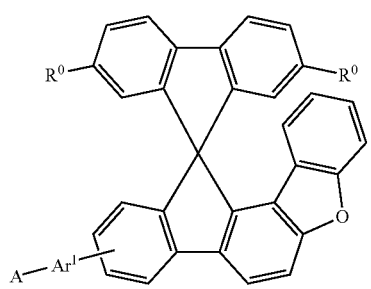

formula (I-15)

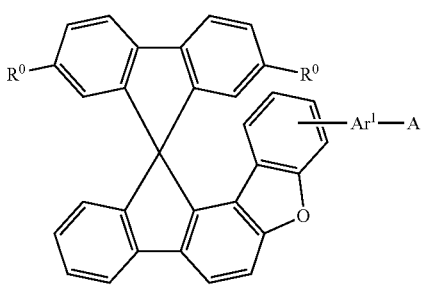

formula (I-16)

formula (I-17)

formula (I-18)

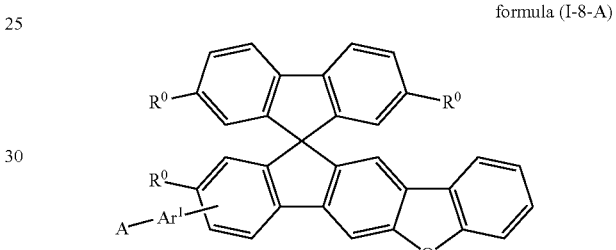

where the symbols occurring are as defined above.

The preferred embodiments of $R^0$, $Ar^1$ and A, in particular, apply to formulae (I-1) to (I-18).

Particularly preferred embodiments of the compounds of the formulae (I-8) and (I-17) correspond to the formulae (I-8-A) and (I-17-A)

formula (I-8-A)

formula (I-17-A)

where the symbols occurring are as defined above.

The preferred embodiments of $R^0$, $Ar^1$ and A, in particular, apply to formulae (I-8-A) and (I-17-A).

The following table shows examples of compounds of the formula (I).

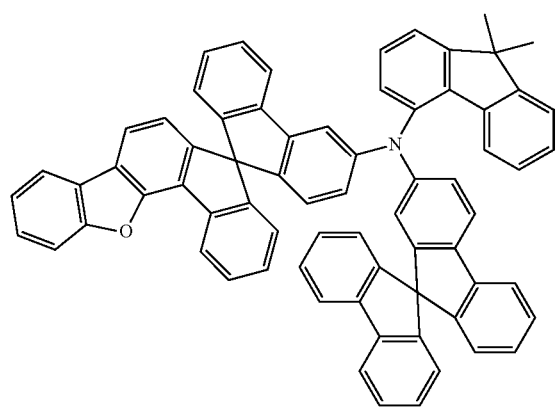
1
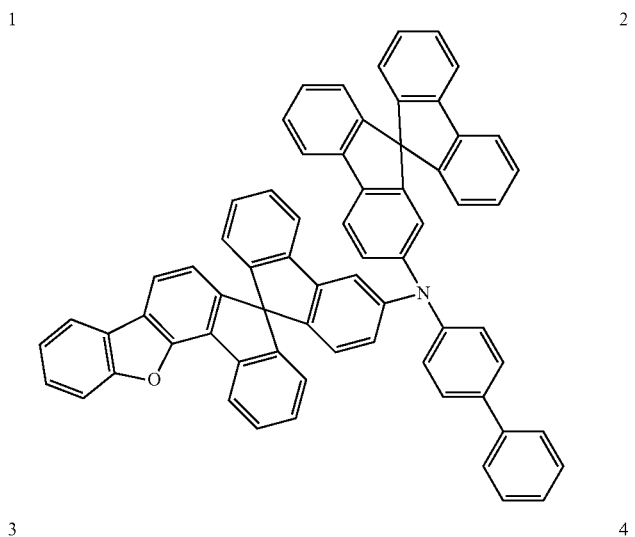
2
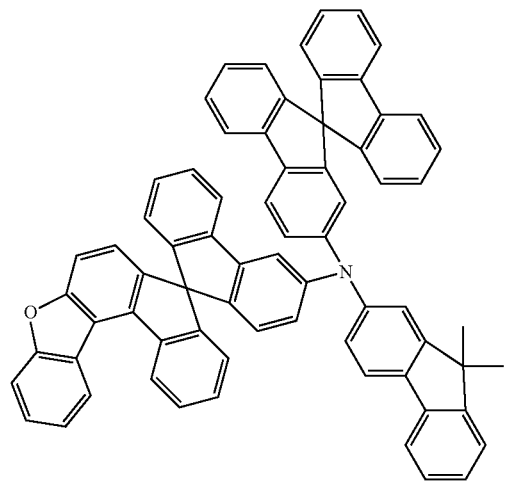
3
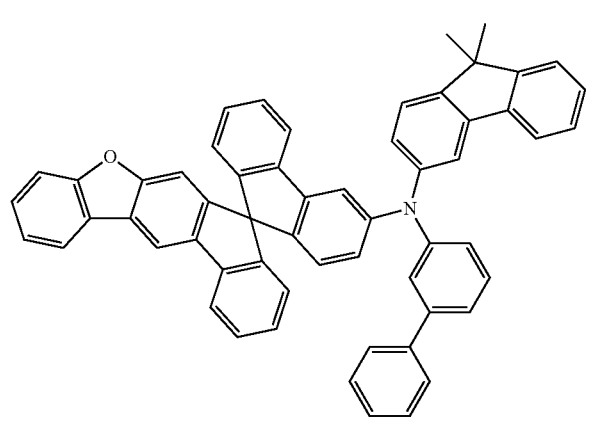
4
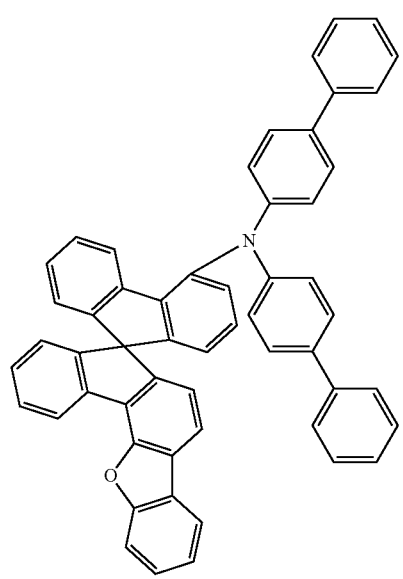
5
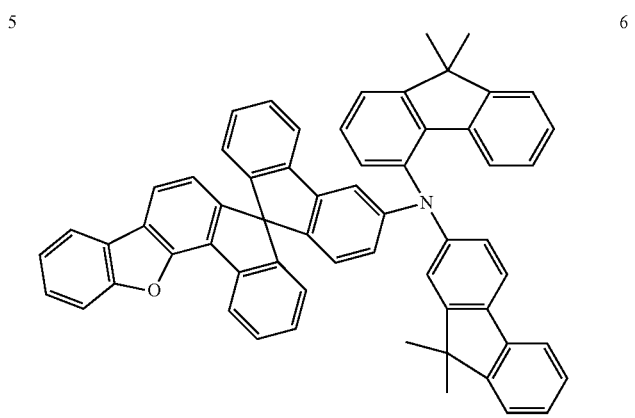
6

-continued
7
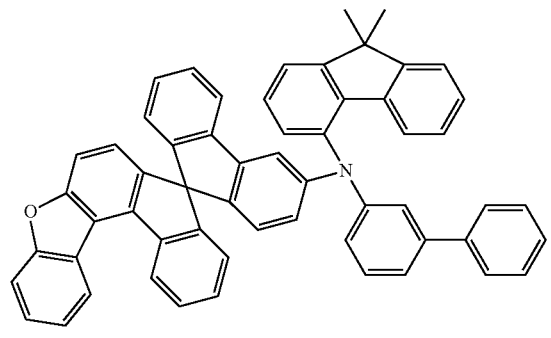
8
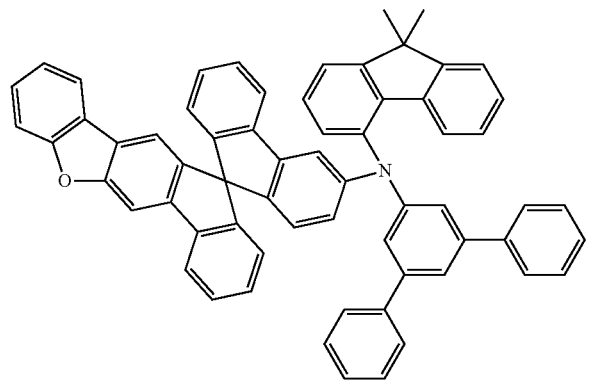
9
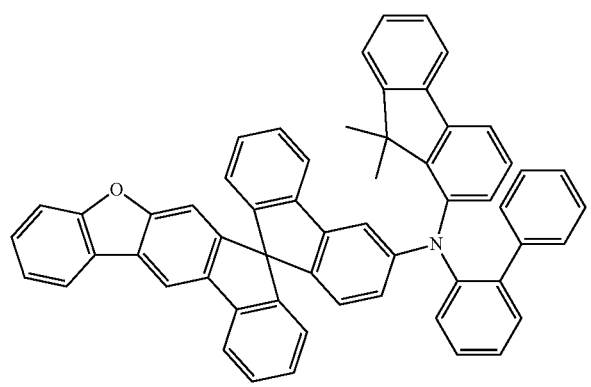
10
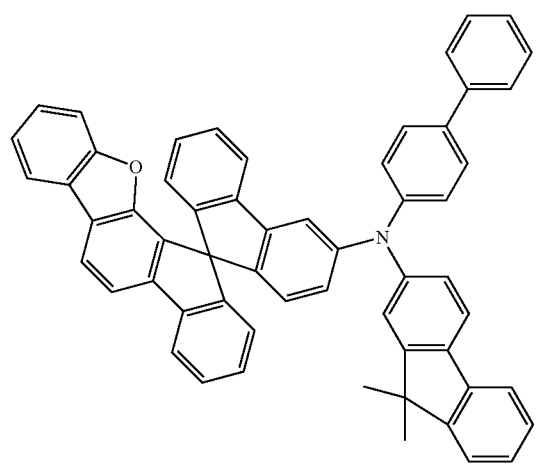
11
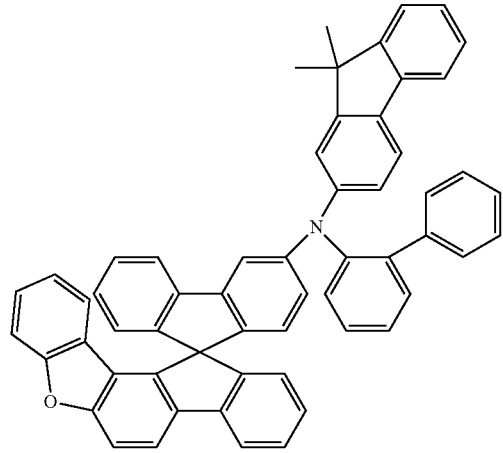
12
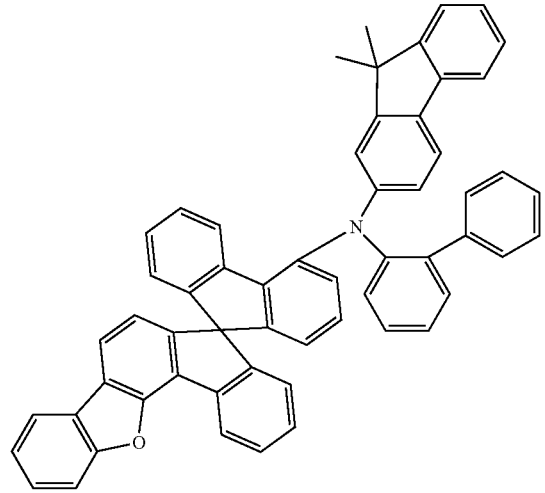

-continued
13
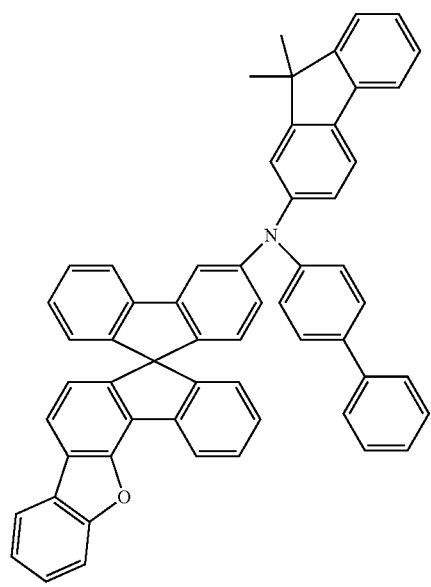
14
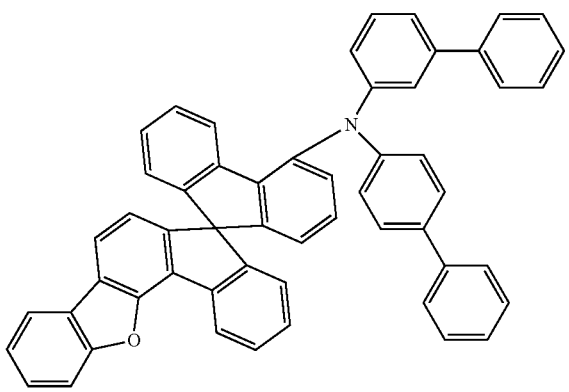
15
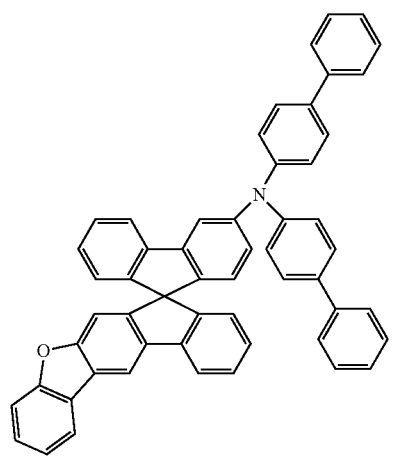
16
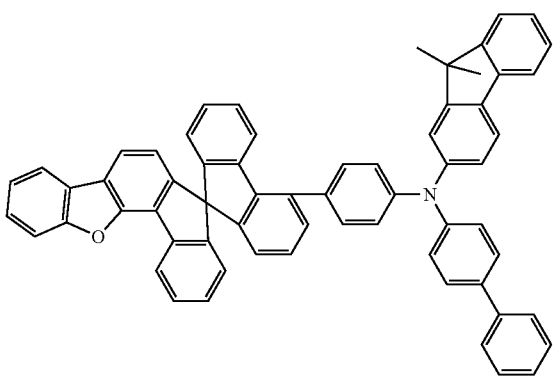
17
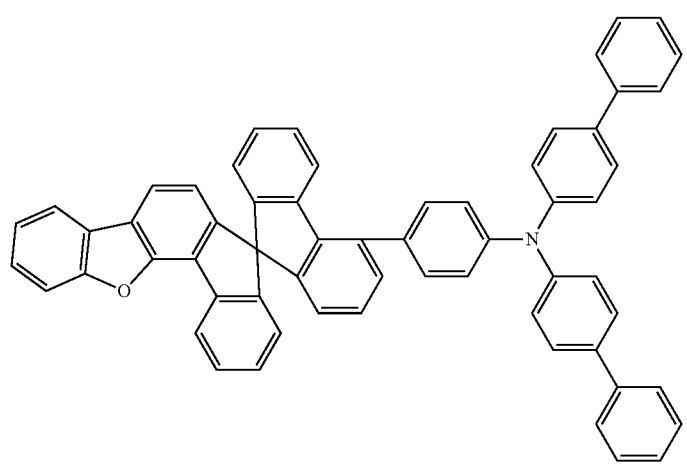

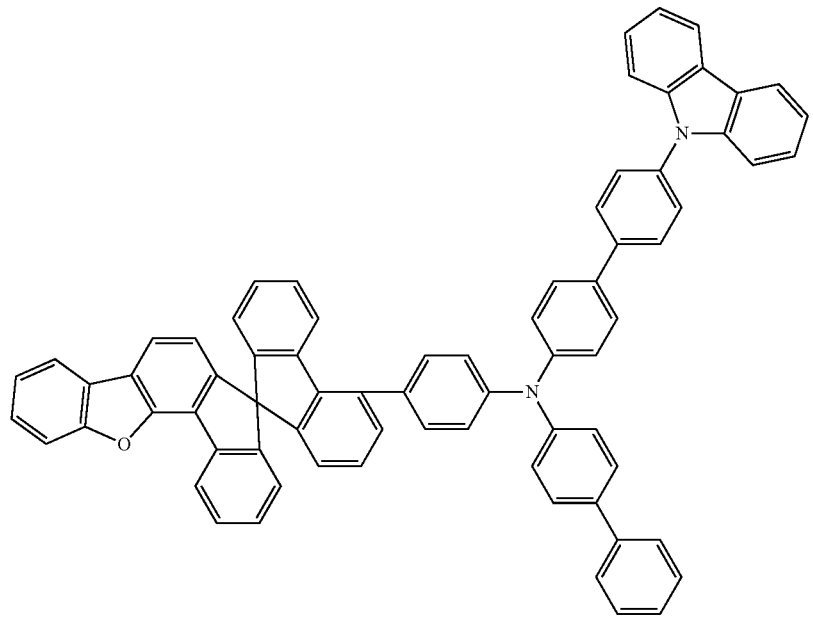
18
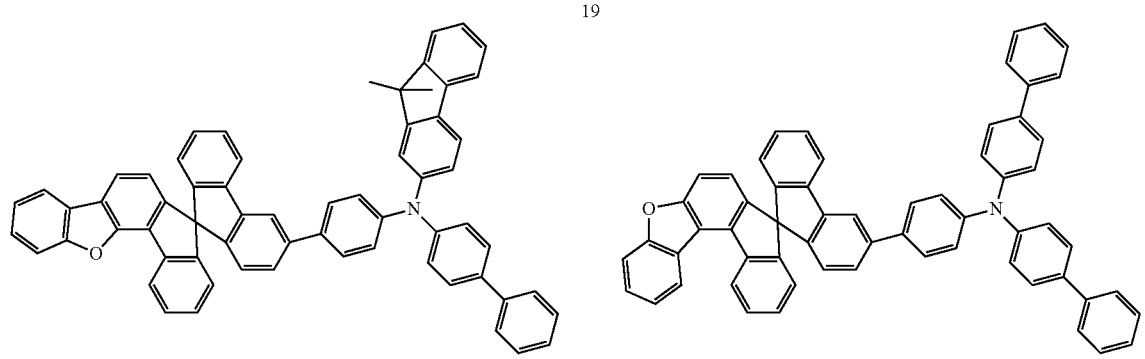
19
20
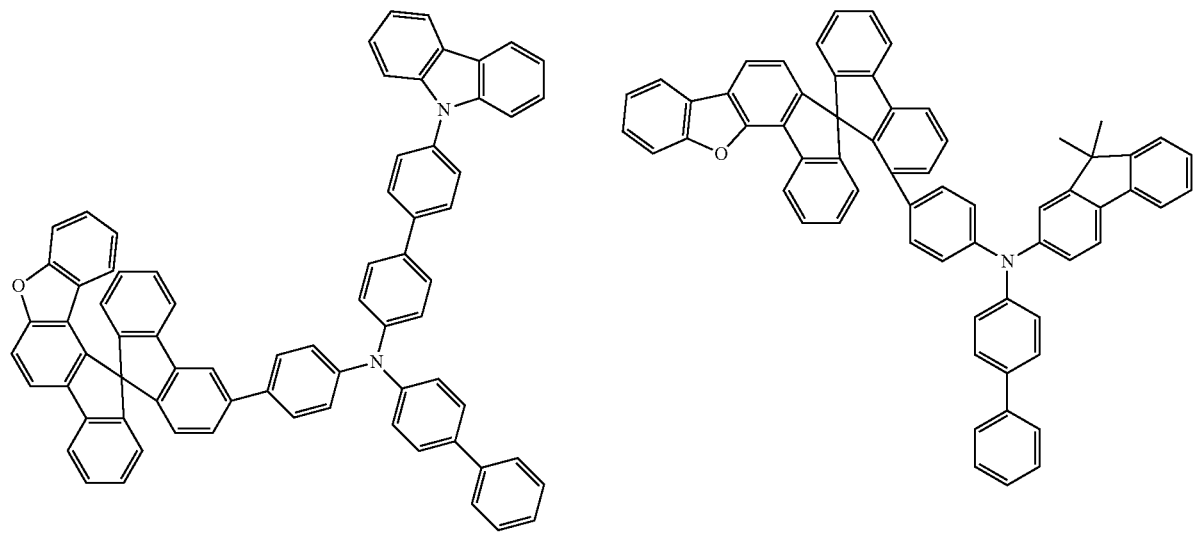
21
22

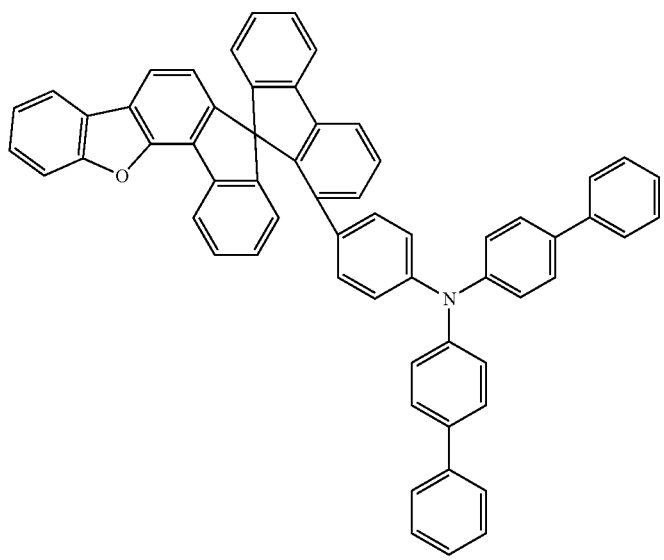
23
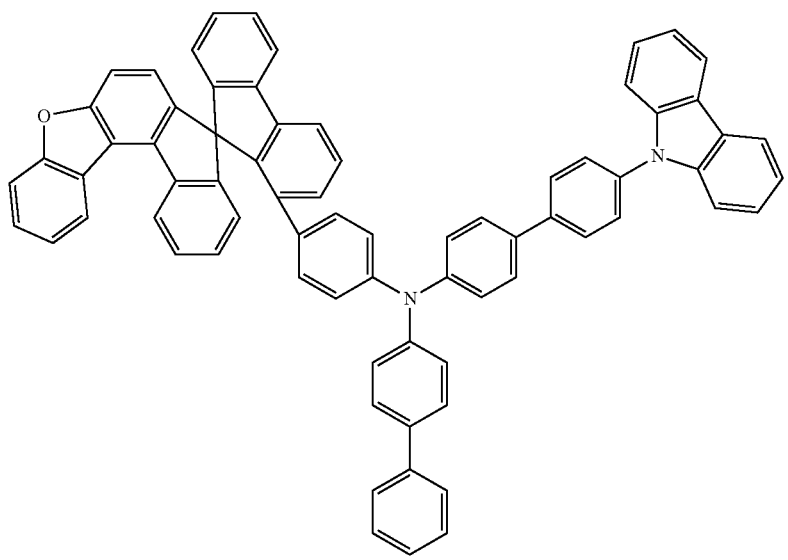
24
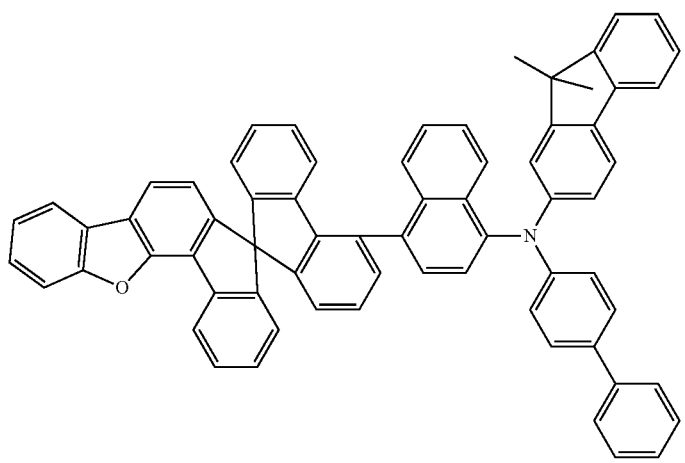
25

-continued
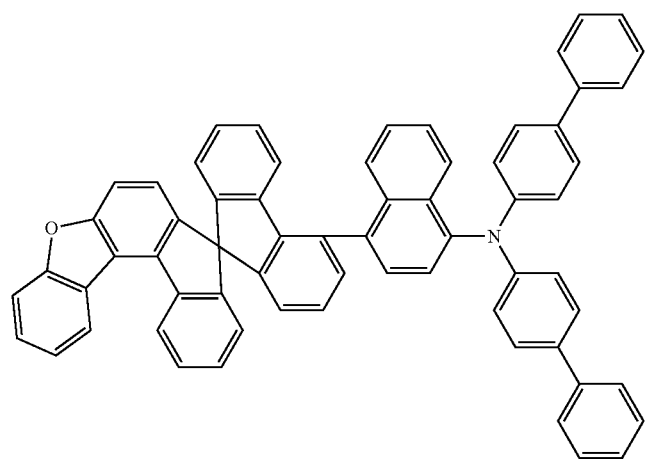
26
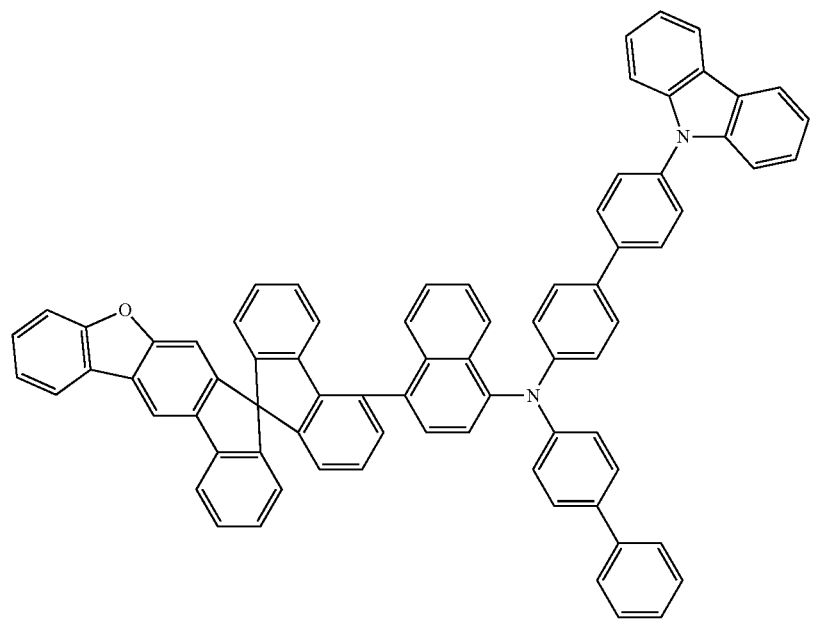
27
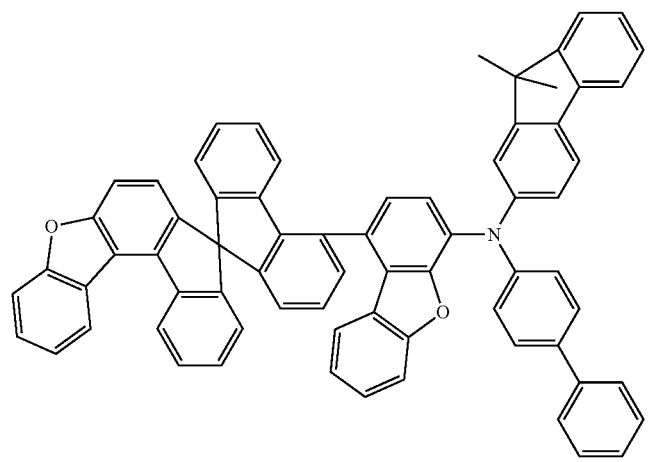
28

-continued
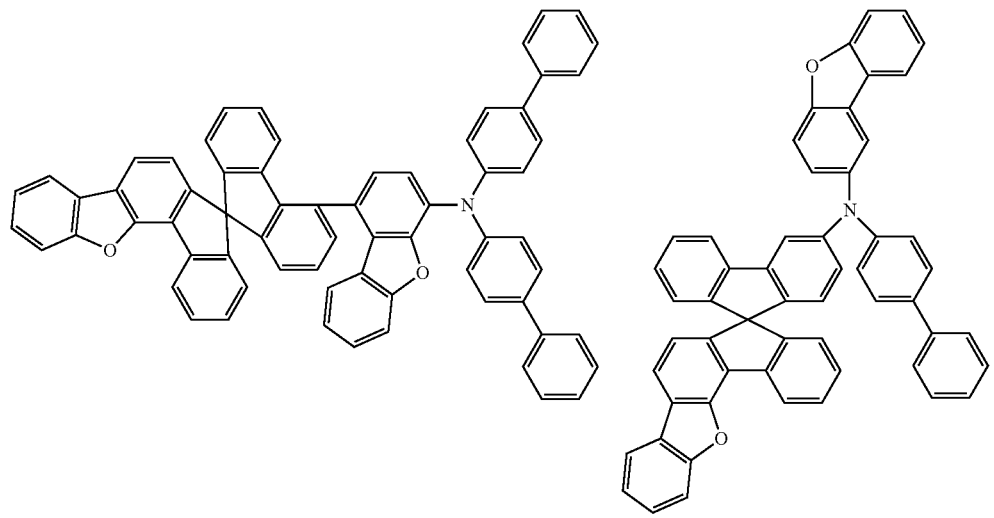
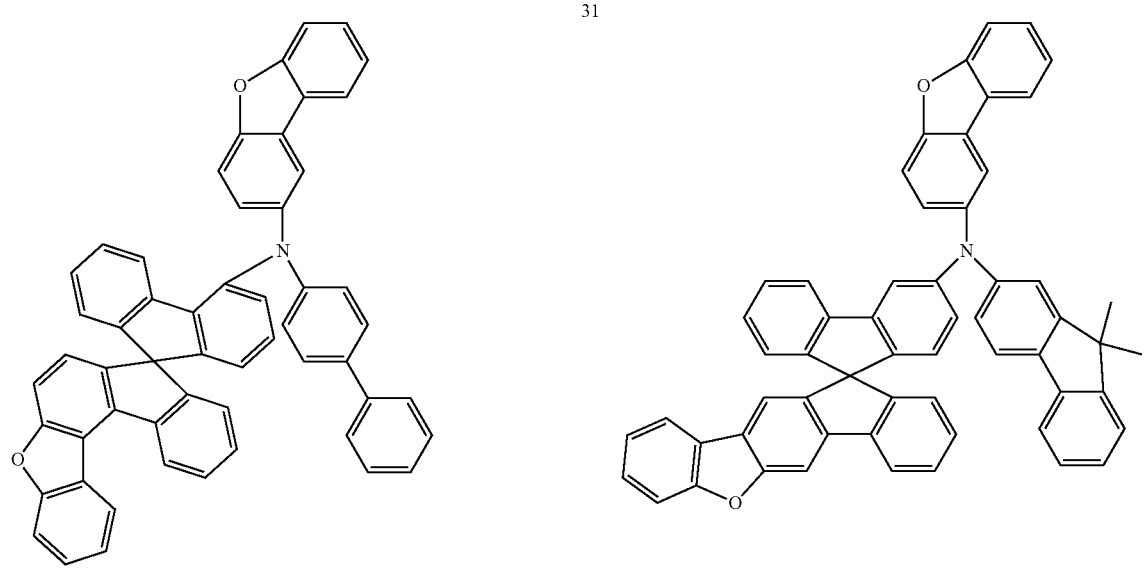
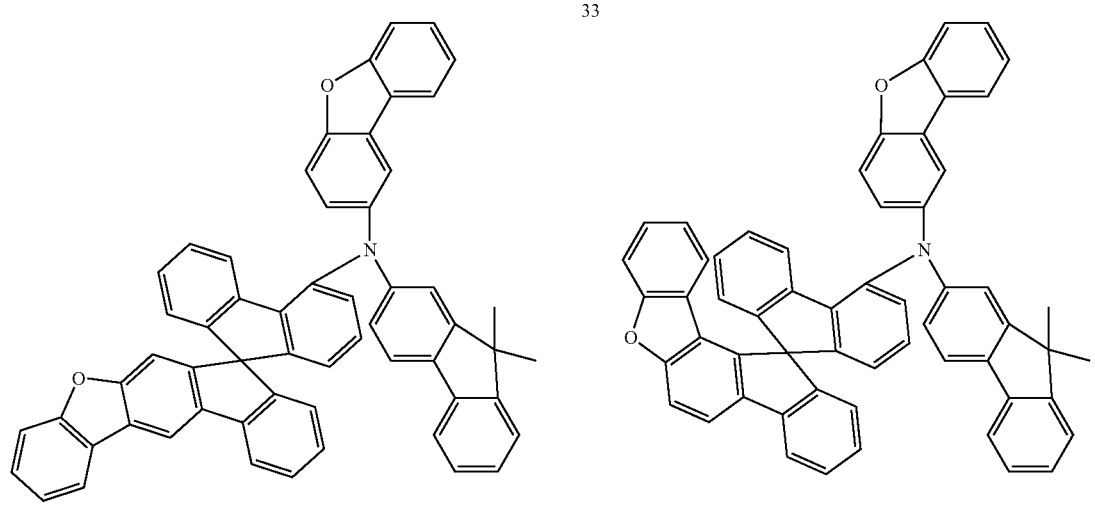

-continued
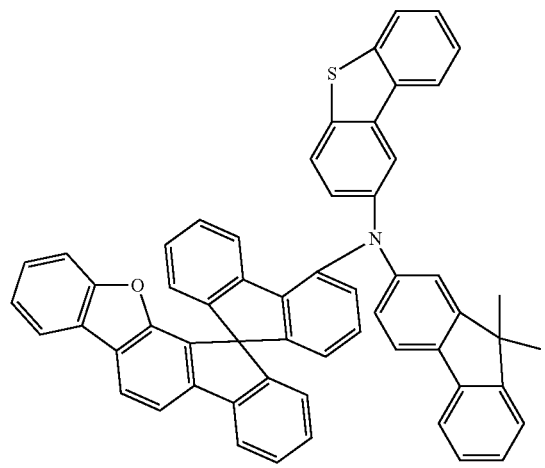
35
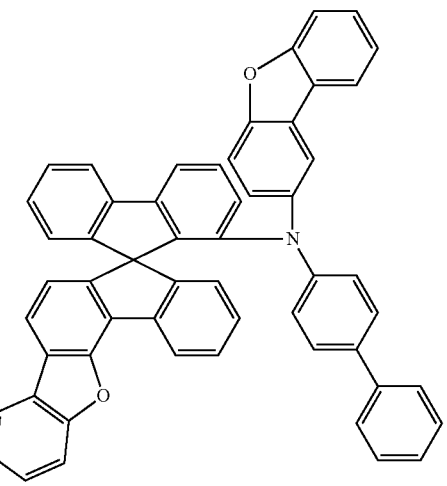
36
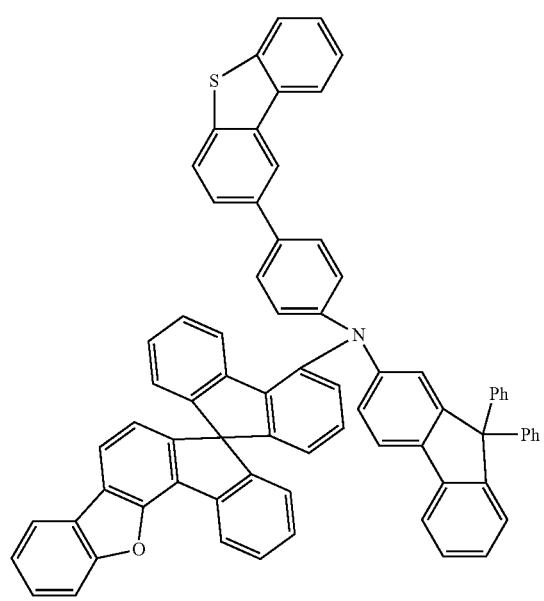
37
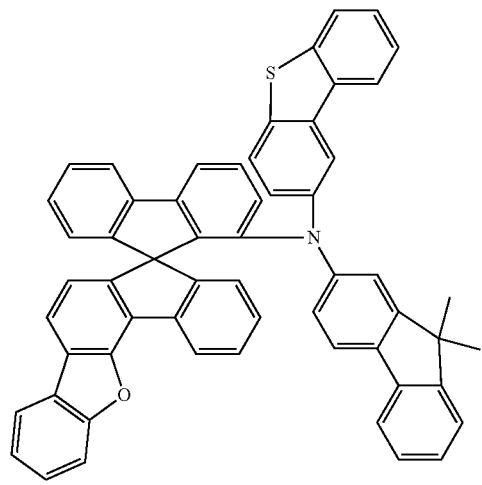
38
39
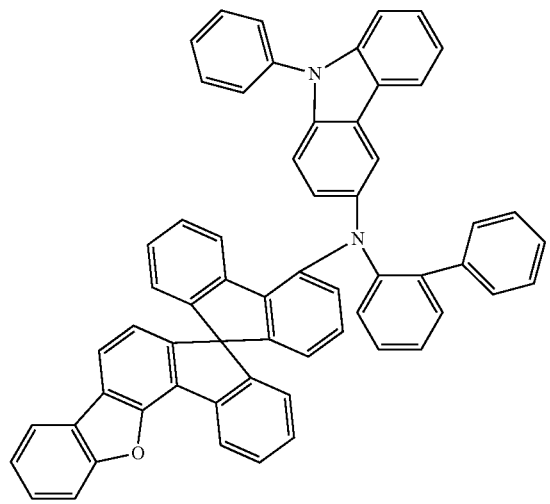
40

-continued
41 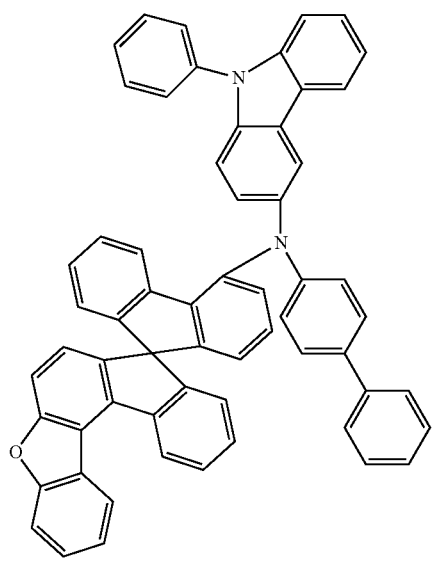
42 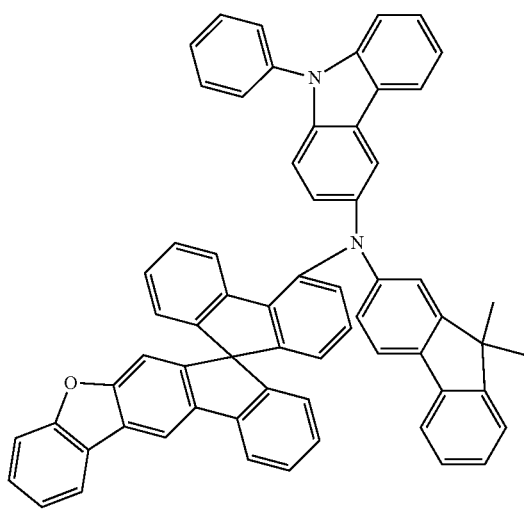
43 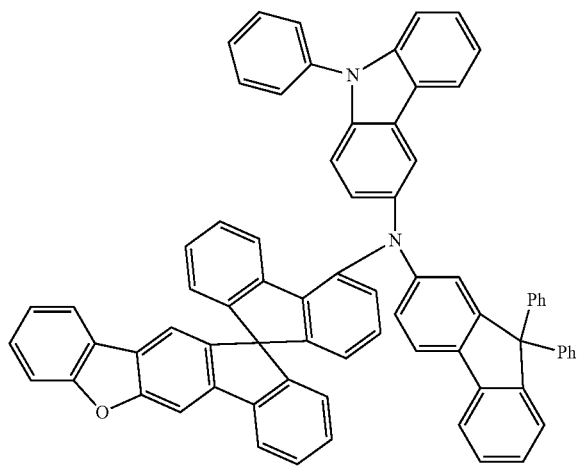
44 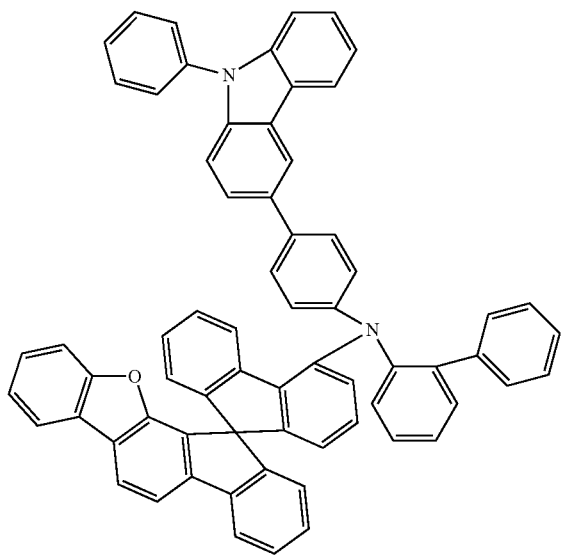

45
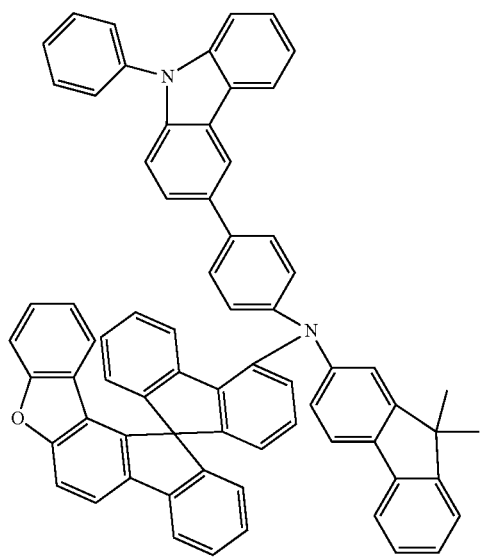
46
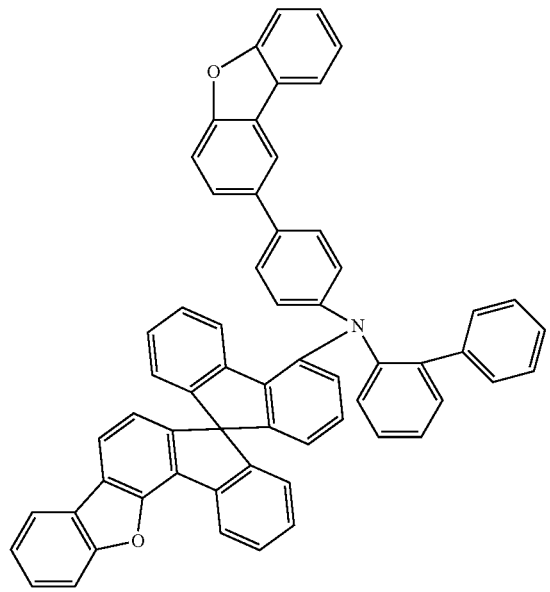
47
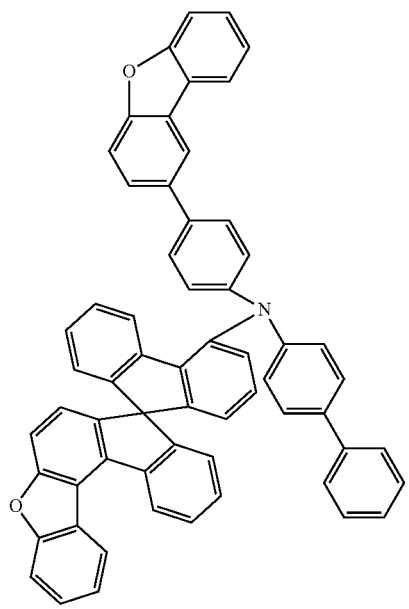
48
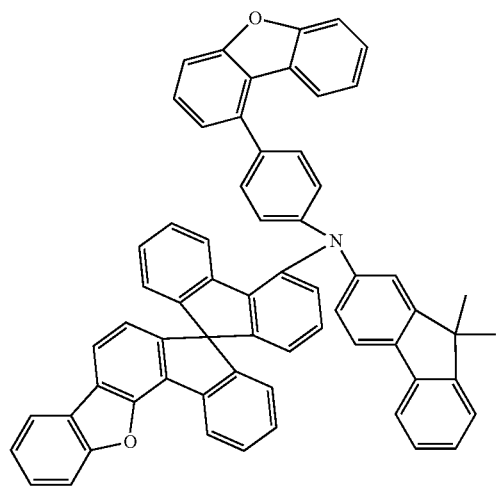

-continued
49
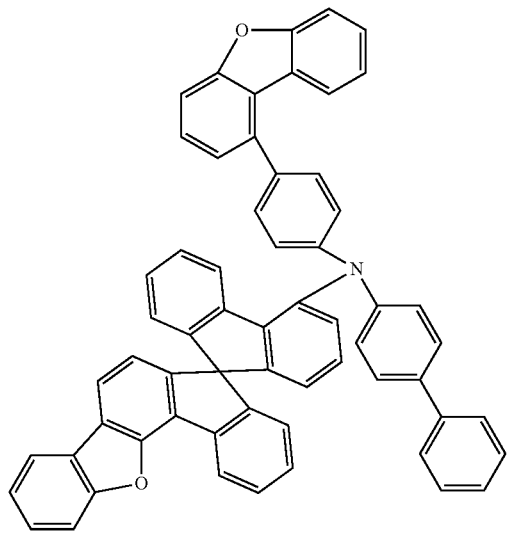
50
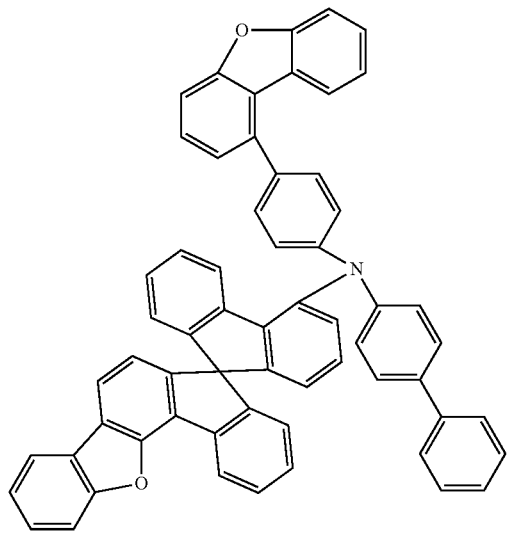
51
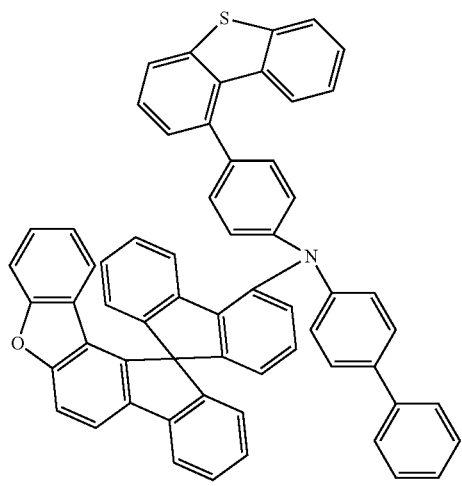
52
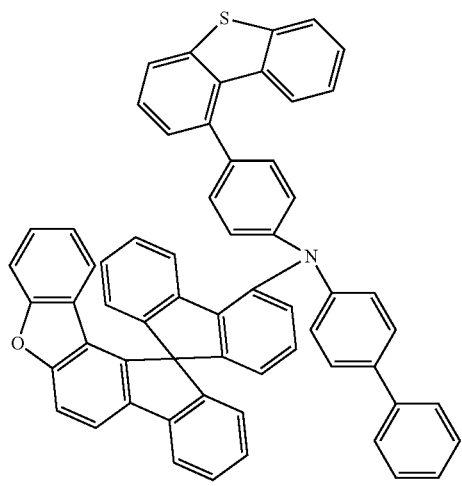
53
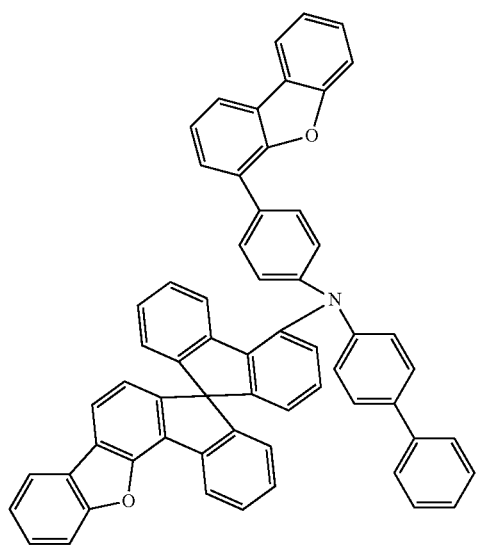
54
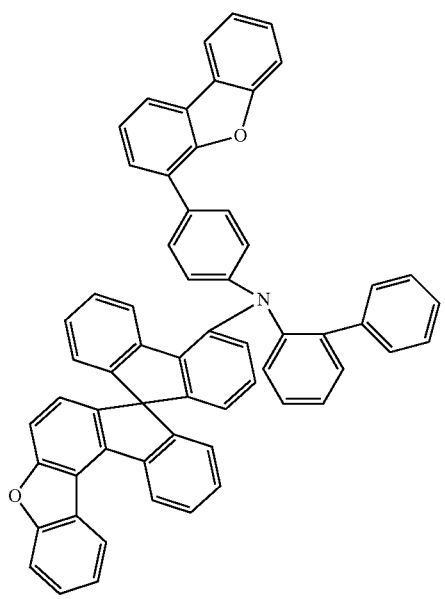

-continued
55
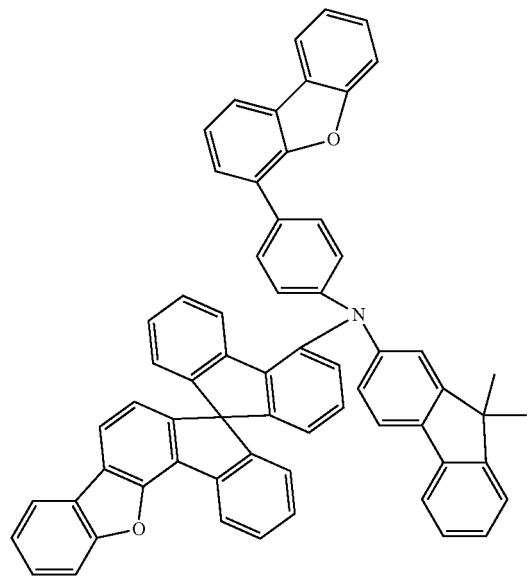
56
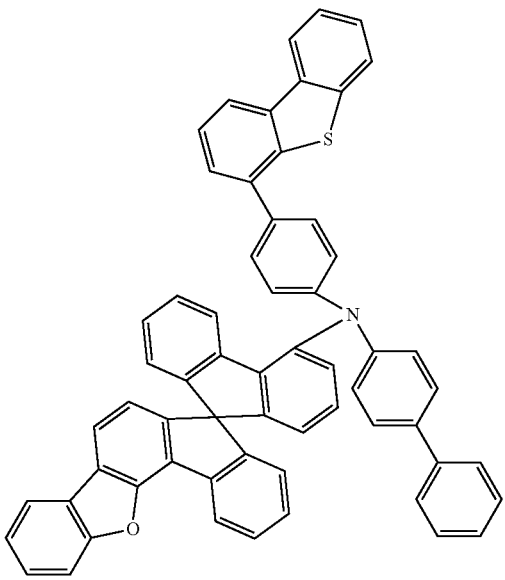
57
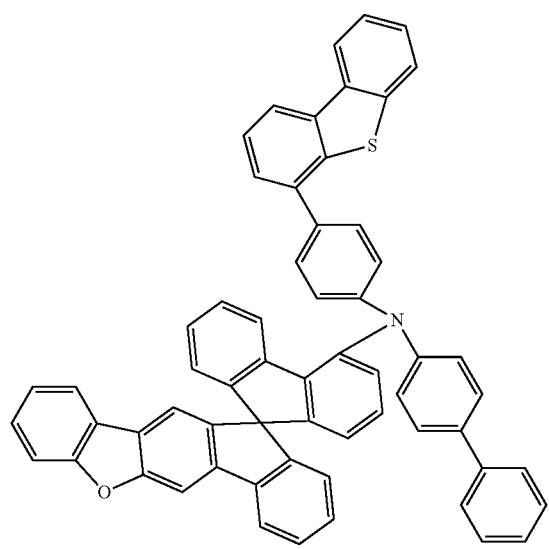
58
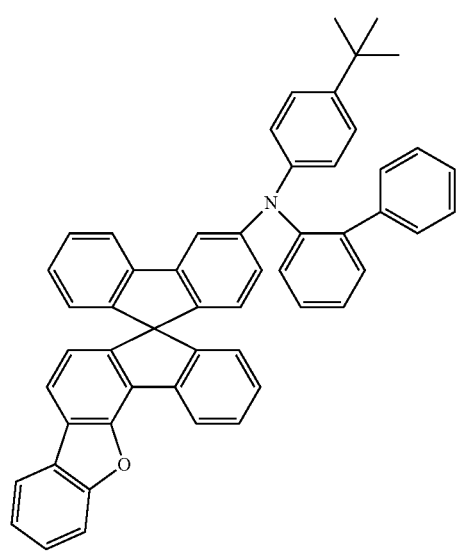
59
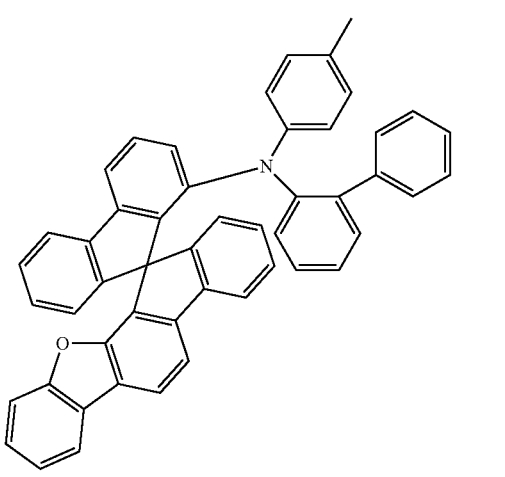
60

-continued
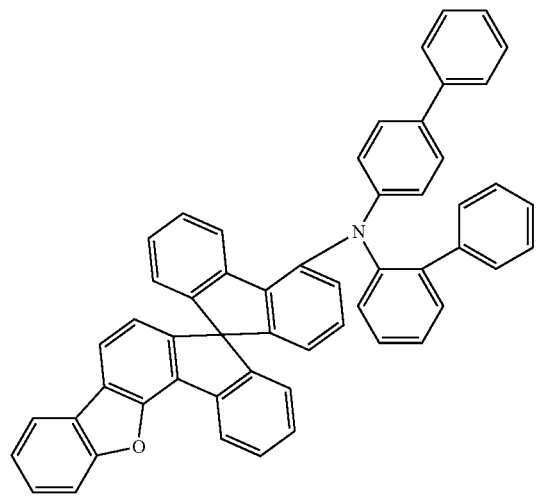
61
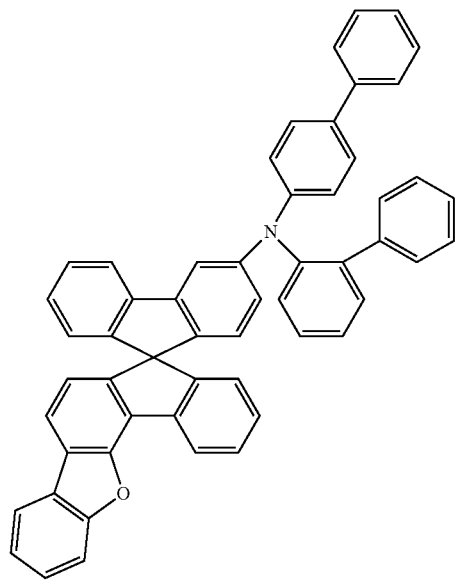
62
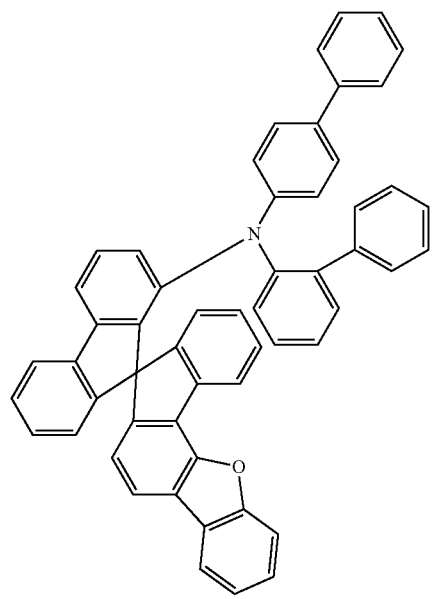
63
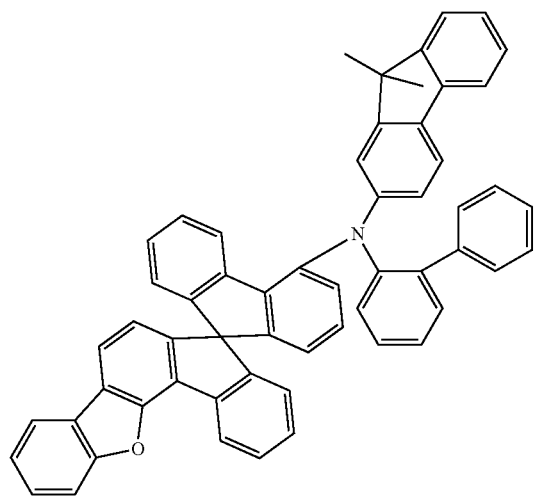
64

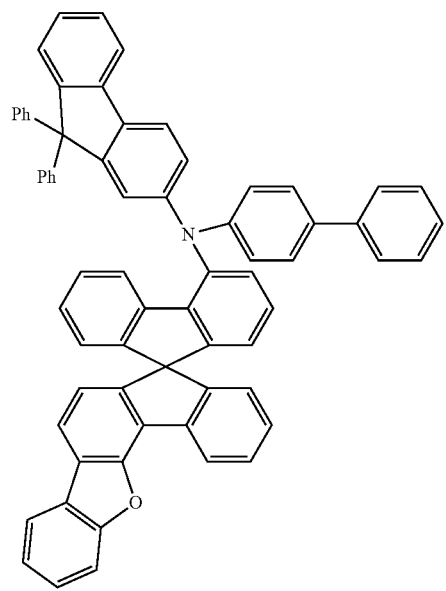
65
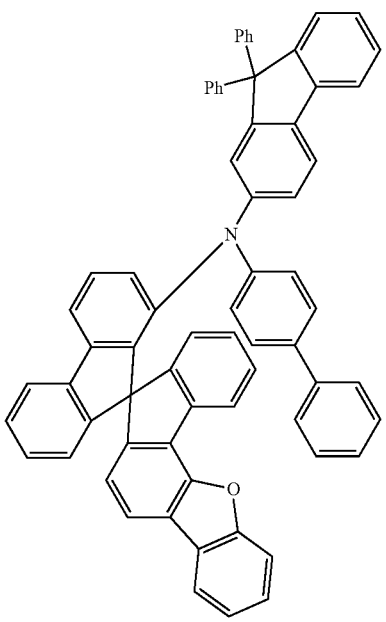
66
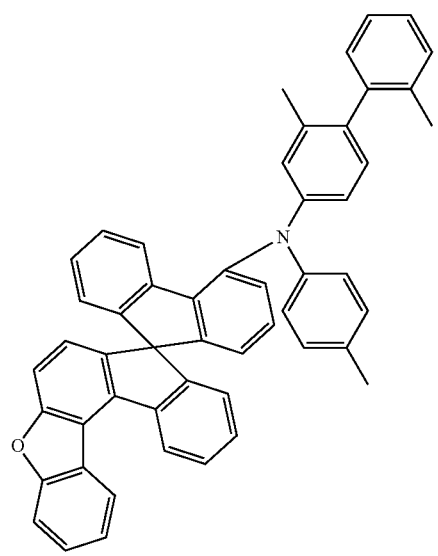
67
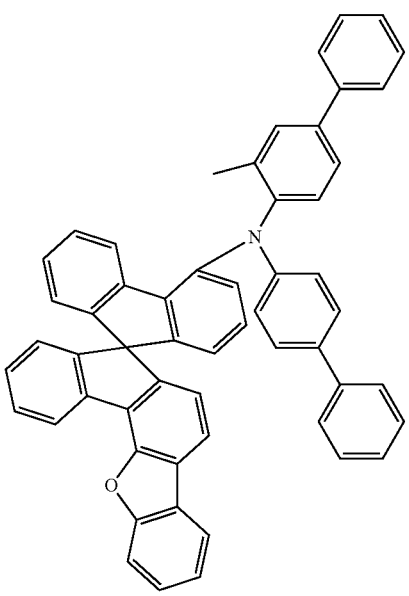
68

-continued
69
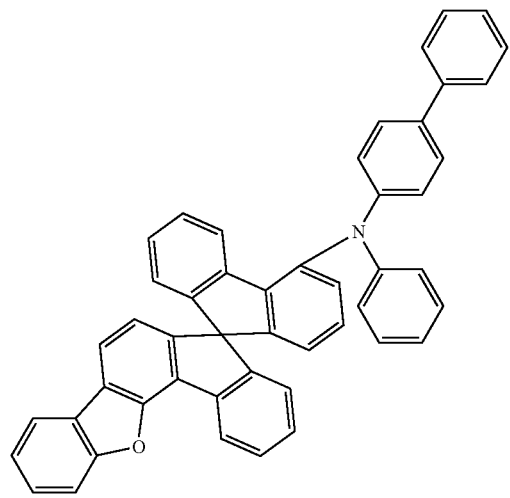
70
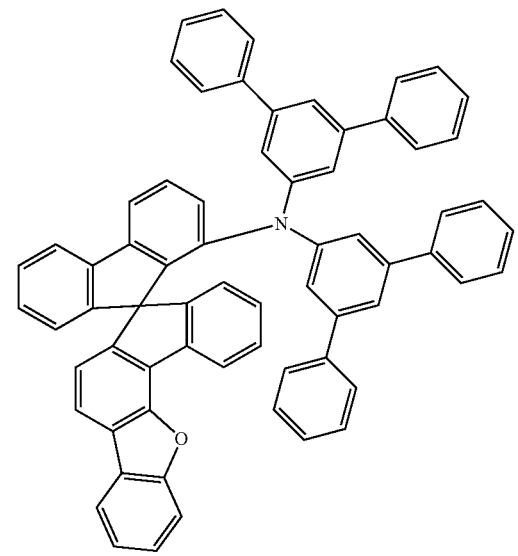
71
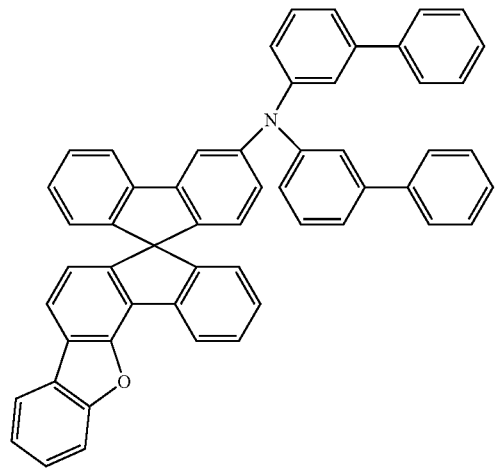
72
73
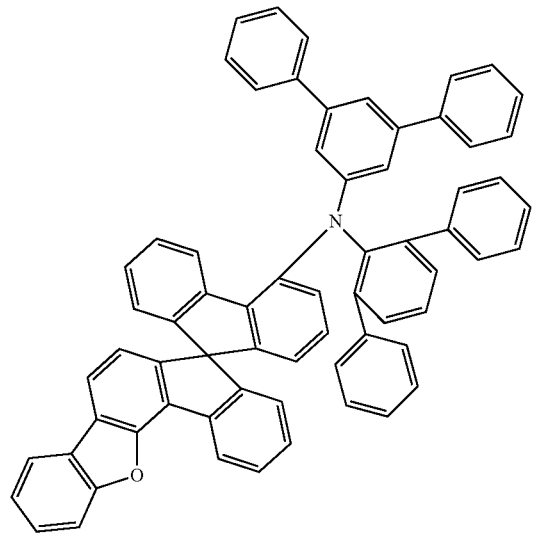
74
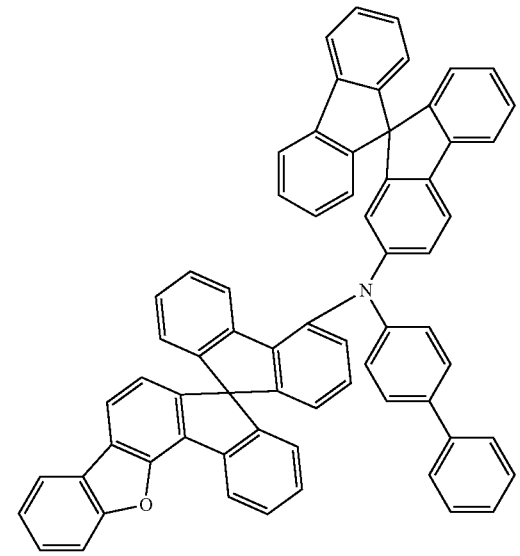

-continued
75
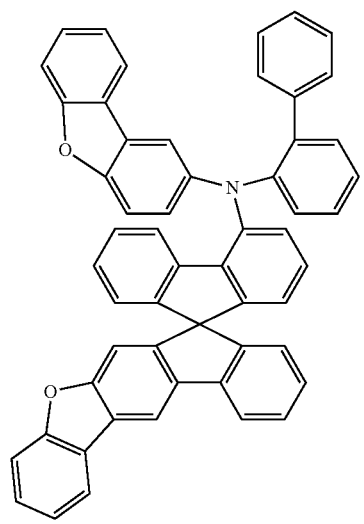
76
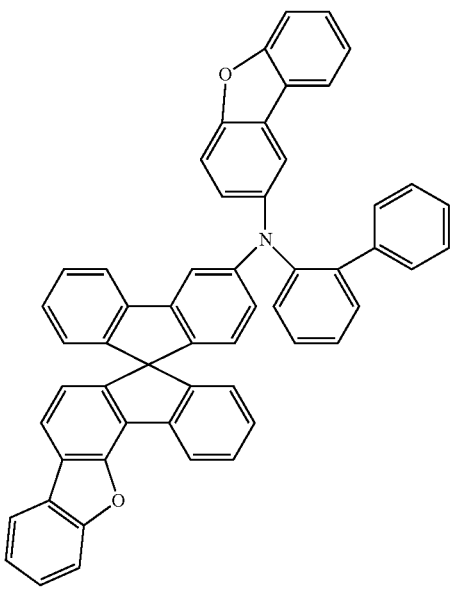
77
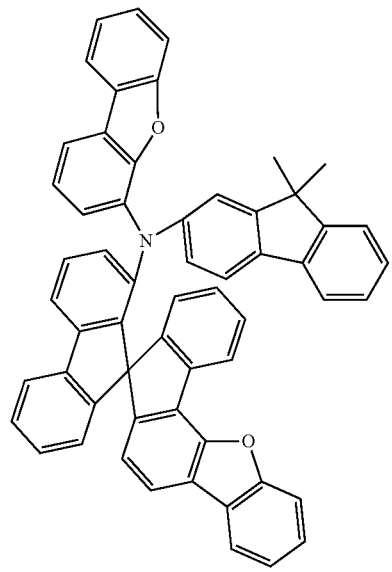
78
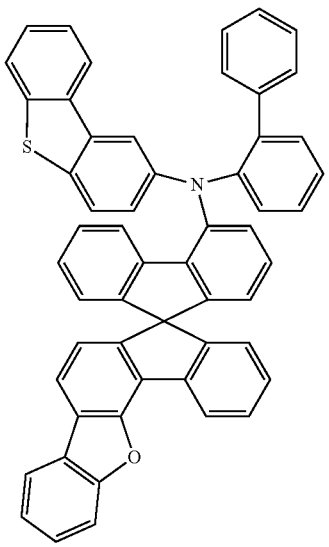

-continued
79
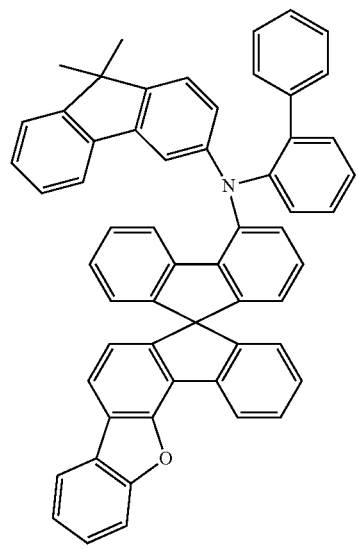
80
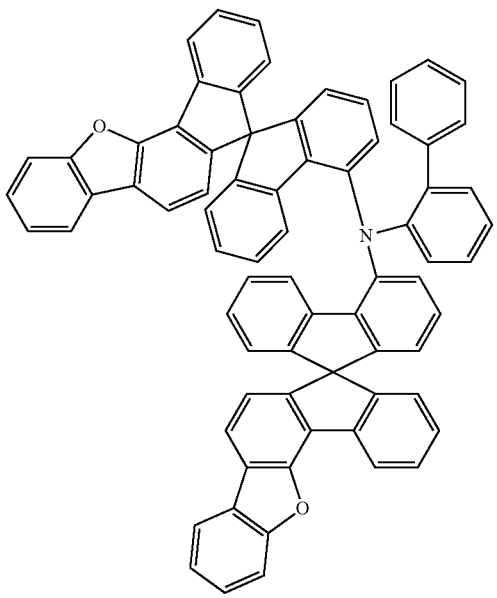
81
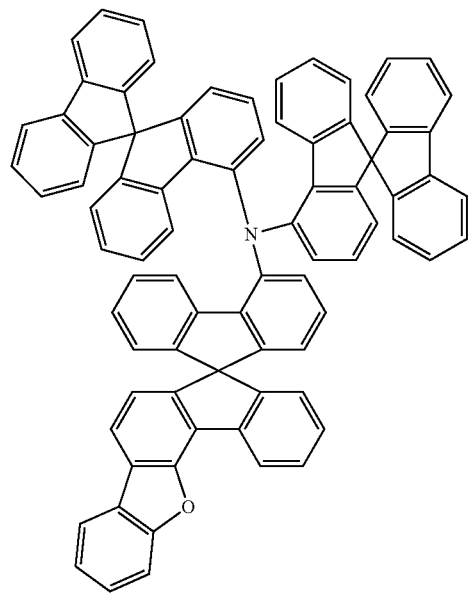
82
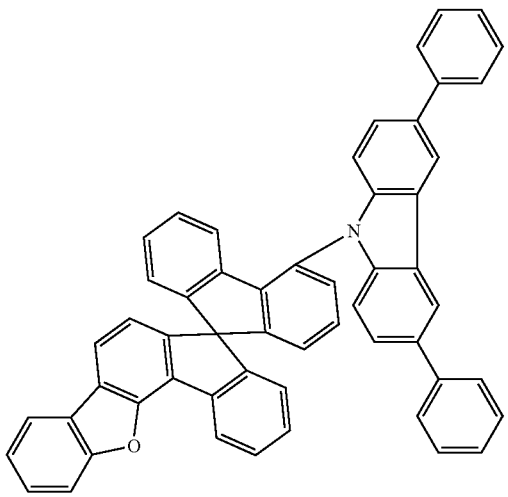

-continued
83
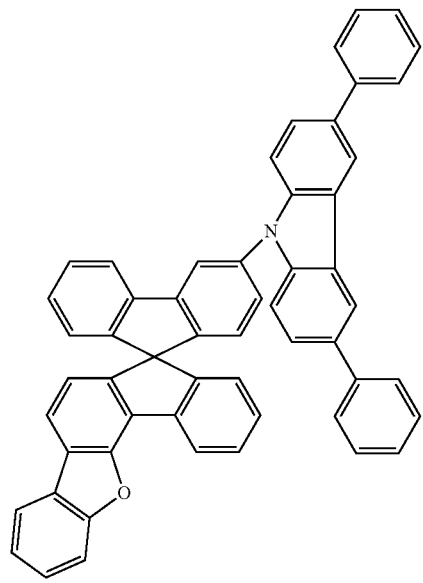
84
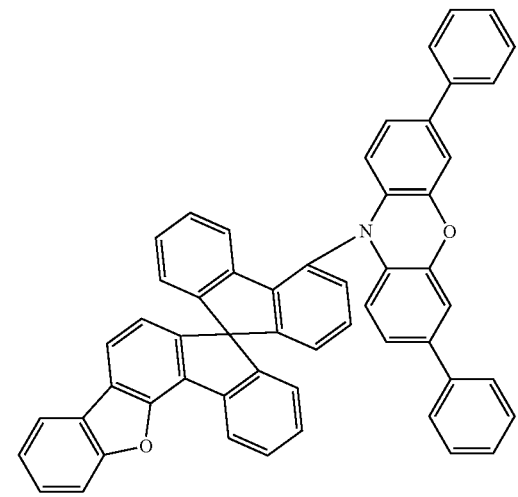
85
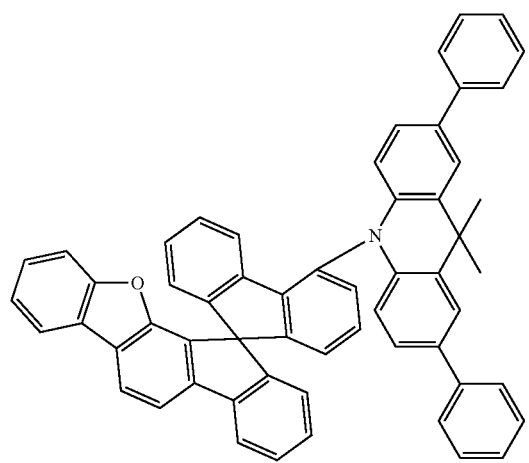
86
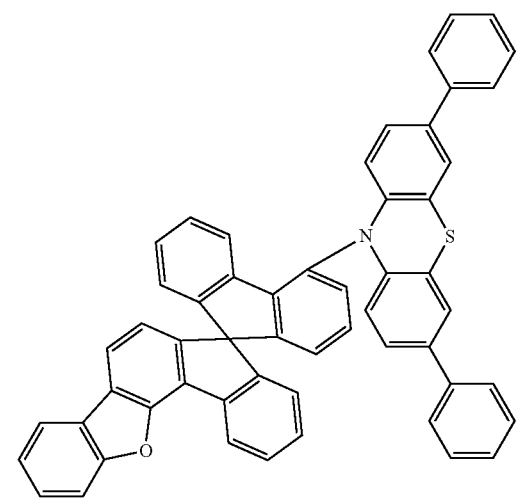
87
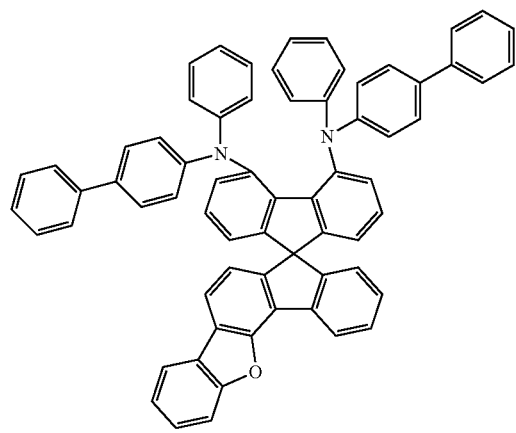
88
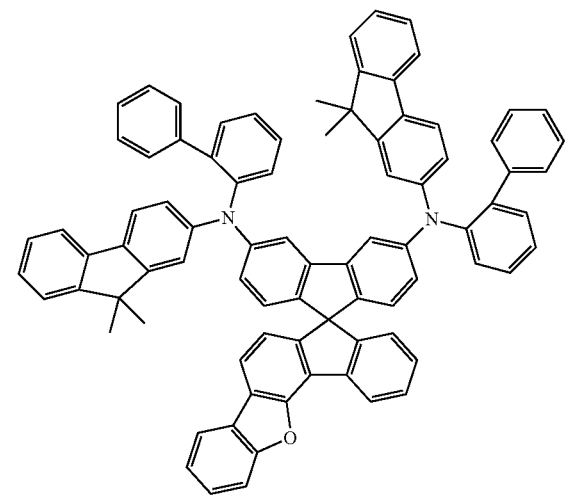

-continued
89
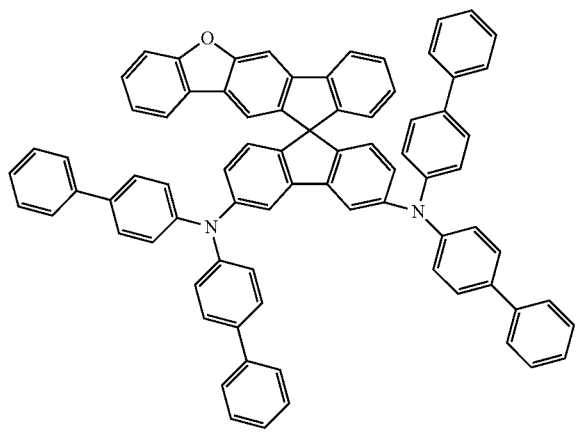
90
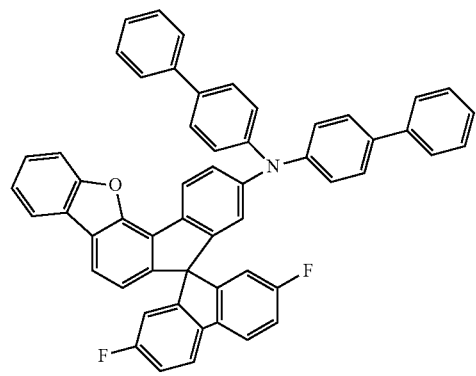
91
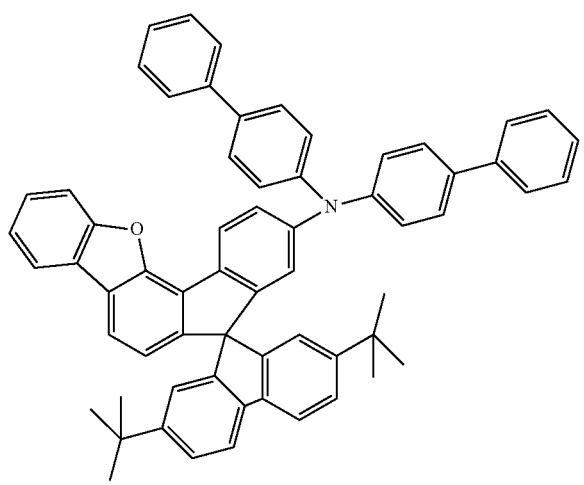
92
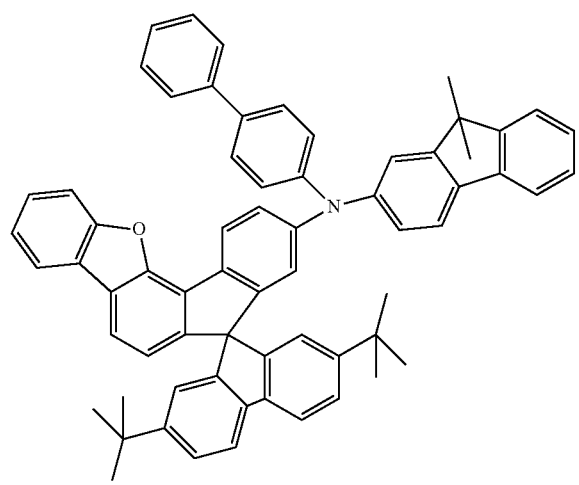
93
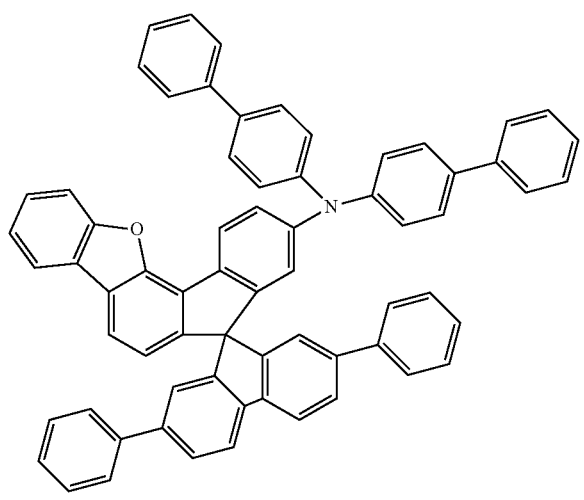
94
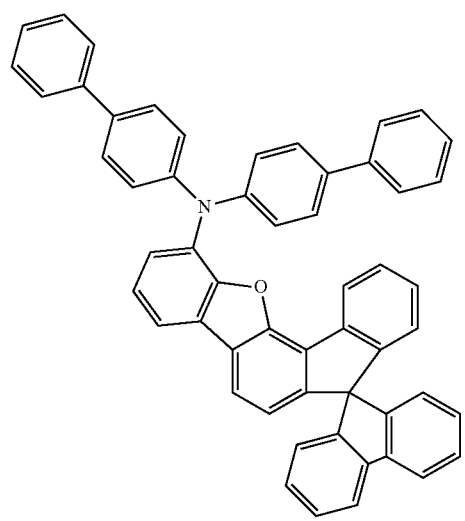

95
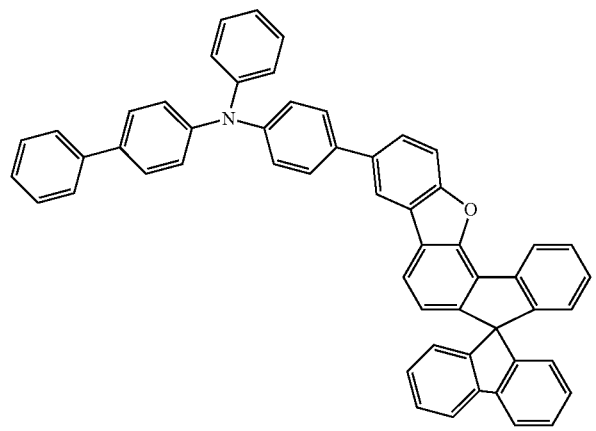
96
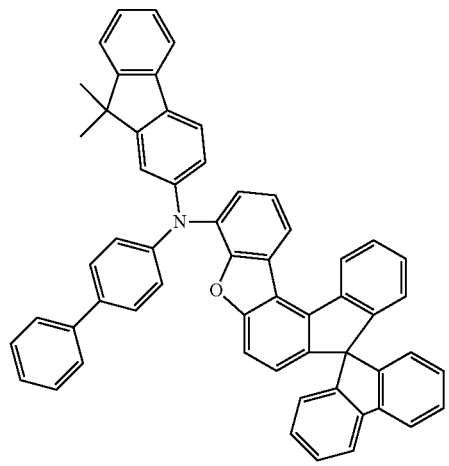
97
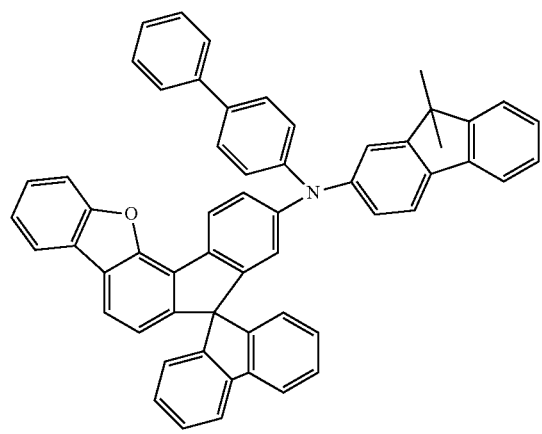
98
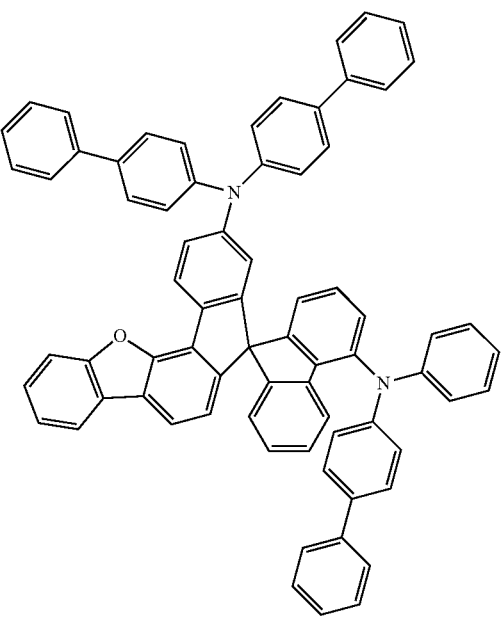

-continued
99
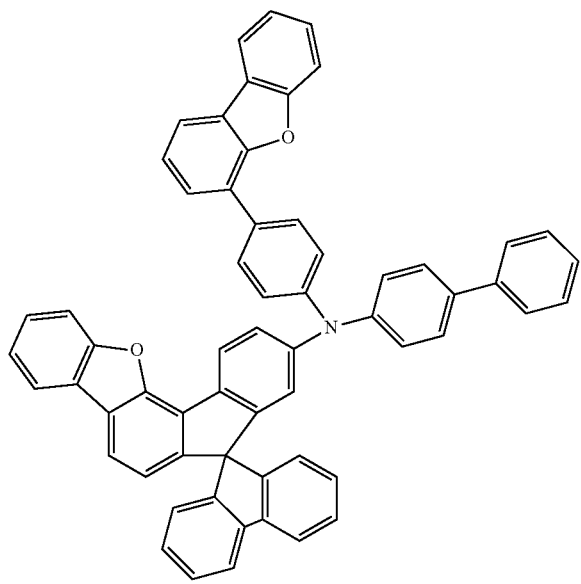
100
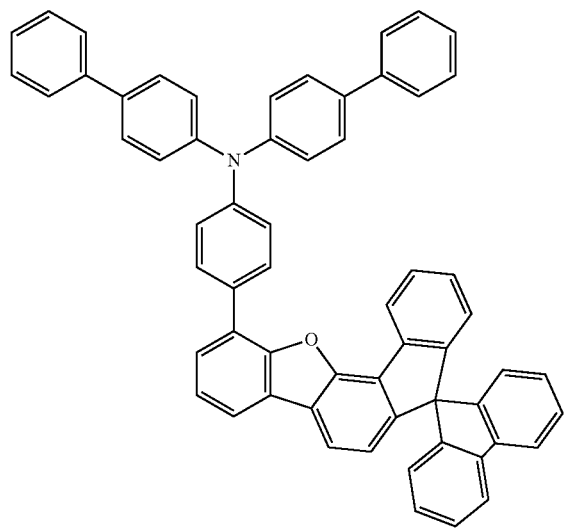
101
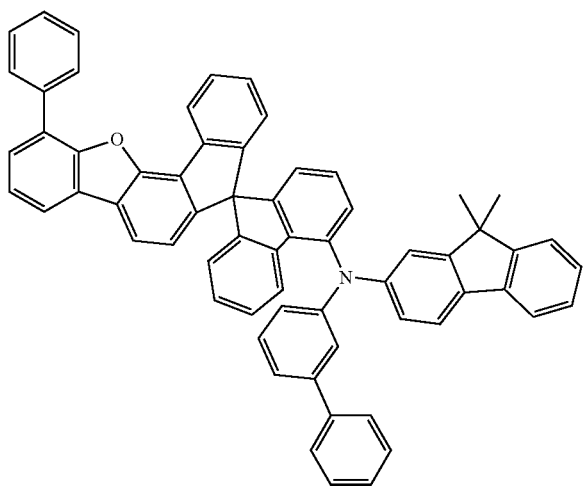
102
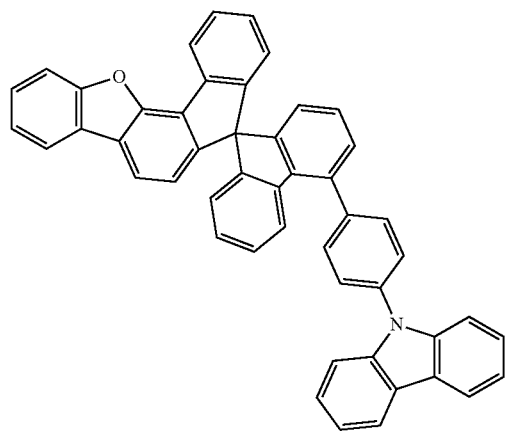
103
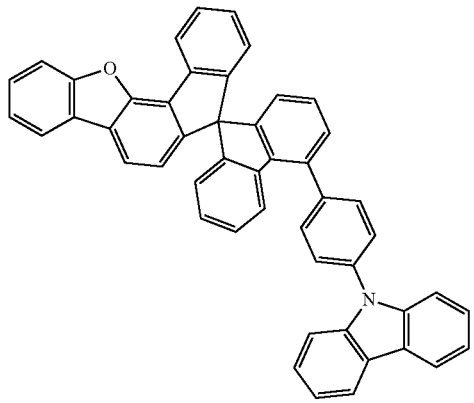
104
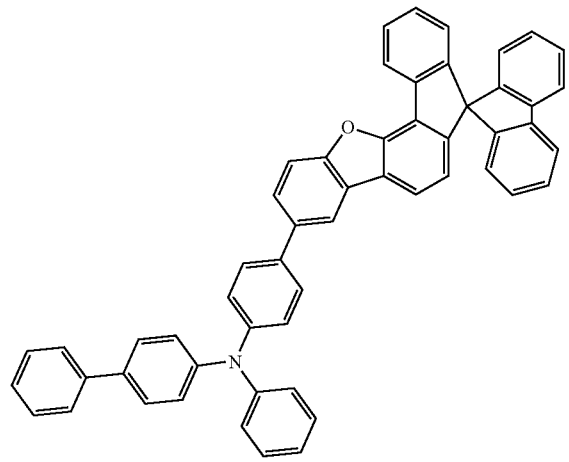

-continued
| 105 | 106 |
|---|---|
| 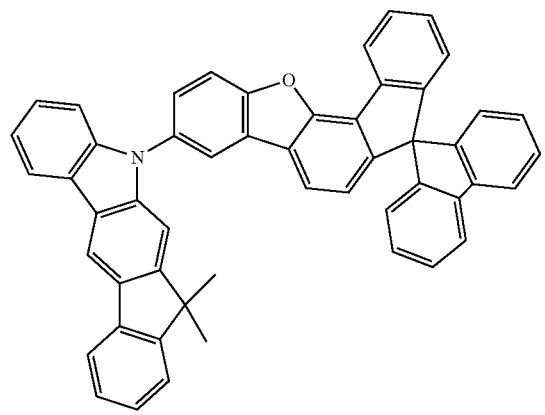 | 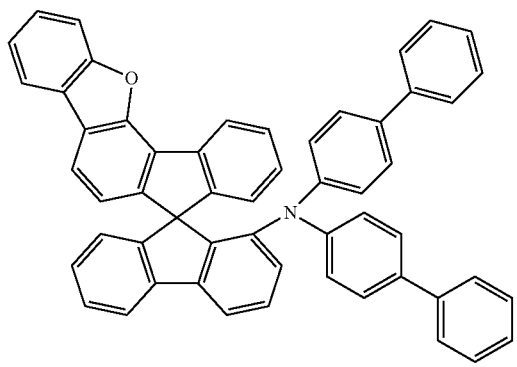 |
| 107 | 108 |
|---|---|
| 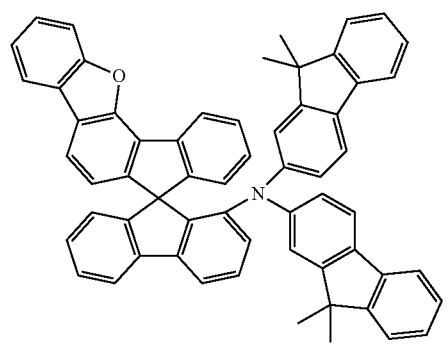 | 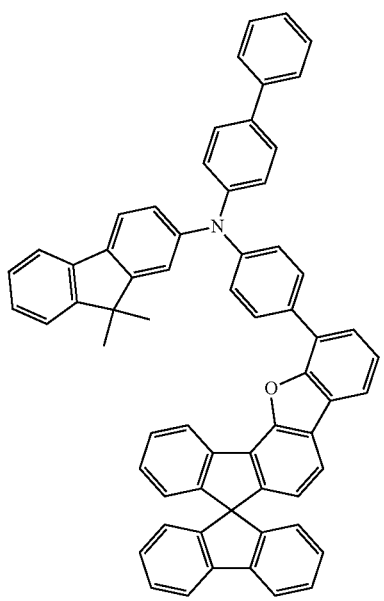 |
| 109 | 110 |
|---|---|
| 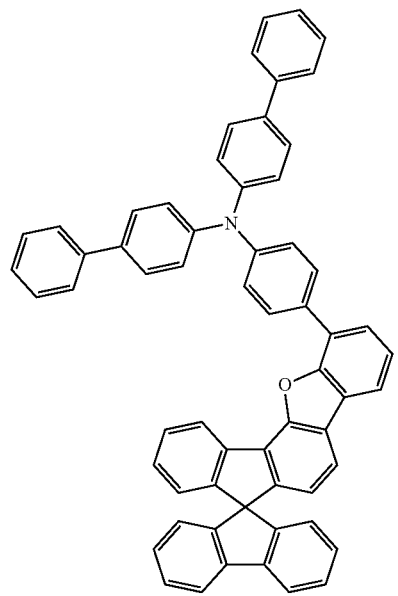 | 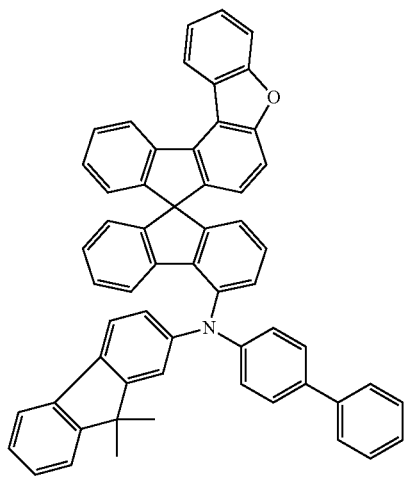 |

-continued
111
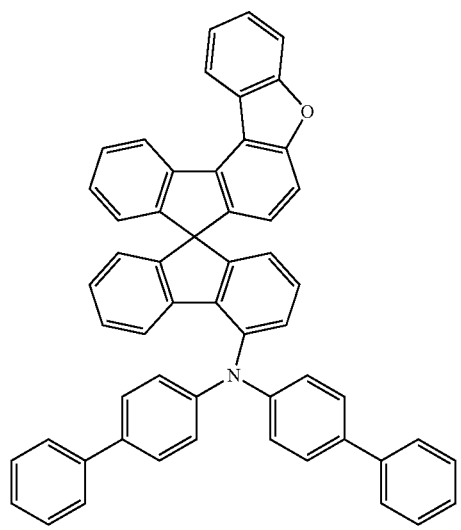
112
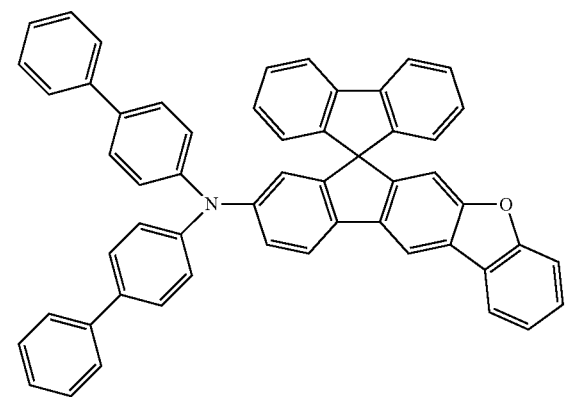
113
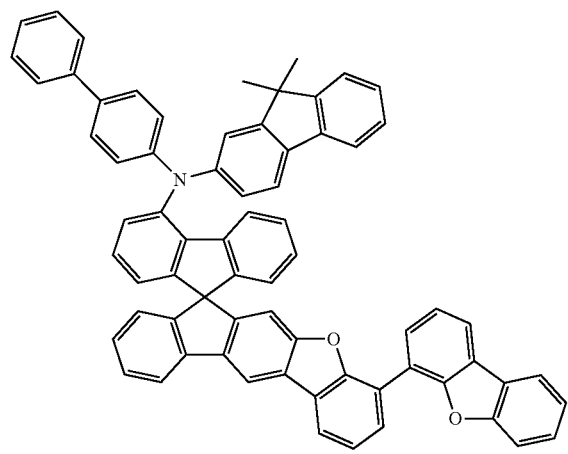
114
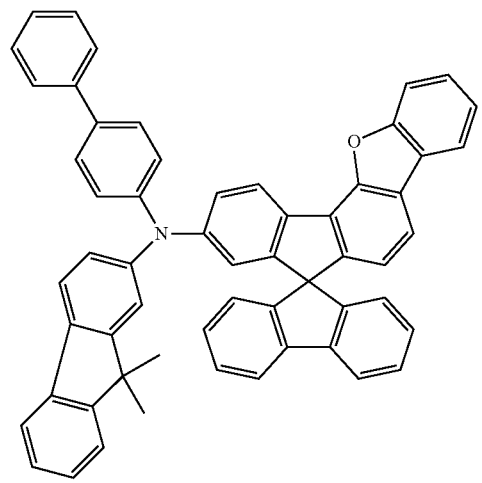
115
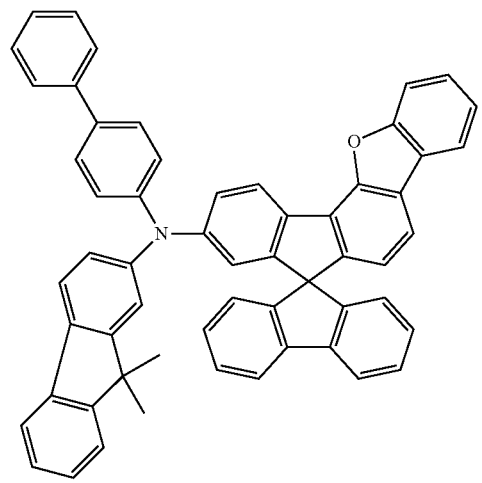
116
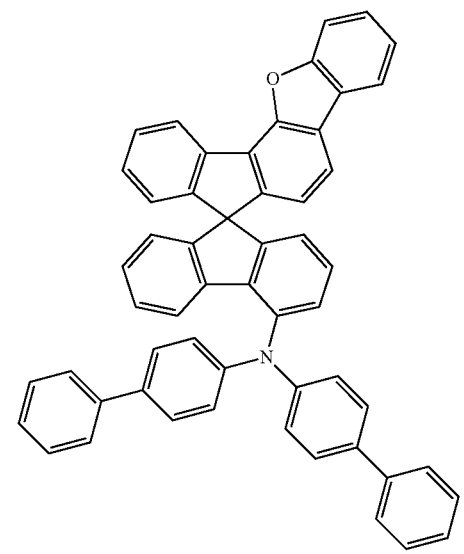

-continued
117
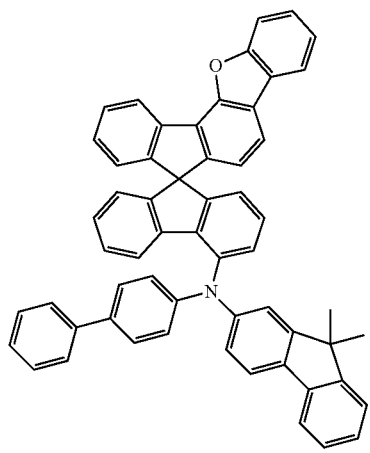
118
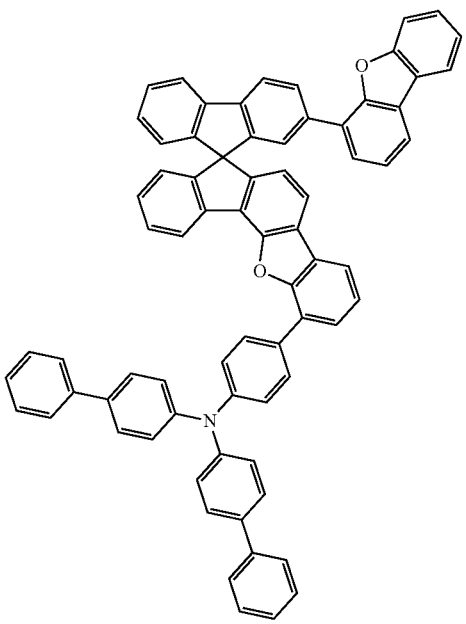
119
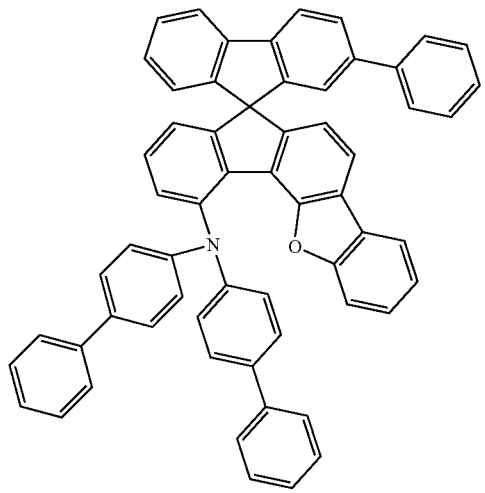
120
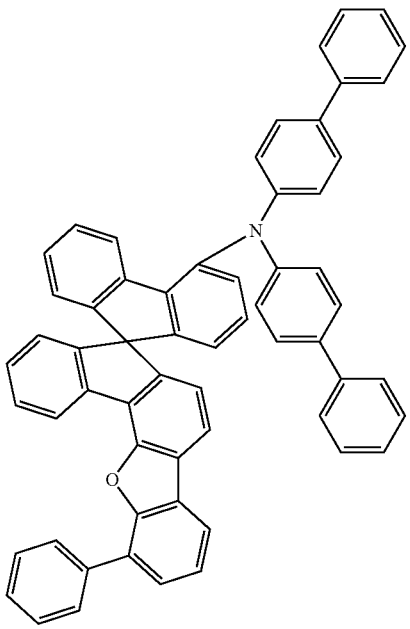

-continued
121
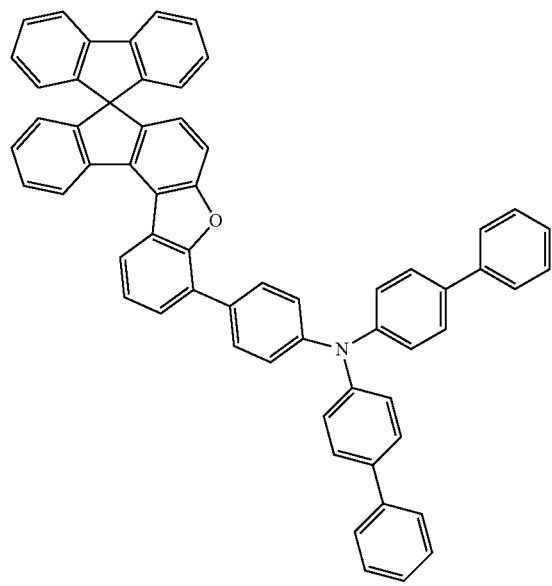
122
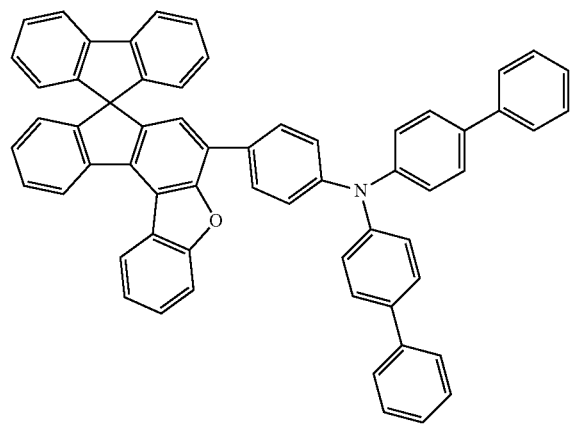
123
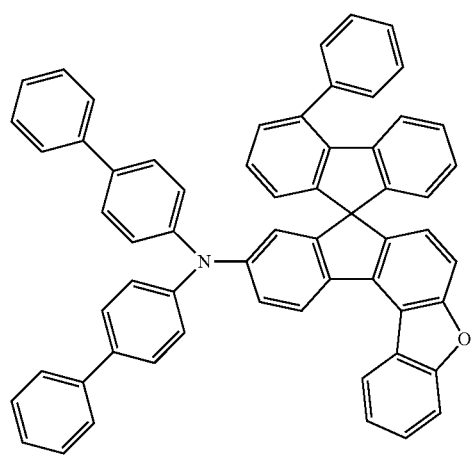
124
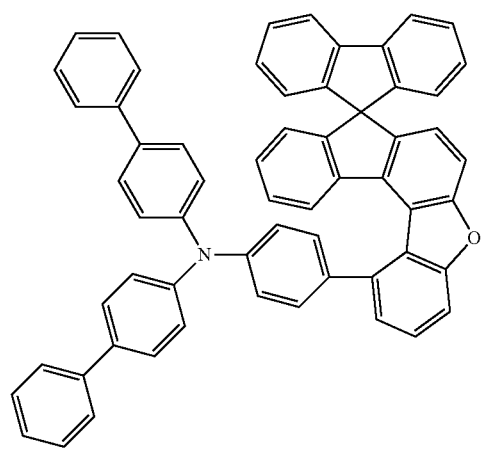
125
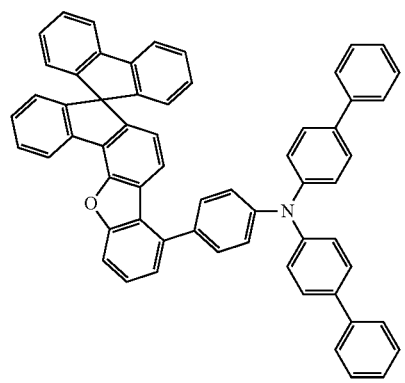
126
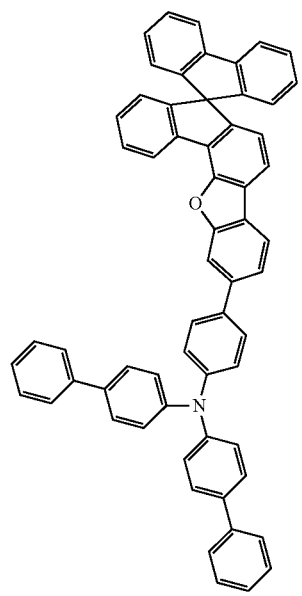

-continued
| 127 | 128 |
|---|---|
| 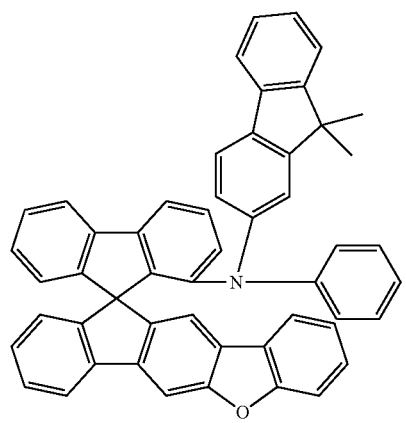 | 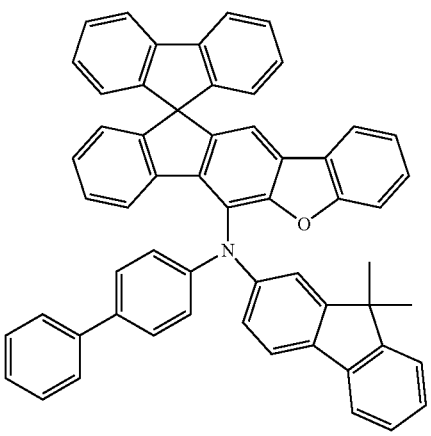 |
| 129 | 130 |
|---|---|
| 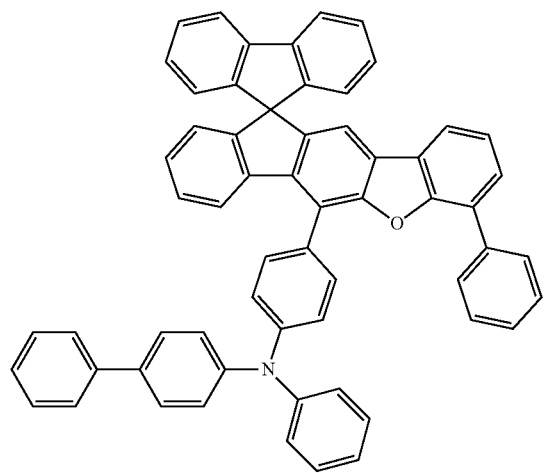 | 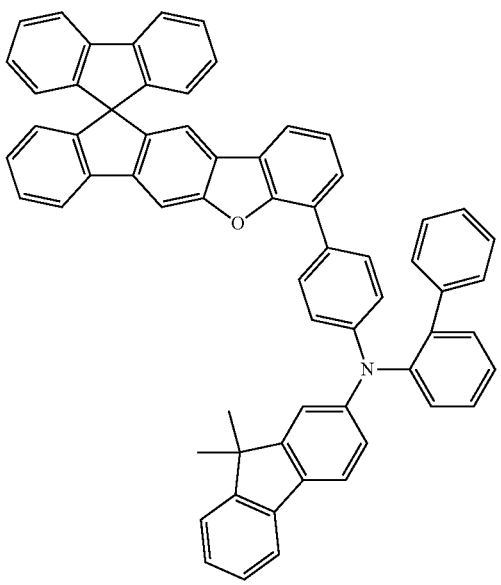 |
| 131 | 132 |
|---|---|
| 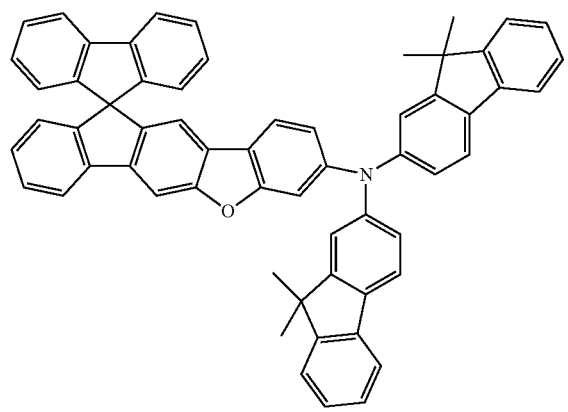 | 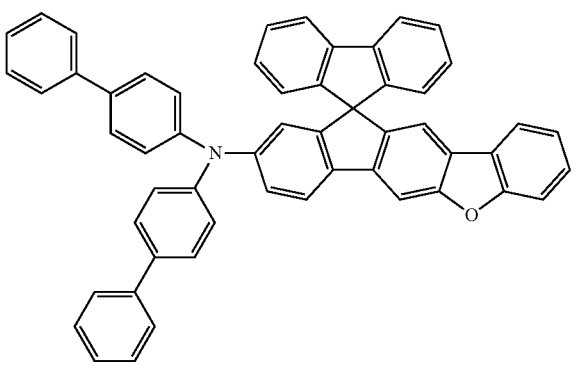 |

-continued
133
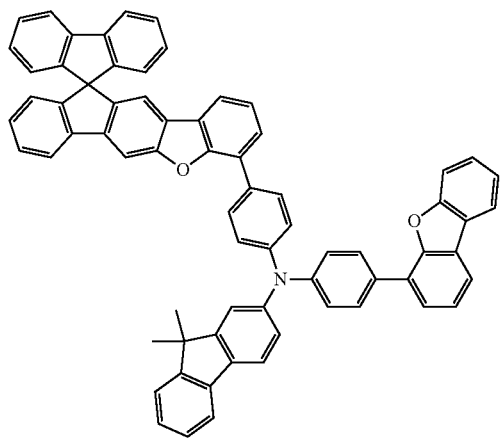
134
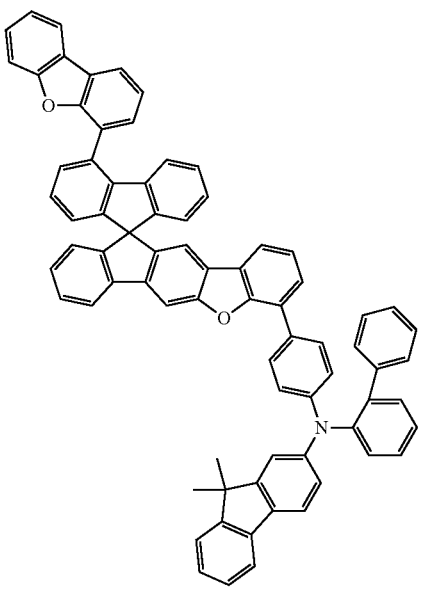
135
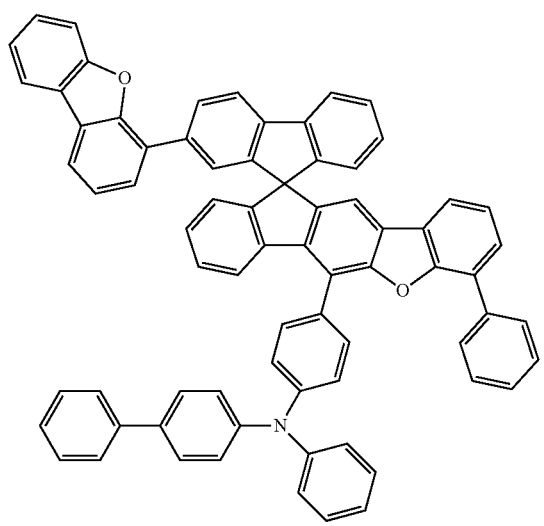
136
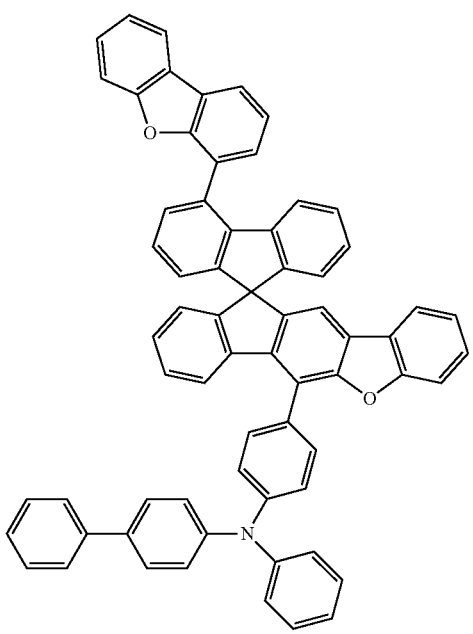

137
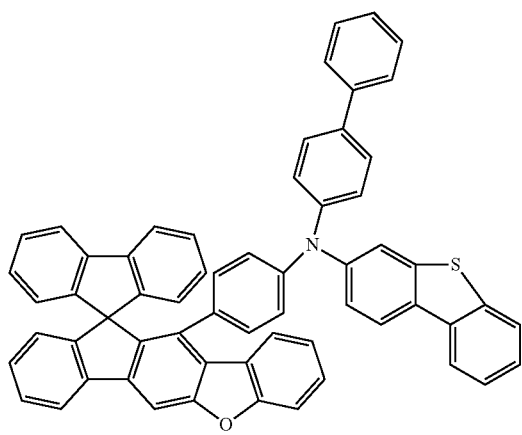
138
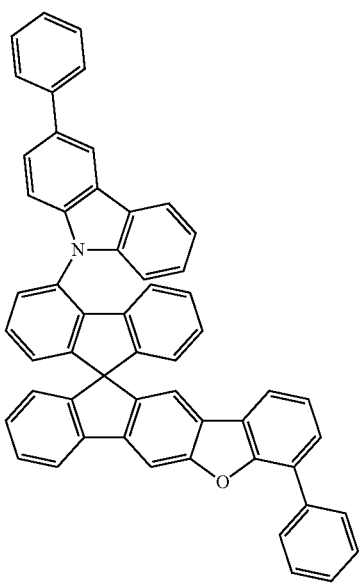
139
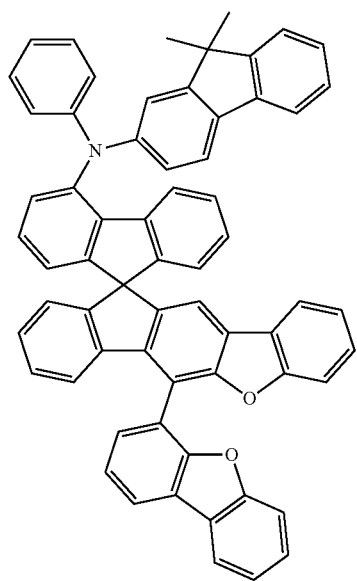
140
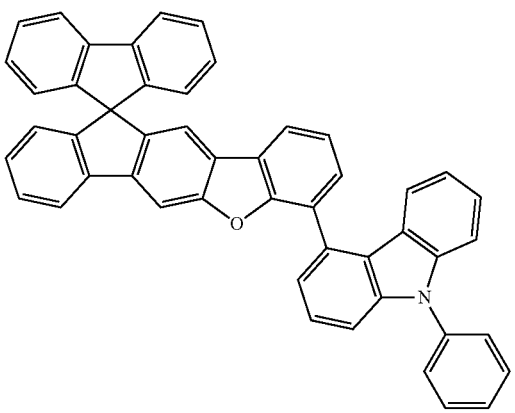

-continued
| 141 | 142 |
|---|---|
| 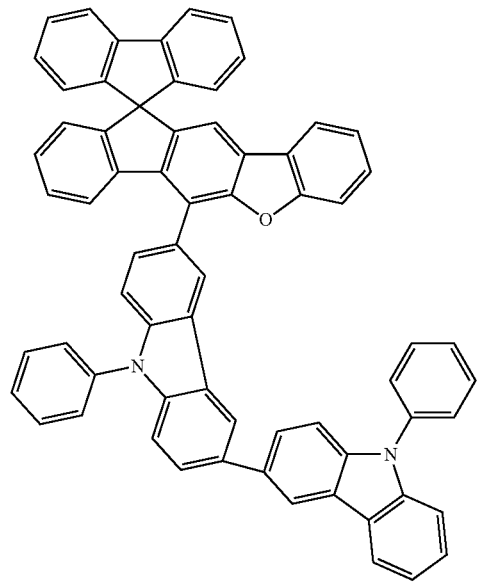 | 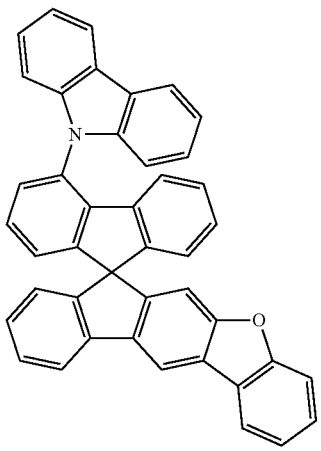 |
| 143 | 144 |
| 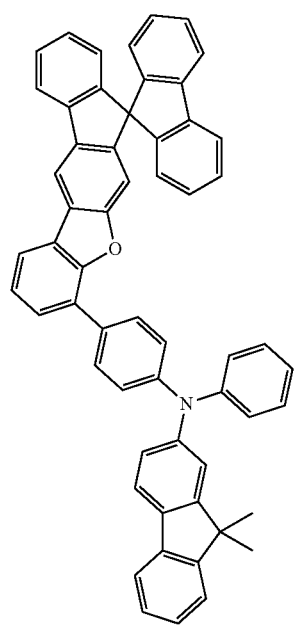 | 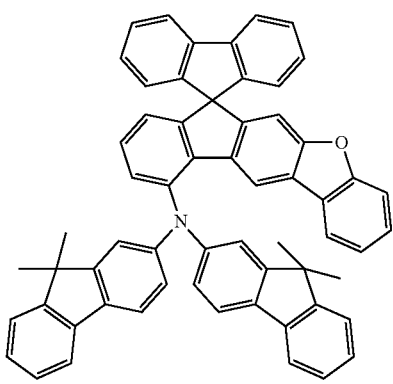 |

-continued
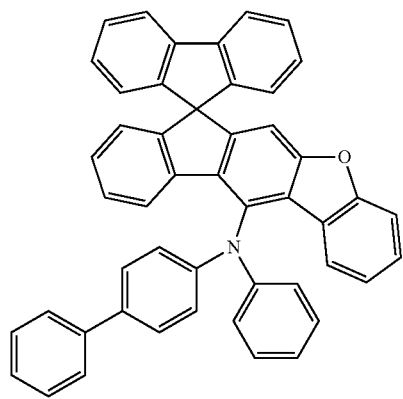
145
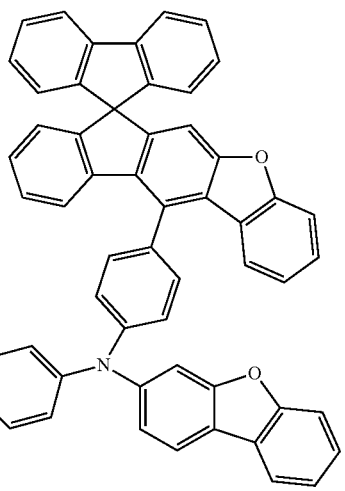
146
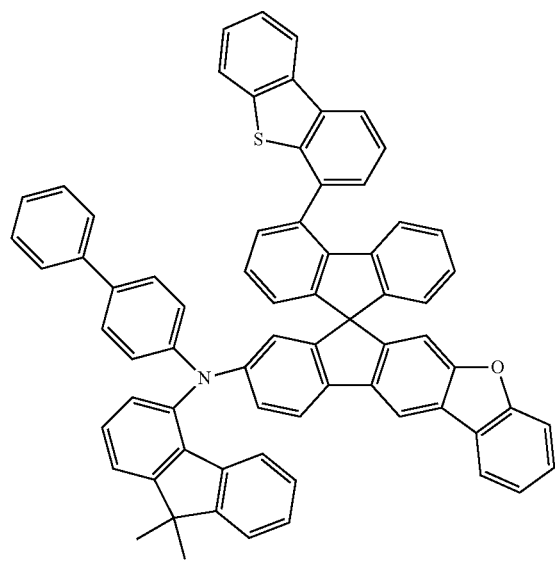
147
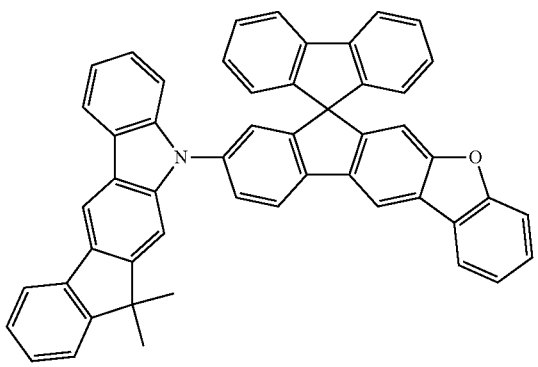
148

-continued
149
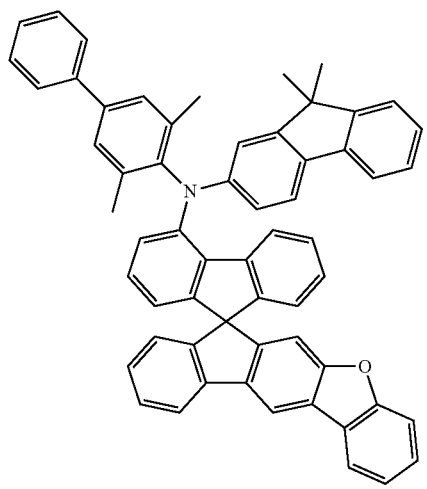
150
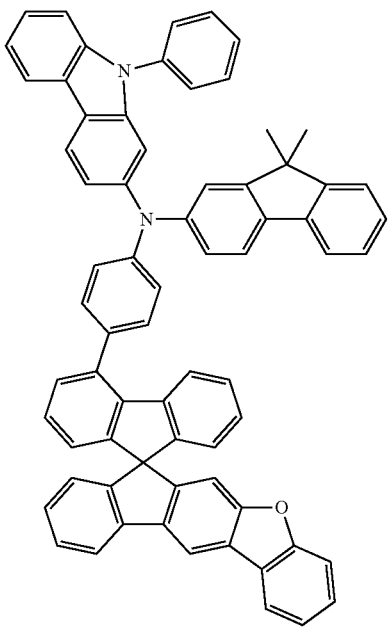
151
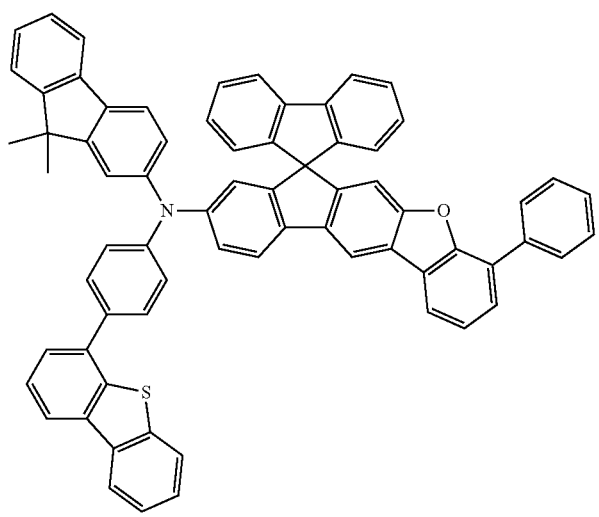
152
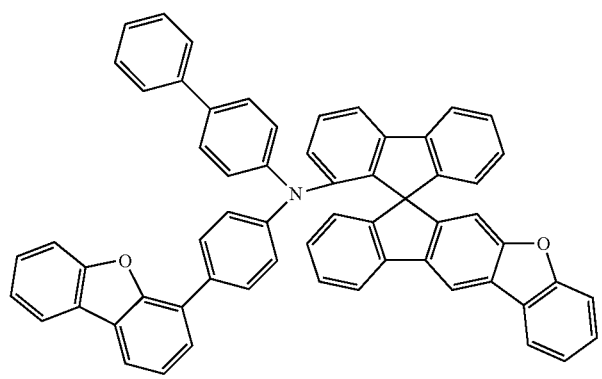
153
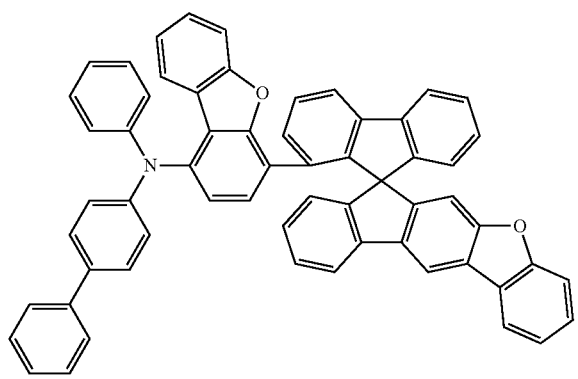
154
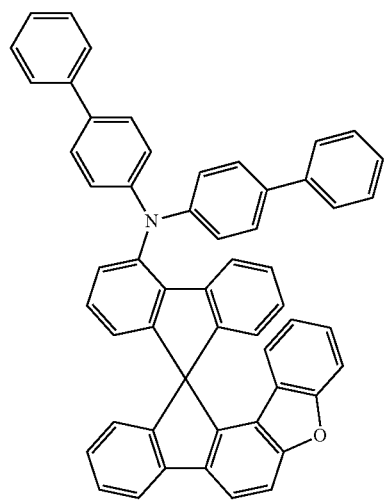

-continued
155
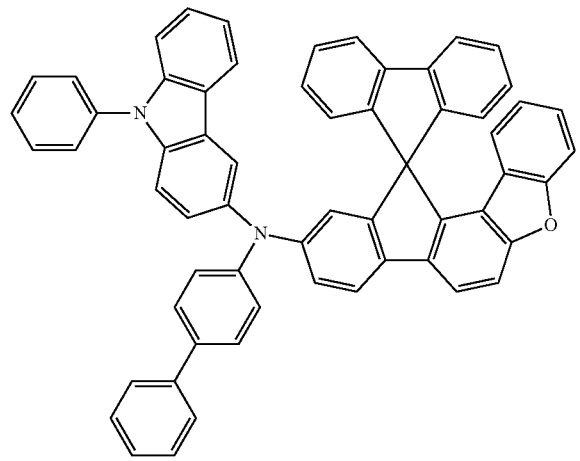
156
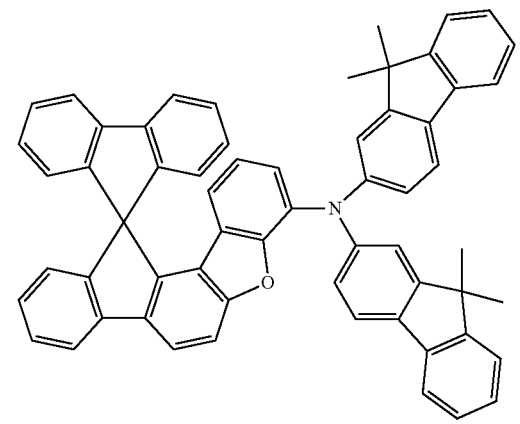
157
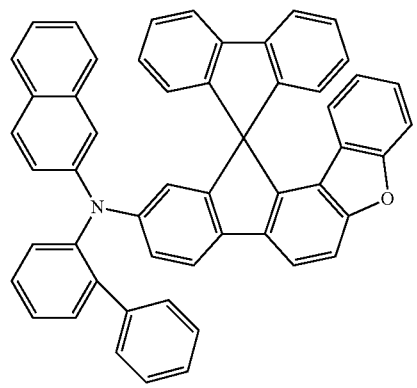
158
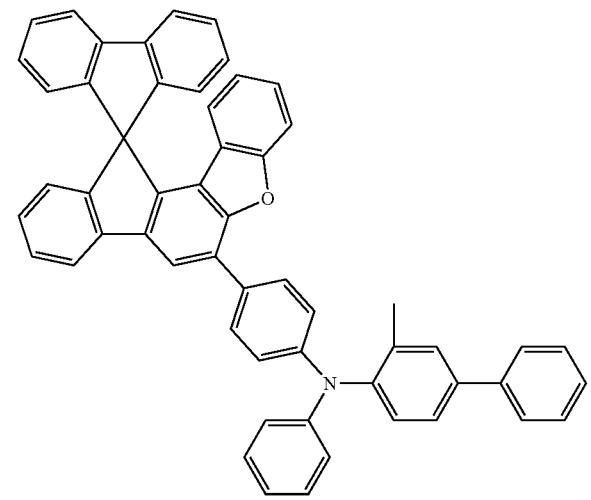
159
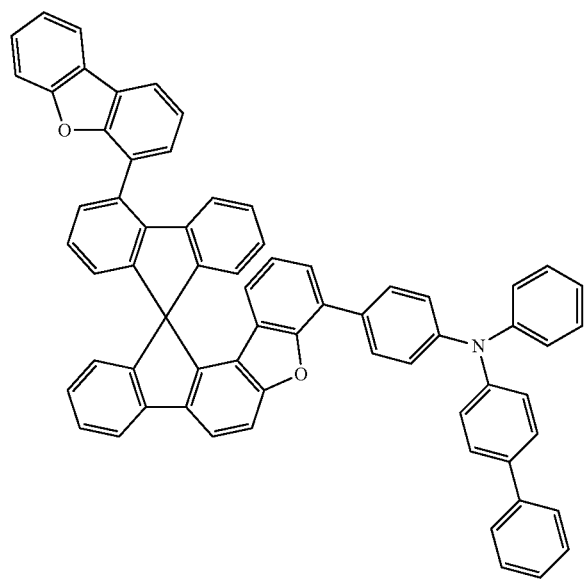
160
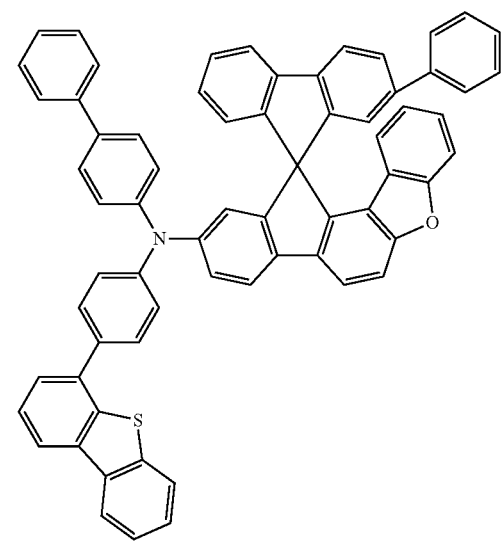

-continued
161
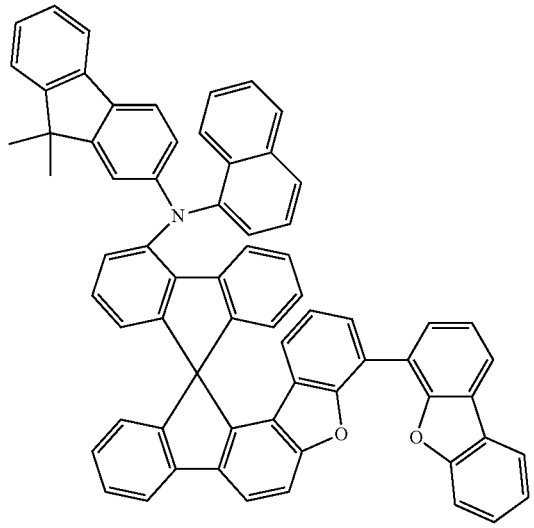
162
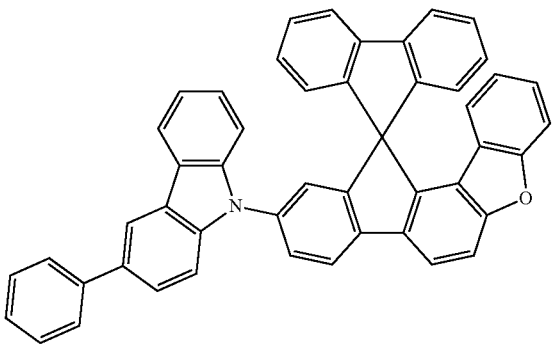
163
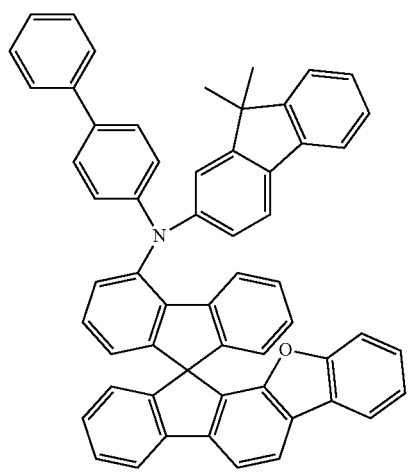
164
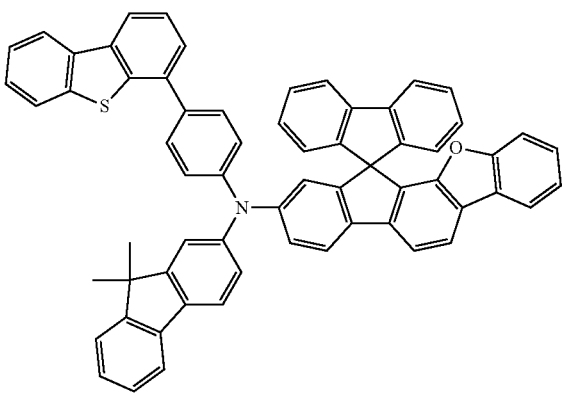
165
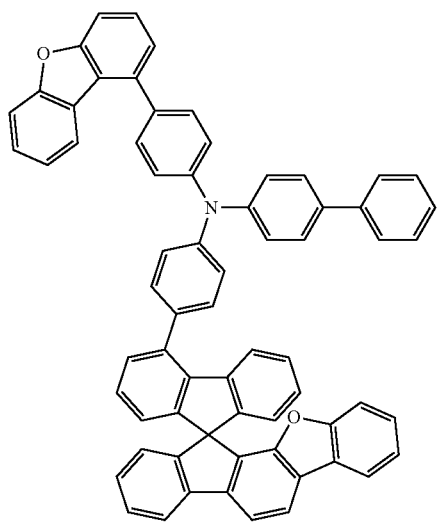
166

-continued
167
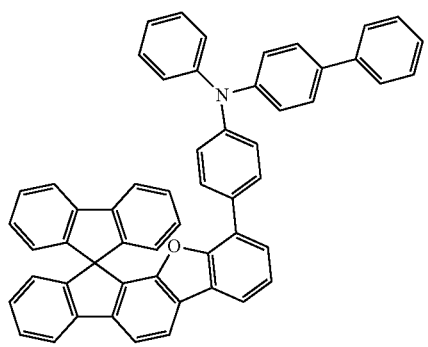
168
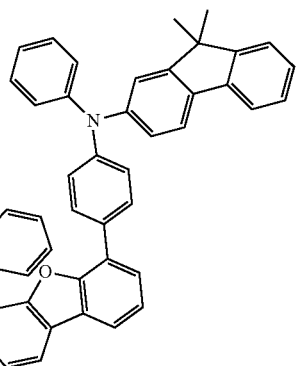
169
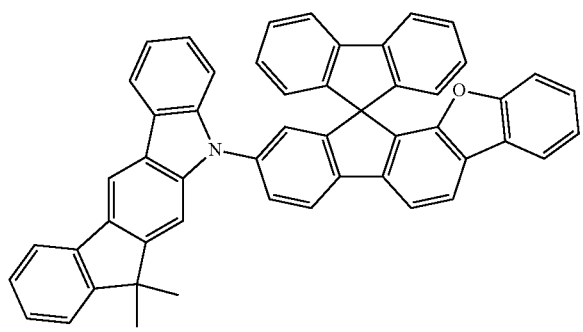
170
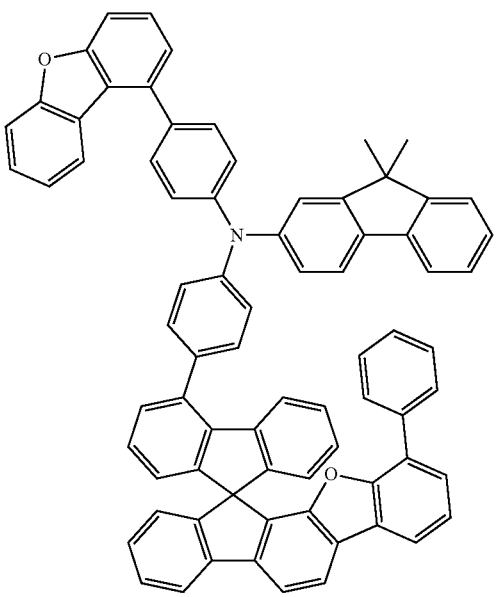
171
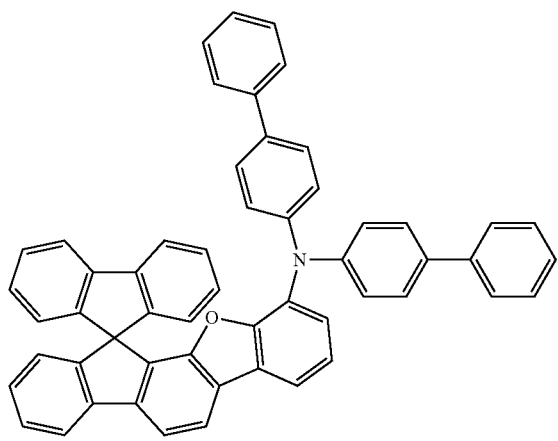

The compounds of the formula (I) can be synthesised by processes and reaction types known from the prior art, for example halogenation, organometallic addition, Buchwald coupling and Suzuki coupling.

Schemes 1 to 10 show possible synthetic routes for the preparation of the compounds according to the invention. They serve to explain the invention to the person skilled in the art and should not be interpreted as being restrictive. The person skilled in the art will be able to modify the synthetic routes shown within the bounds of his general expert knowledge, or develop completely different routes, if this appears more advantageous.

Schemes 1 to 8 show processes for the preparation of compounds of the formulae (II-1) to (II-6), which represent intermediates in the preparation of compounds of the formula (I).

Compounds of the formulae (II-1) to (II-6) have the following structures:

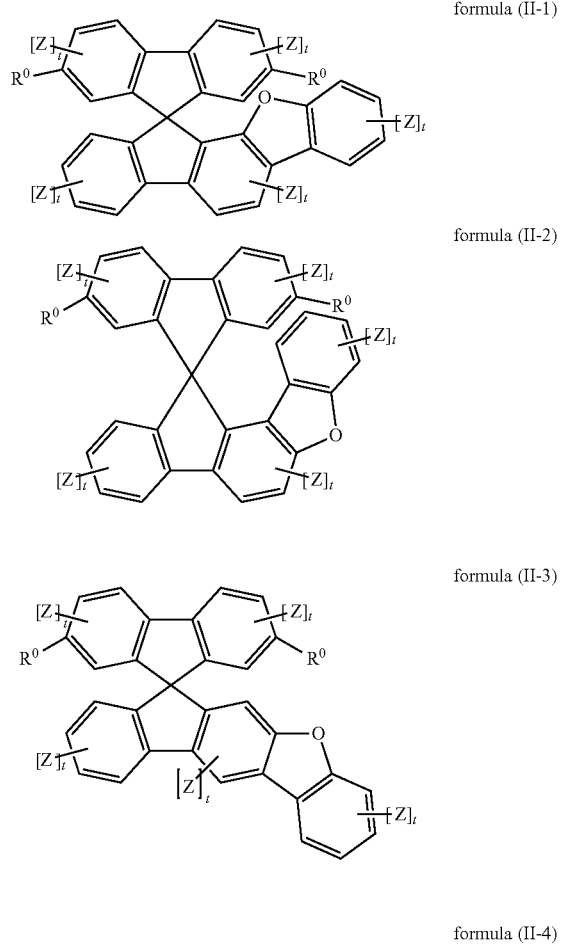

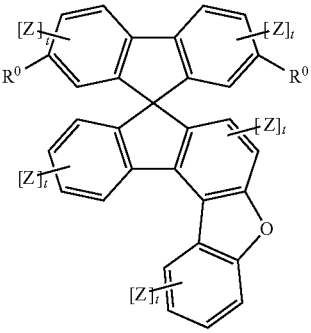

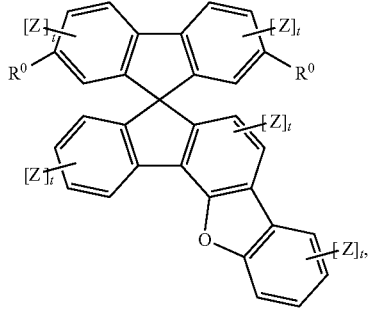

each of which may be substituted at one or more free positions by a radical $R^1$, which is as defined above, and where $R^0$ is as defined above and the other variables are defined as follows:

Z is selected on each occurrence, identically or differently, from F, Cl, Br, I, $B(OR^3)_2$, $OSO_2R^3$, $S(=O)R^3$ and $S(=O)_2R^3$;

t is on each occurrence, identically or differently, 0 or 1, where at least one index t per formula is equal to 1.

For the compounds of the formulae (II-1) to (II-6), the definitions of the radicals $R^0$ and $R^1$ to $R^3$ indicated above for formula (I) are likewise regarded as preferred.

For formulae (II-1) to (II-6), it is preferred for precisely one or precisely two indices t to be equal to 1.

For formulae (II-1) to (II-6), it is preferred for Z to be selected on each occurrence, identically or differently, from Cl, Br, I and $B(OR^3)_2$.

Of the formulae (II-1) to (II-6), preference is given to the formulae (II-5) and (II-6).

The intermediates of the formulae (II-1) to (II-6) are novel and as such are a subject-matter of the present application.

In all the following synthesis schemes, the compounds are shown unsubstituted. This does not exclude the presence of any desired substituents in the processes.

Scheme 1 shows a suitable synthesis for the intermediate of the formula (II-6).

Scheme 1

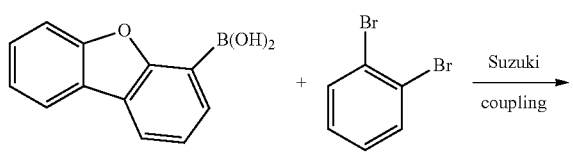

107
-continued
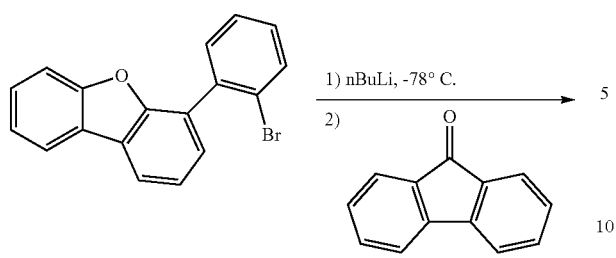
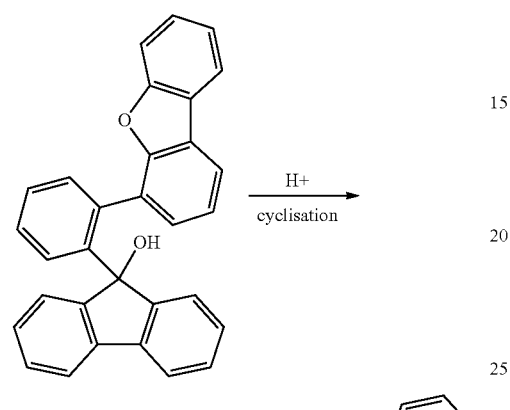
Scheme 2 shows a suitable synthesis for the intermediate of the formula (II-5).
Scheme 2
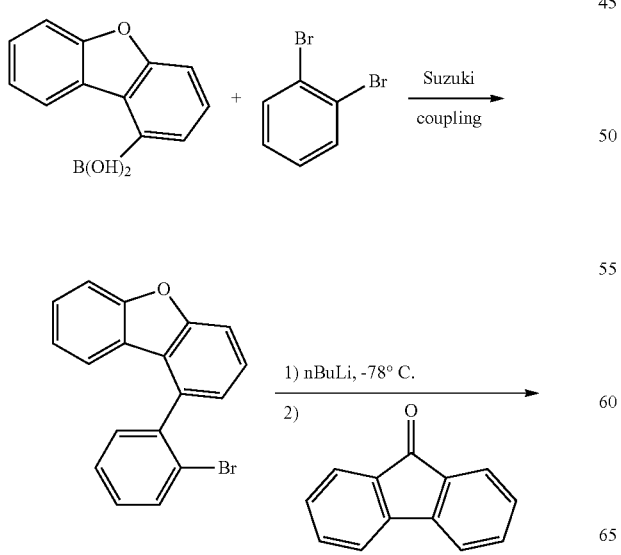
108
-continued
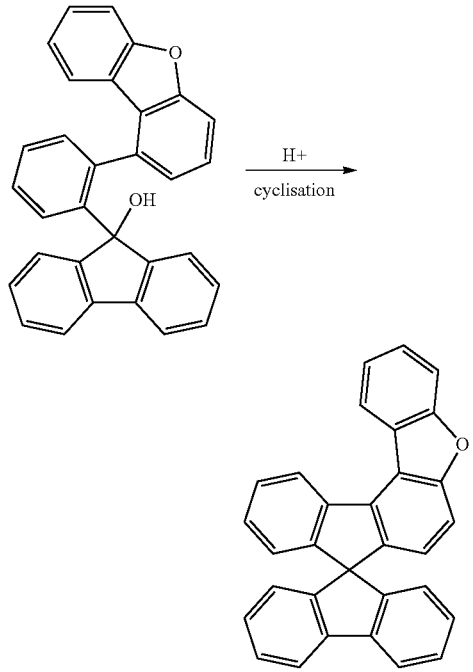
Scheme 3 shows a suitable synthesis for the intermediate of the formula (II-4).
Scheme 3
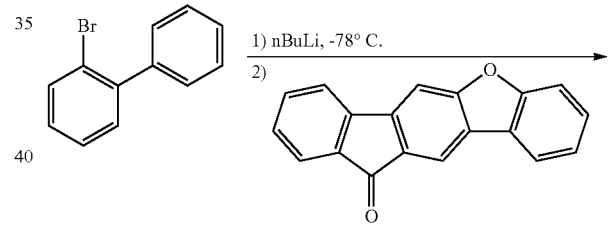
[121073-95-8]
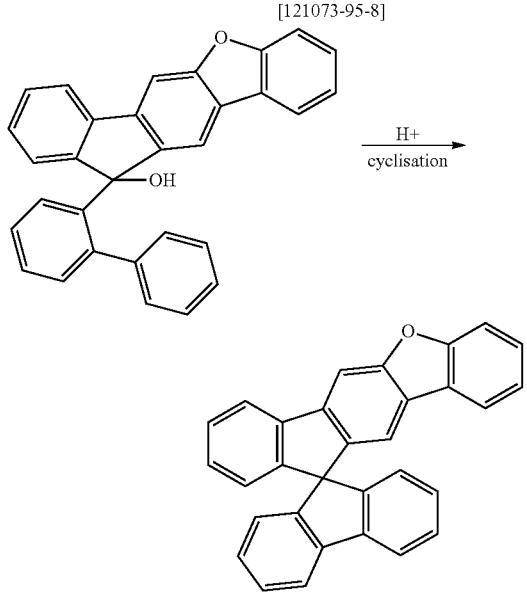

Scheme 4 shows a suitable synthesis for the intermediate of the formula (II-3).
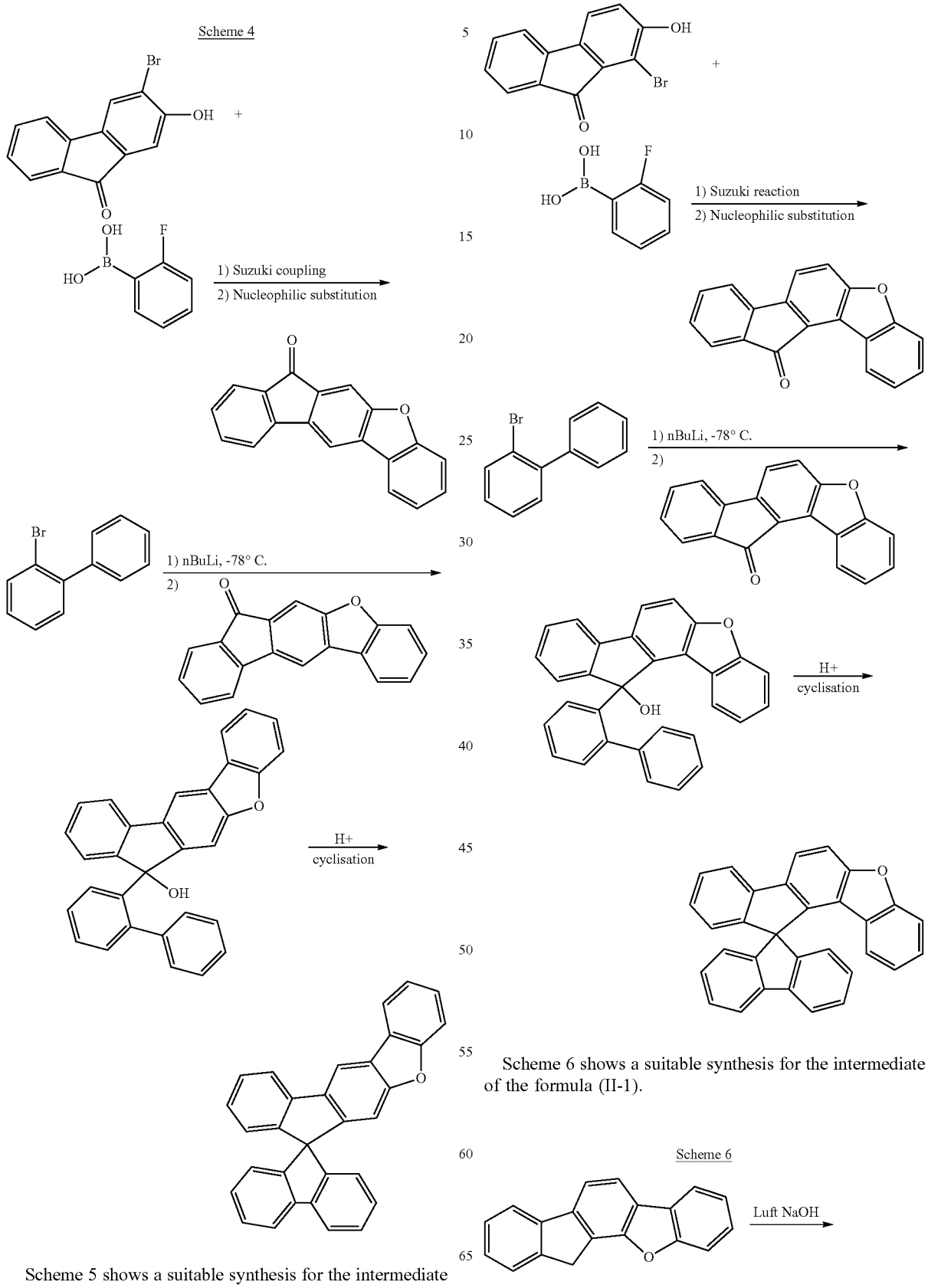
Scheme 5 shows a suitable synthesis for the intermediate of the formula (II-2).
Scheme 6 shows a suitable synthesis for the intermediate of the formula (II-1).

111
-continued
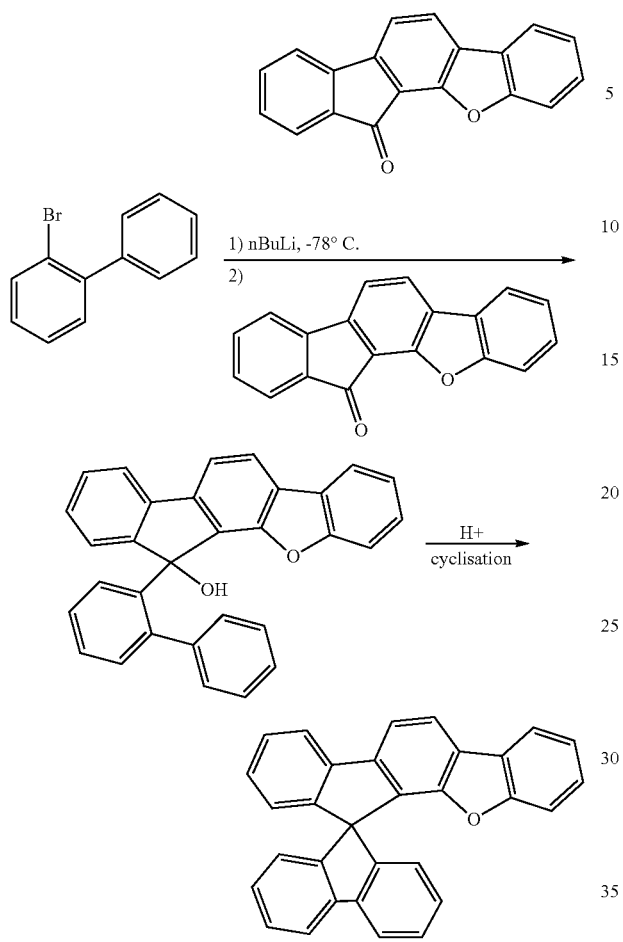
Scheme 7 shows a suitable alternative synthesis for intermediates of the formulae (II-1) and (II-4).
Scheme 7
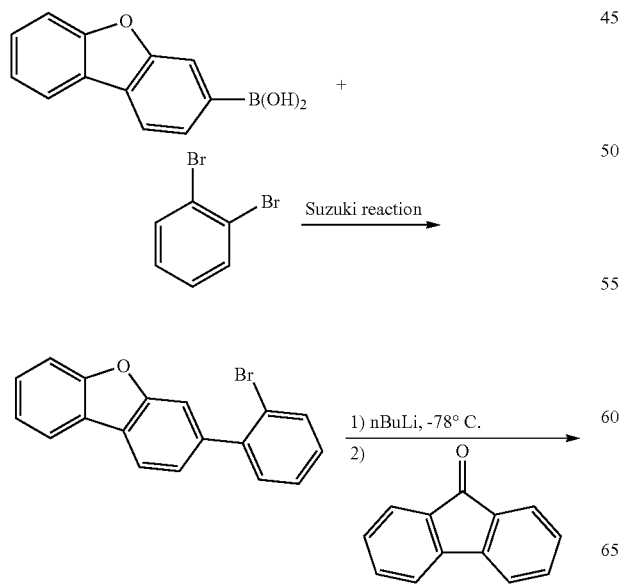
112
-continued
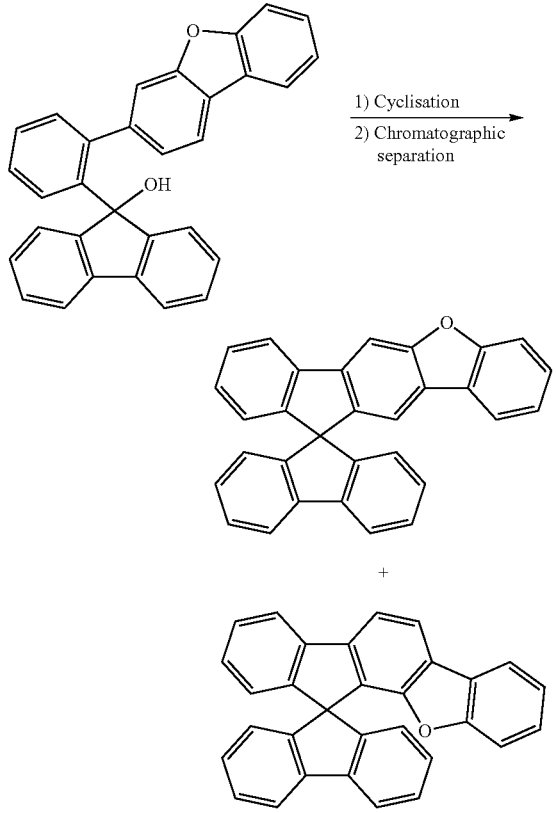
Scheme 8 shows a suitable alternative synthesis for intermediates of the formulae (II-2) and (II-3).
Scheme 8
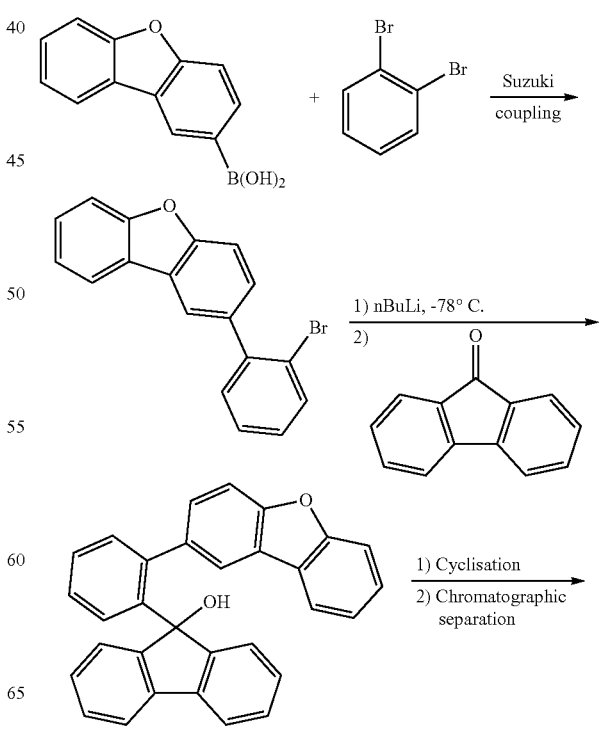

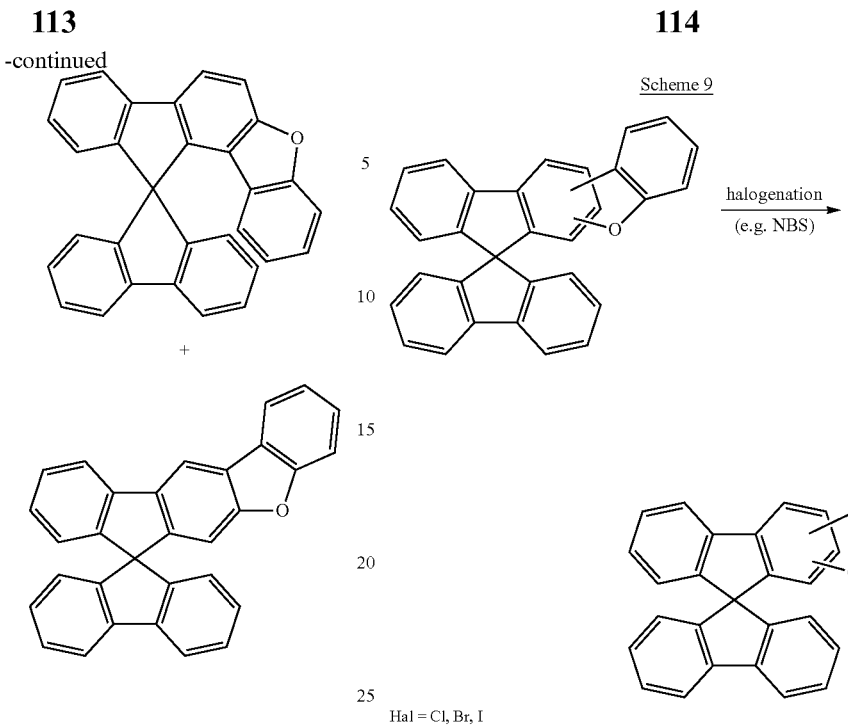

Hal = Cl, Br, I

The building blocks shown above can be provided with a reactive group, such as, for example, halogen, on the benzofluorene unit, as shown by the following scheme:

The intermediates of the formulae (II-1) to (II-6) provided with reactive groups Z are versatile building blocks which can be converted into compounds of the formula (I), as shown by the following scheme:

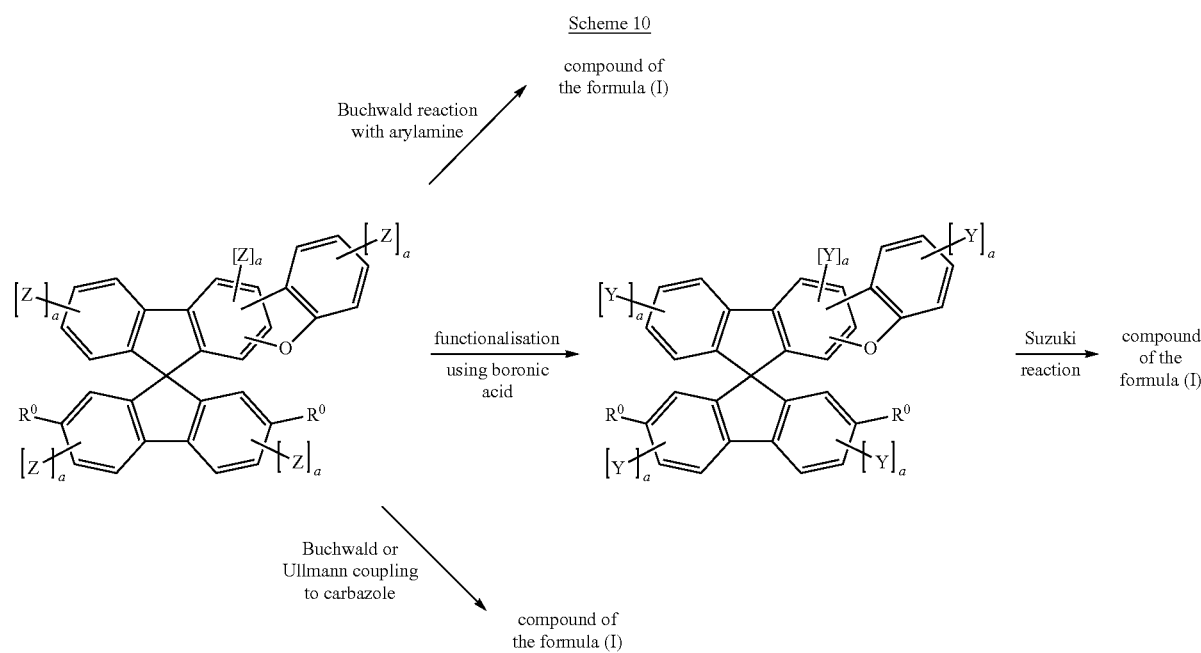

Z = halogen or other reactive functional group
Y = boronic acid
a = 0 or 1

The present application therefore also relates to a process for the preparation of compounds of the formula (I), characterised in that firstly the spirobifluorene basic structure is prepared, and, in a later step, an arylamino or carbazole group or an aryl or heteroaryl group which is substituted by an arylamino or carbazole group is introduced via an organometallic coupling reaction.

The organometallic coupling reaction here is preferably a Buchwald coupling or a Suzuki coupling.

The compounds described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer may be localised at any desired positions in formula (I) which are substituted by $R^0$, $R^1$ or $R^2$. Depending on the linking of the compound of the formula (I) the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula ((I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). Depending on the substitution, the compounds are employed in different functions and layers.

The invention therefore furthermore relates to the use of the compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates, as already indicated above, to an electronic device comprising at least one compound of the formula (I). The electronic device here is preferably selected from the devices mentioned above.

It is particularly preferably an organic electroluminescent device (OLED) comprising anode, cathode and at least one emitting layer, characterised in that at least one organic layer, which may be an emitting layer, a hole-transport layer or another layer, comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably the following: anode/hole-injection layer/hole-transport layer/optionally further hole-transport layer/optionally electron-blocking layer/emitting layer/electron-transport layer/electron-injection layer/cathode.

However, not all the said layers have to be present, and further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention are preferably present in the hole-transport layer or the electron-blocking layer.

It should be noted that, for the generation of white light, an emitter compound used individually which emits in a broad wavelength range may also be suitable instead of a plurality of emitter compounds emitting in colour.

It is preferred in accordance with the invention for the compound of the formula (I) to be employed in an electronic device comprising one or more emitters. The compound may be present in various layers here, preferably in a hole-transport layer, an electron-blocking layer, a hole-injection layer or in an emitting layer.

The term phosphorescent emitters typically encompasses compounds in which the light emission takes place through a spin-forbidden transition, for example a transition from an excited triplet state or a state having a higher spin quantum number, for example a quintet state.

Suitable phosphorescent emitters (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent emitters.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (I) in organic electroluminescent devices. Further examples are shown in a following table.

However, the compound of the formula (I) can also be employed in accordance with the invention in an electronic device comprising one or more fluorescent emitters.

In a preferred embodiment of the invention, the compounds of the formula (I) are employed as hole-transport material. The compounds are then preferably employed in a hole-transport layer, an electron-blocking layer or a hole-injection layer.

A hole-transport layer in accordance with the present application is a layer having a hole-transporting function which is located between anode and emitting layer.

Hole-injection layers and electron-blocking layers in the sense of the present invention are taken to be specific embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. In accordance with the present invention, the p-dopants employed are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

Particularly preferred p-dopants are quinodimethane compounds, azaindenofluorenediones, azaphenalenes, azatriphenylenes, $I_2$, metal halides, preferably transition-metal halides, metal oxides, preferably metal oxides containing at least one transition metal or a metal from the 3rd main group, and transition-metal complexes, preferably complexes of Cu, Co, Ni, Pd and Pt with ligands containing at least one oxygen atom as bonding site. The dopants are furthermore preferably transition-metal oxides, preferably oxides of rhenium, molybdenum and tungsten, particularly preferably $Re_2O_7MoO_3$, $WO_3$ and $ReO_3$.

The p-dopants are preferably substantially uniformly distributed in the p-doped layers. This can be achieved, for example, by co-evaporation of the p-dopant and the hole-transport material matrix.

Preferred p-dopants are, in particular, the following compounds:

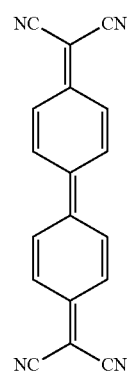
(D-1)

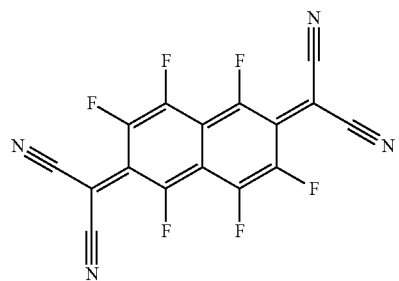
(D-2)

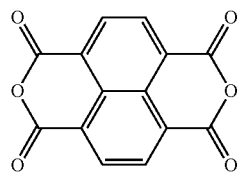
(D-3)

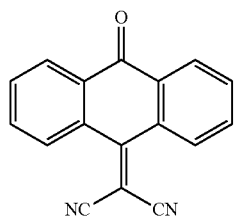
(D-4)

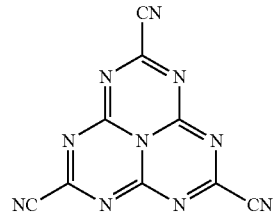
(D-5)

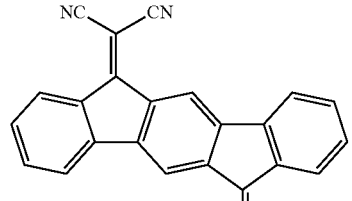
(D-6)

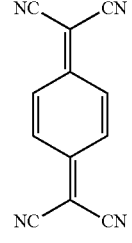
(D-7)

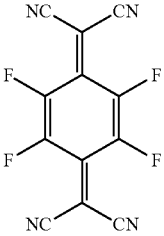
(D-8)

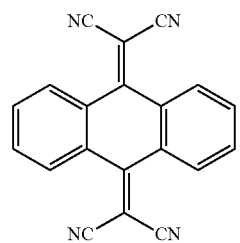
(D-9)

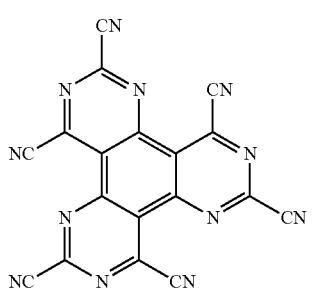
(D-10)

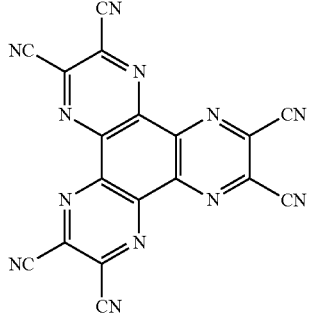
(D-11)

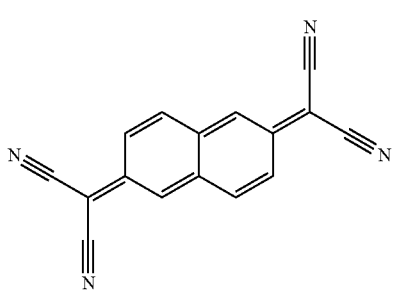
(D-12)

In a further preferred embodiment of the invention, the compound of the formula (I) is used as hole-transport material in combination with a hexaazatriphenylene derivative, as described in US 2007/0092755. The hexaazatriphenylene derivative here is particularly preferably employed in a separate layer.

In a further embodiment of the present invention, the compound of the formula (I) is employed as matrix material in combination with one or more emitters, preferably phosphorescent emitters.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the emitter is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of emitters. In this case too, the emitters are generally the compounds whose proportion in the system is the smaller and the matrix materials are the compounds whose proportion in the system is the greater. In individual cases, however, the proportion of an individual matrix material in the system may be smaller than the proportion of an individual emitter.

The compounds of the formula (I) are preferably used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. The compound of the formula (I) here is preferably the matrix material having hole-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1, Mixed-matrix systems are preferably employed in phosphorescent organic electroluminescent devices. More precise information on mixed-matrix systems is given, inter alia, in the application WO 2010/108579.

The mixed-matrix systems may comprise one or more emitters, preferably one or more phosphorescent emitters. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter is employed in the mixed-matrix system.

Preferred phosphorescent emitters for use in mixed-matrix systems are the phosphorescent emitters shown above.

According to a further preferred embodiment of the invention, the compound of the formula (I) can be employed as fluorescent emitter in an emitting layer. If the compound according to the invention is employed as fluorescent emitter in an emitting layer, it is preferably employed in combination with one or more matrix materials. Preferred matrix materials for use in combination with the compound of the formula (I) as emitter are indicated below.

Preferred embodiments of the various functional materials of the electronic device are shown below.

Preferred phosphorescent emitters are the above-mentioned compounds and the compounds shown in the following table:

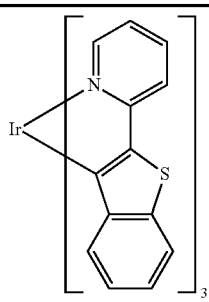

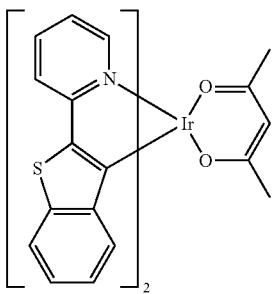
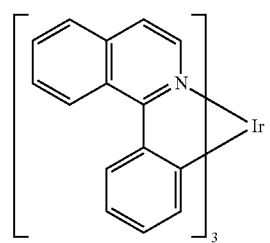
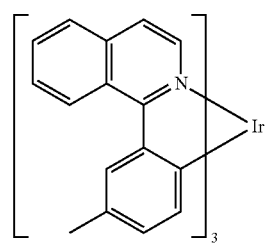
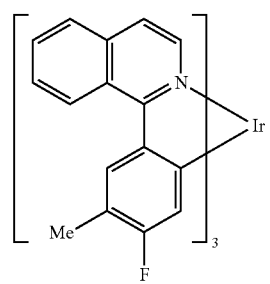
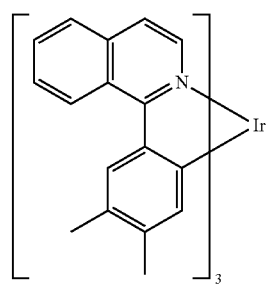
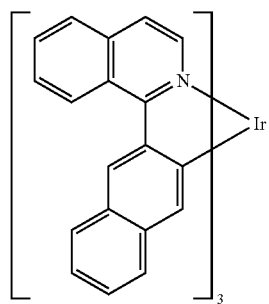
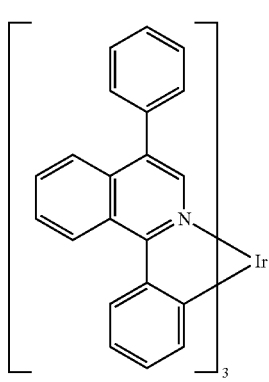
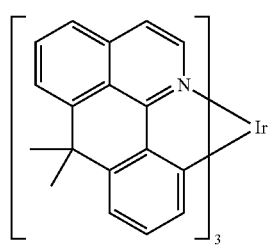
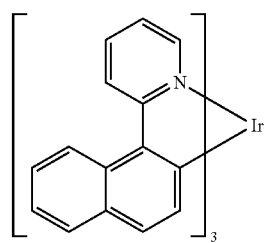
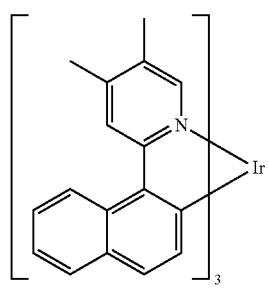

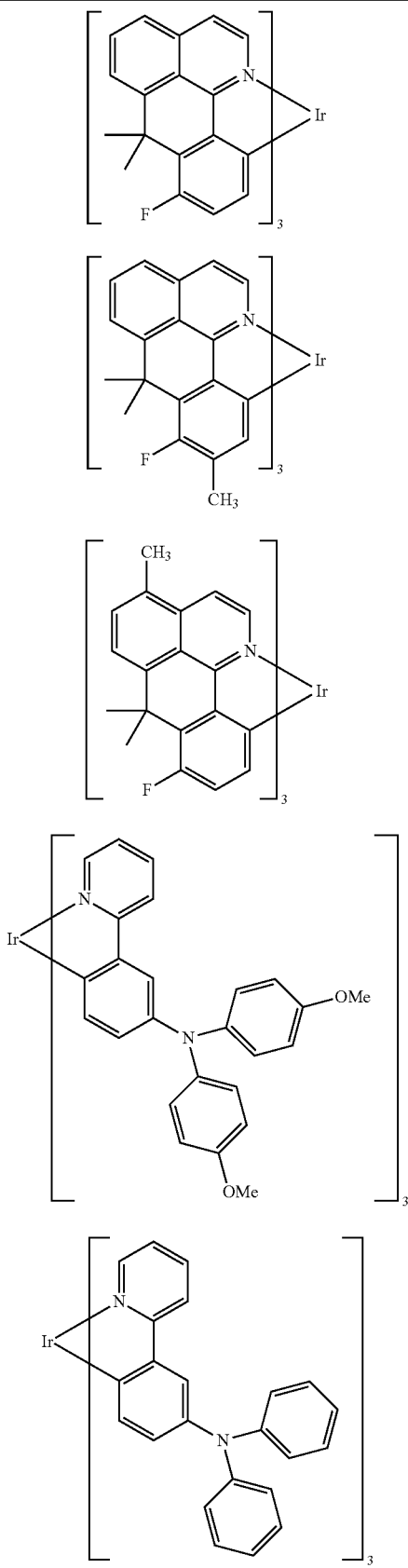
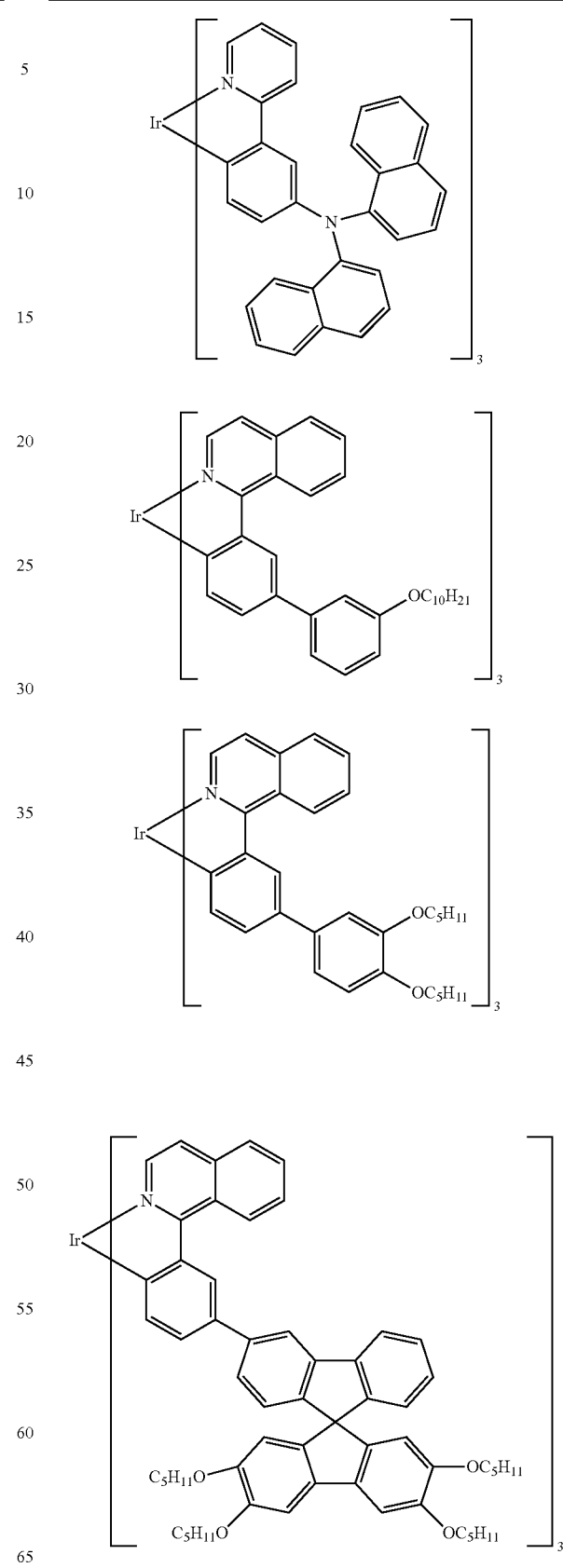

127
-continued
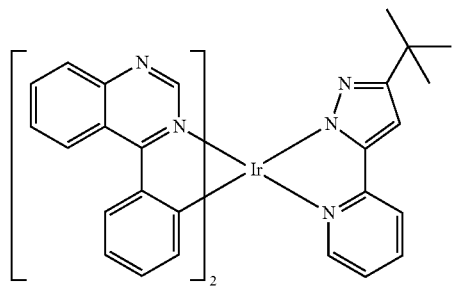
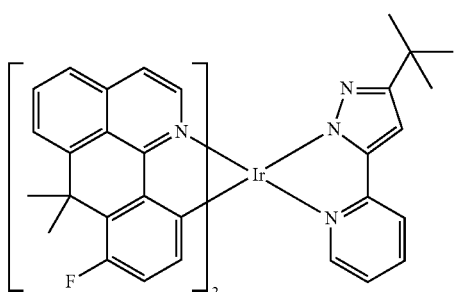
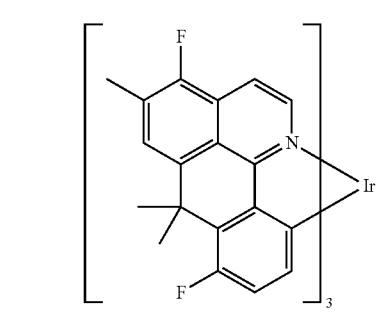
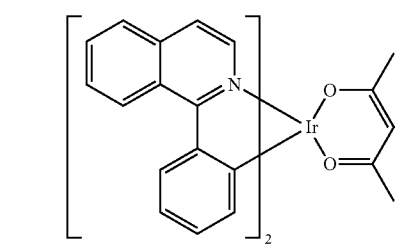
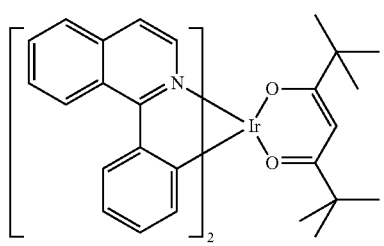
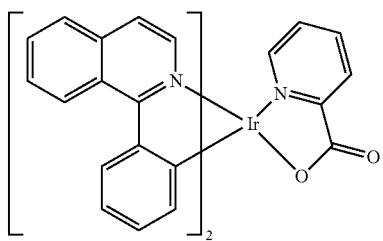
128
-continued
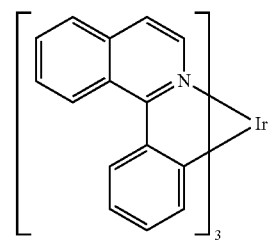
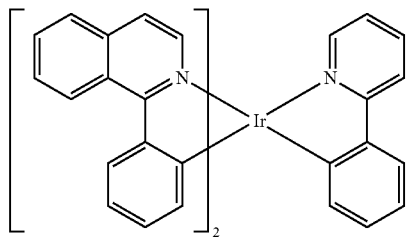
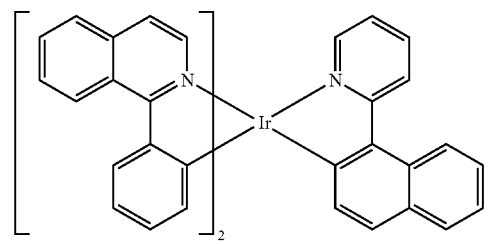
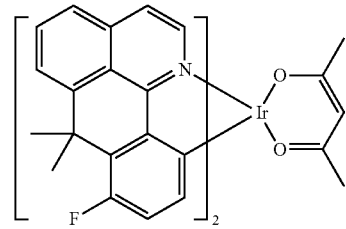
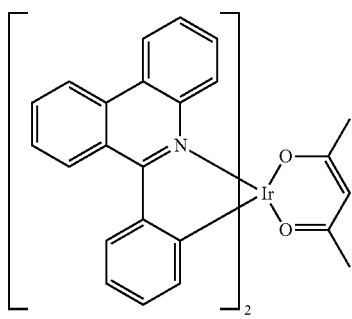
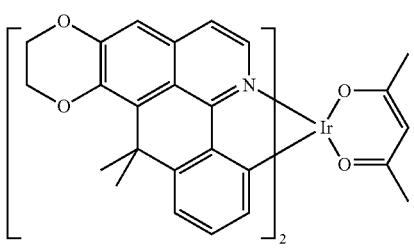

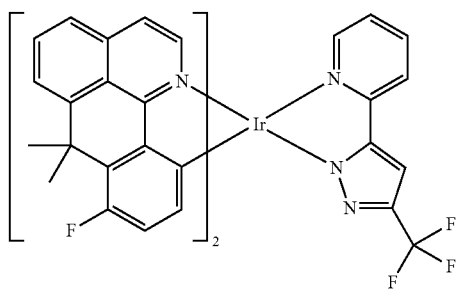
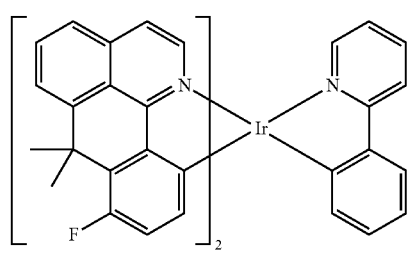
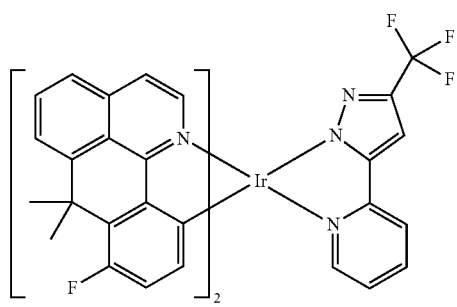
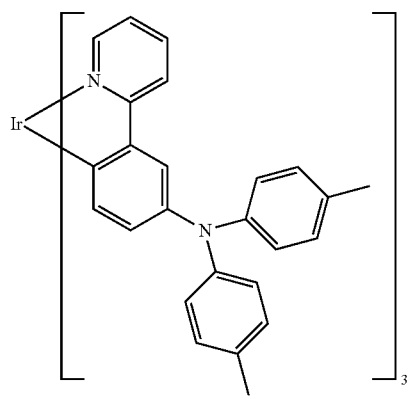
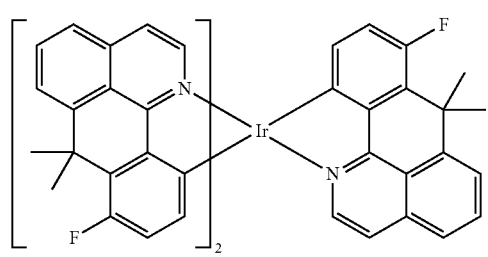
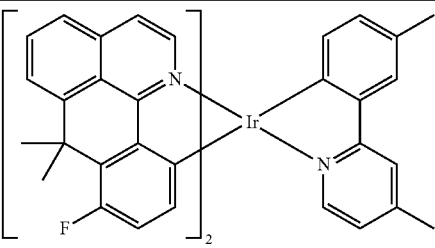
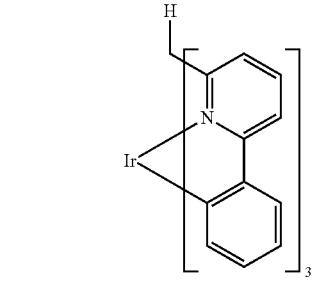
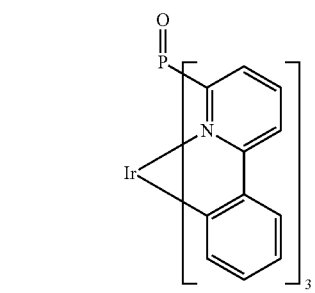
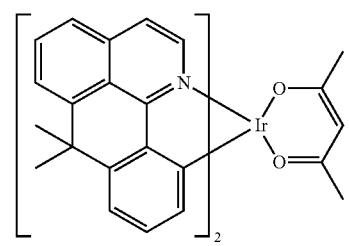
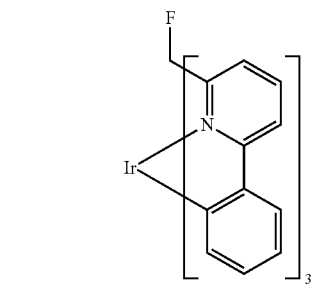
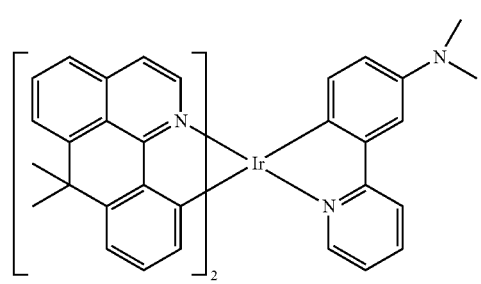

131
-continued
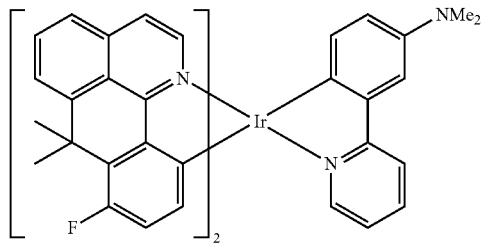
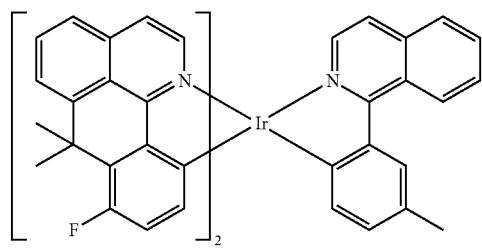
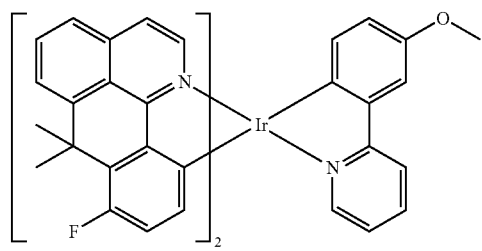
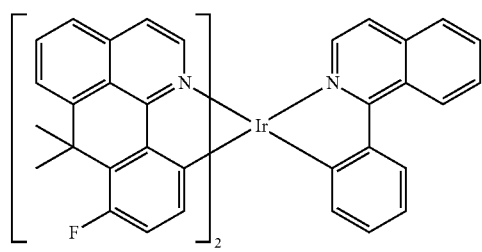
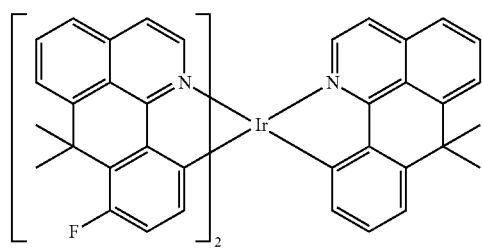
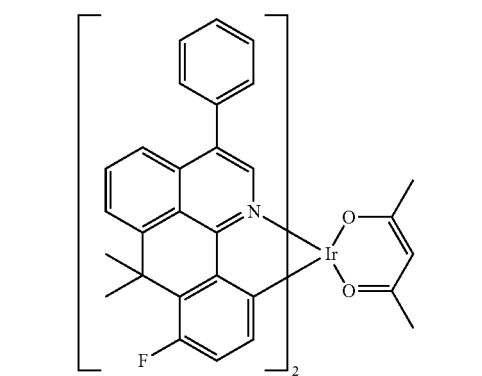
132
-continued
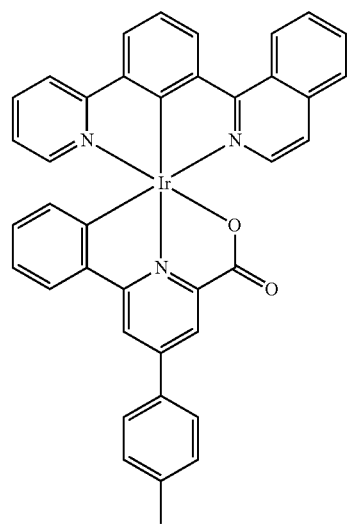
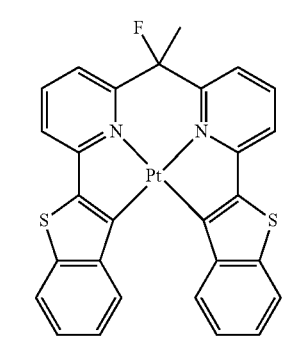
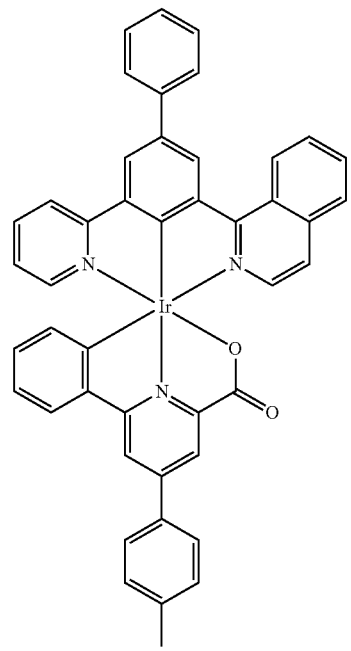

133
-continued
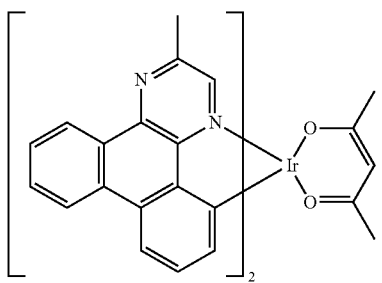
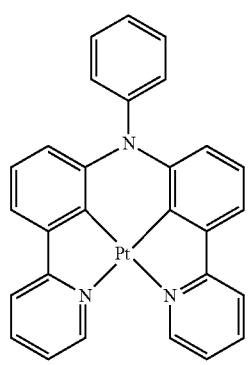
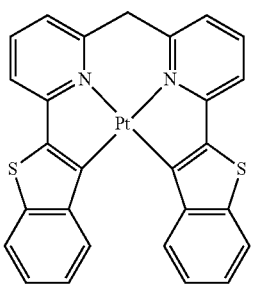
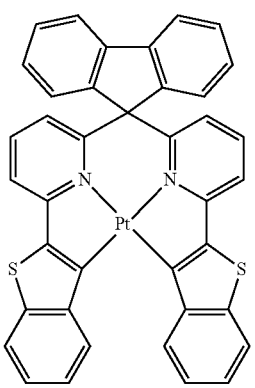
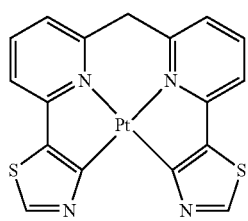
134
-continued
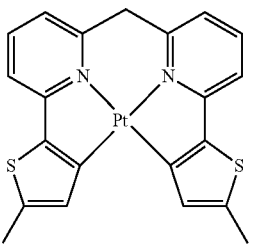
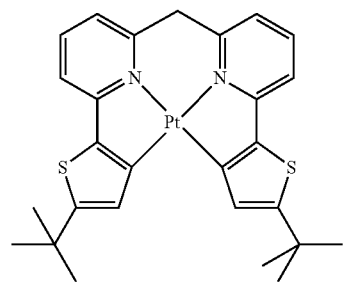
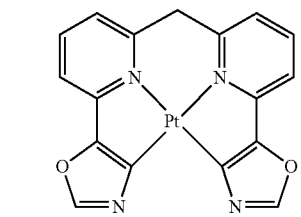
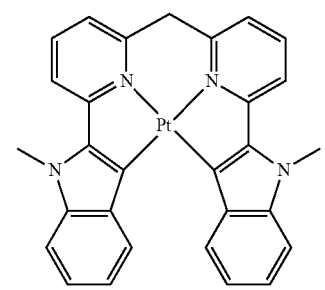
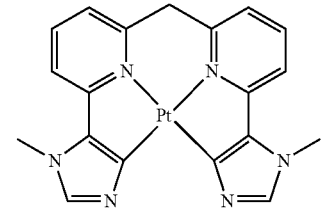

135
-continued
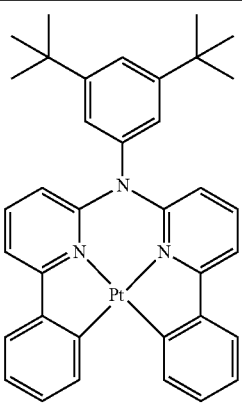
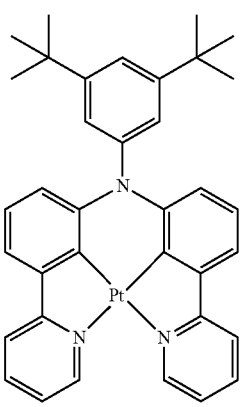
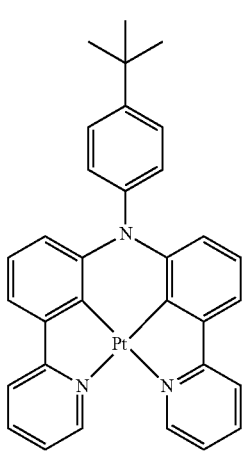
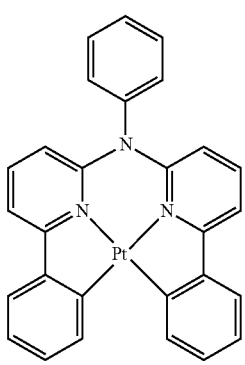
136
-continued
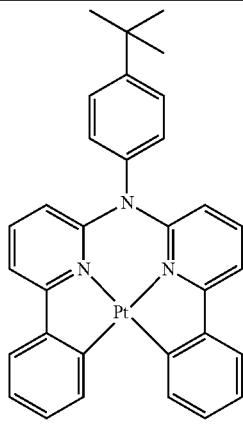
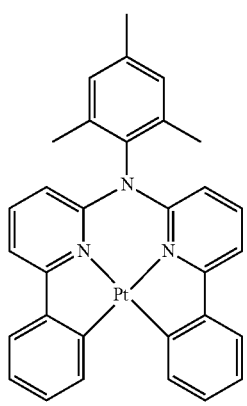
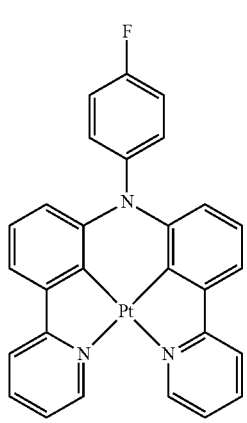
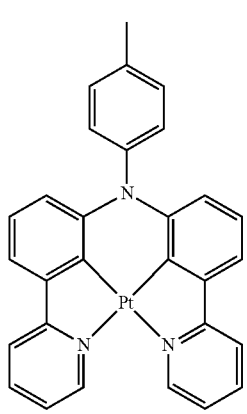

| 137 -continued | 138 -continued |
|---|---|
| 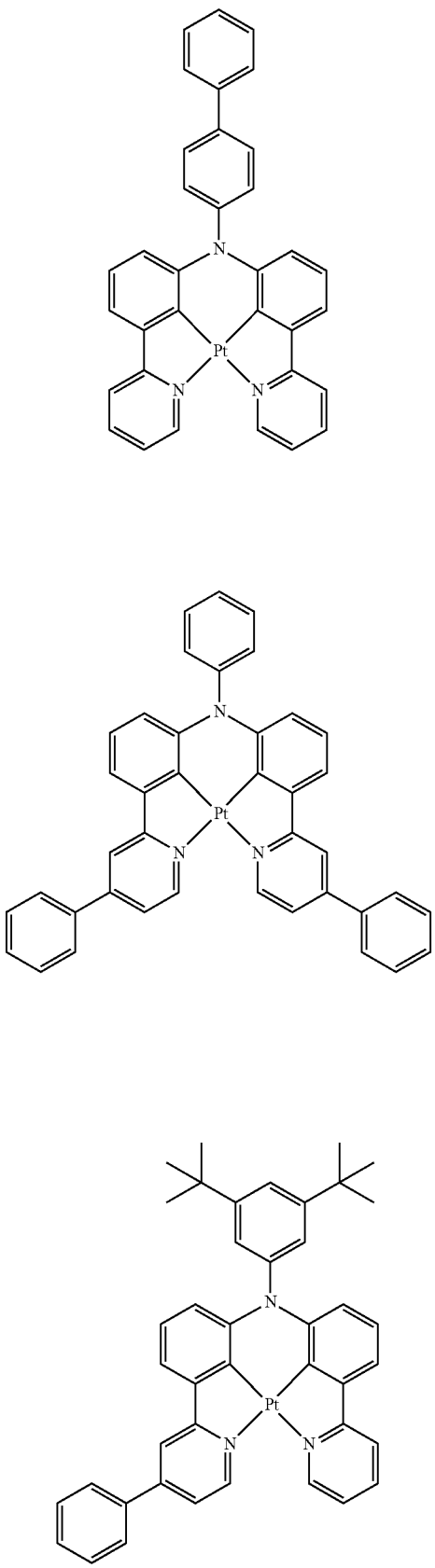 | 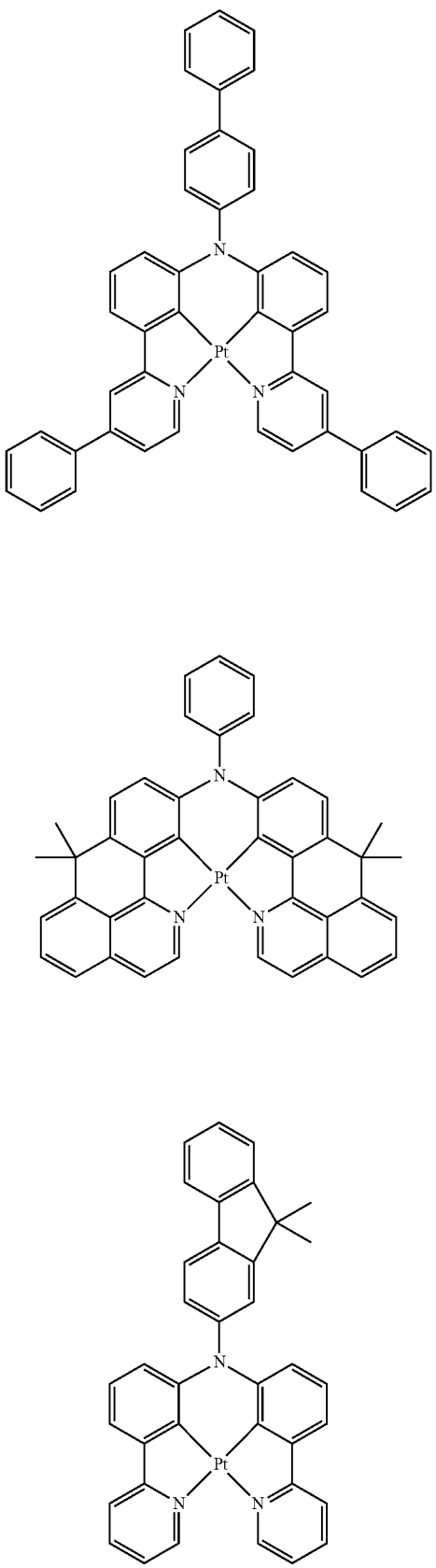 |

139
-continued
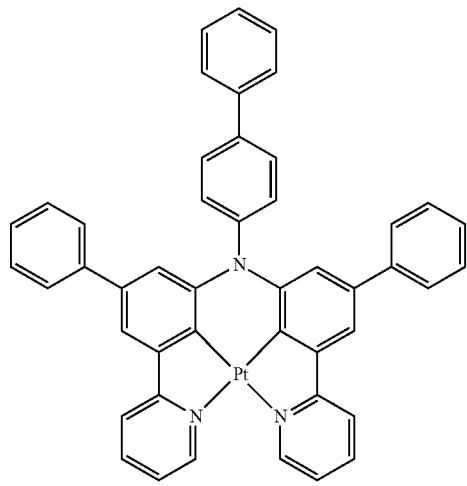
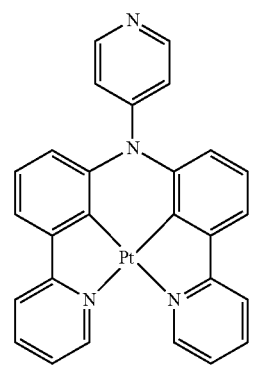
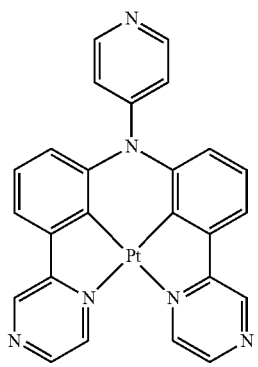
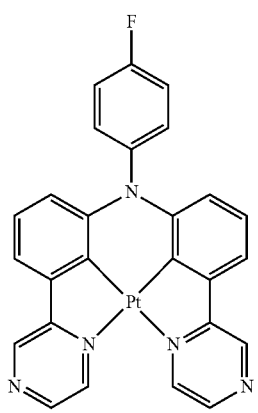
140
-continued
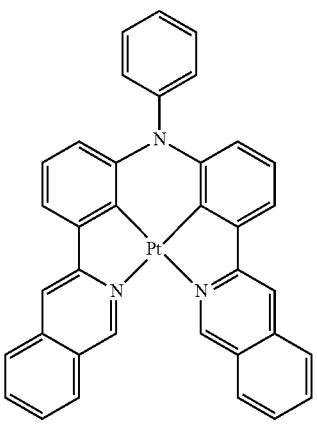
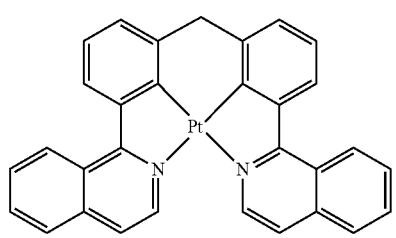
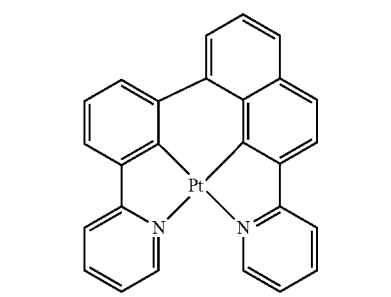
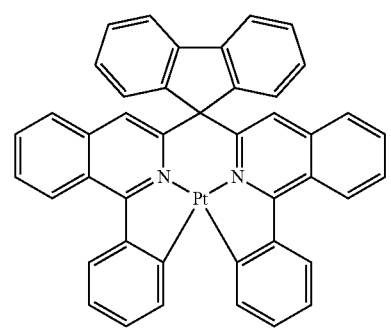
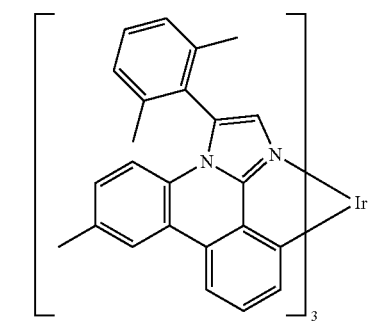

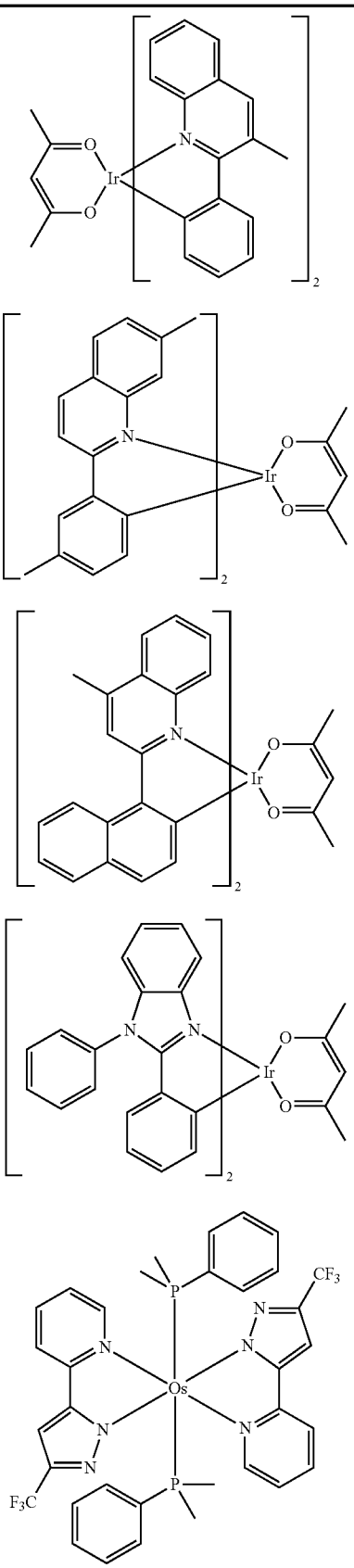

| 143 -continued | 144 -continued |
|---|---|
| 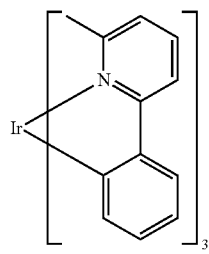 | 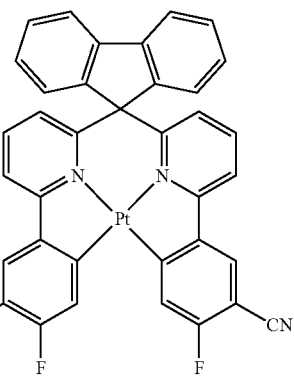 |
| 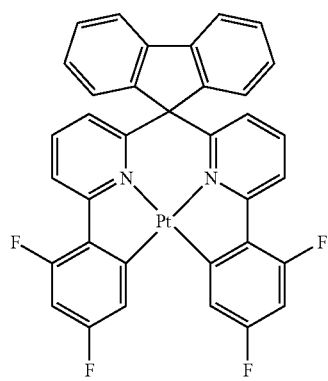 | 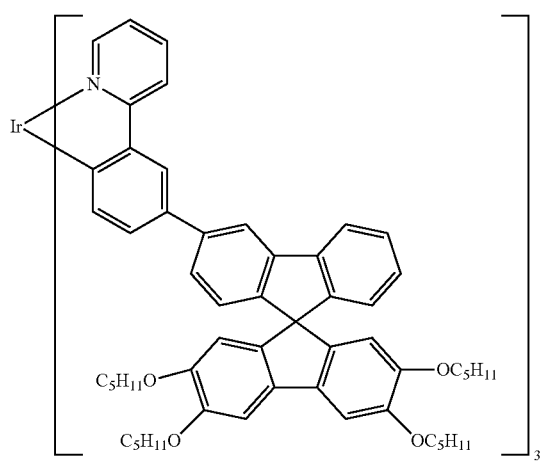 |
| 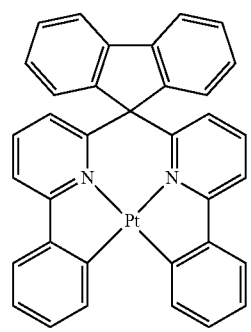 | 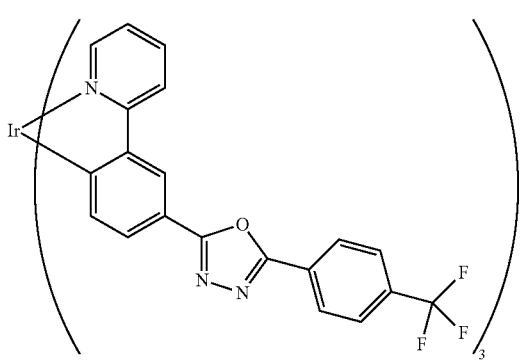 |
| 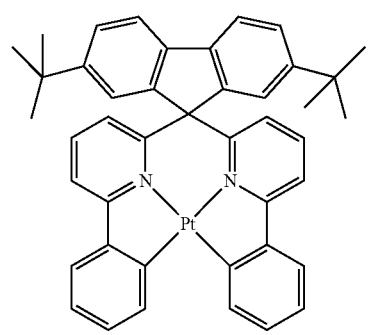 | 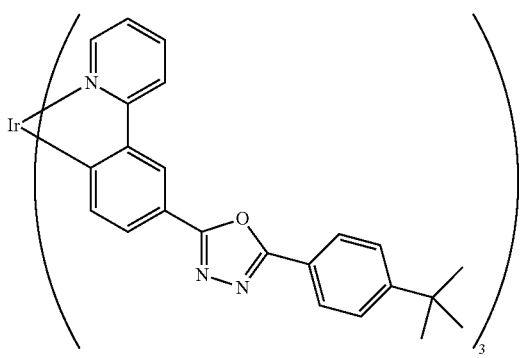 |

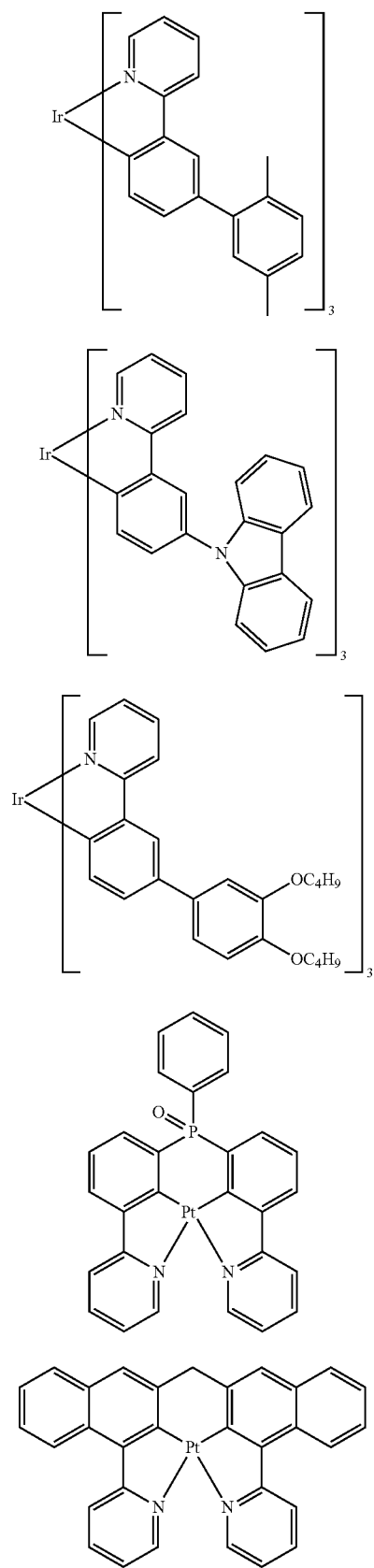
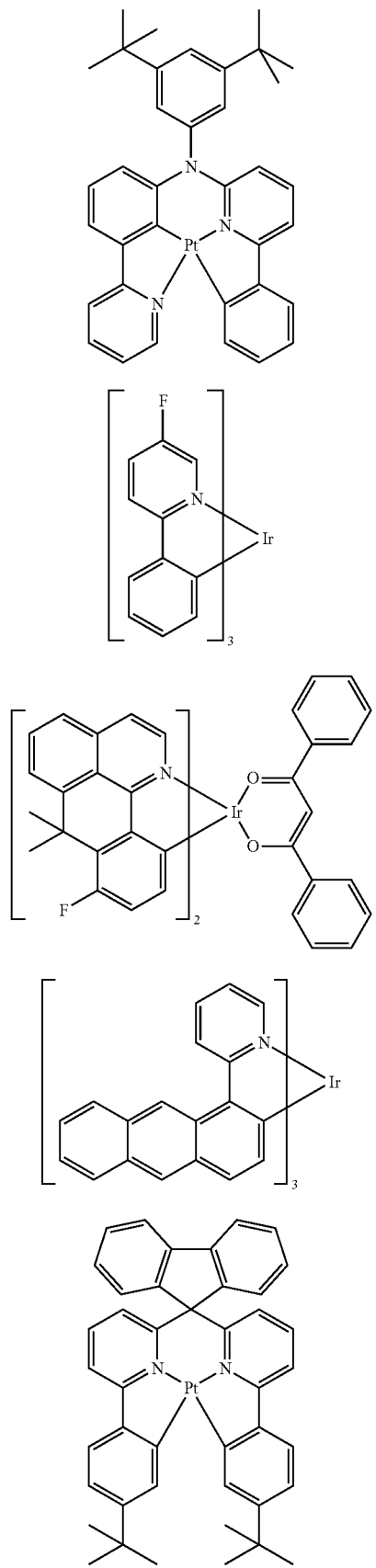

147
-continued
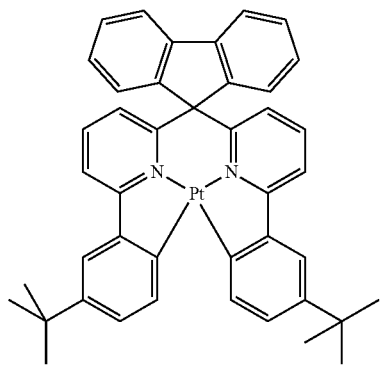
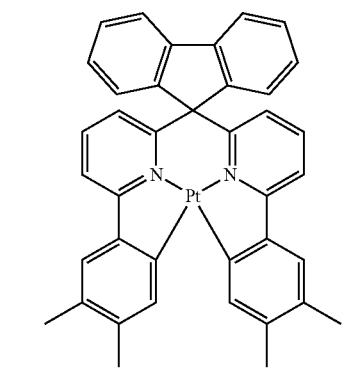
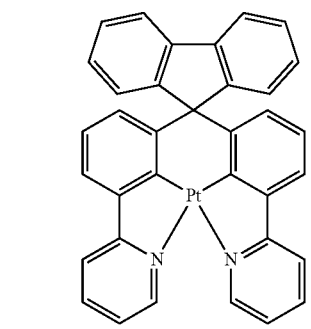
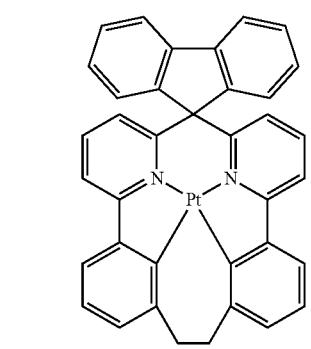
148
-continued
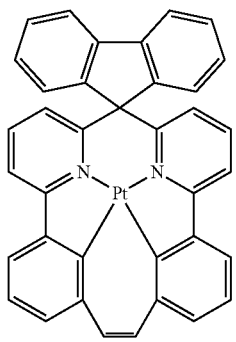
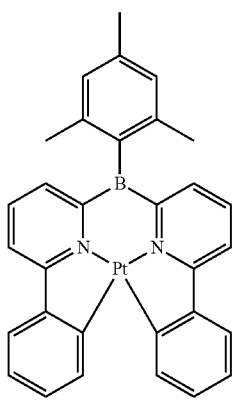
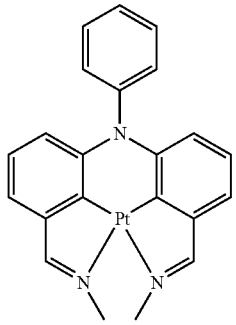
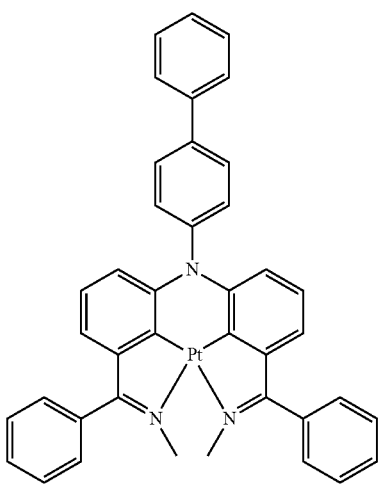

| 149 -continued | 150 -continued |
|---|---|
| 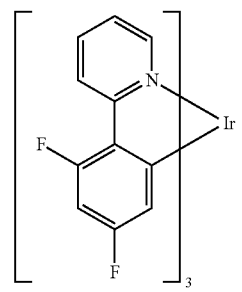 | 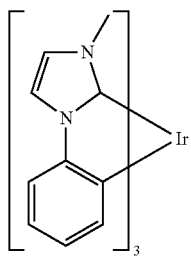 |
| 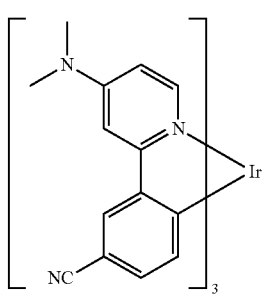 | 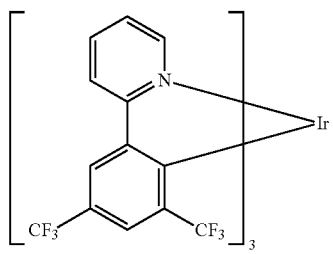 |
| 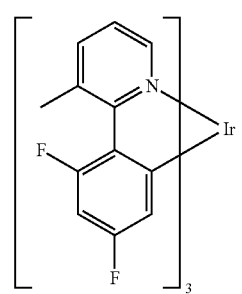 | 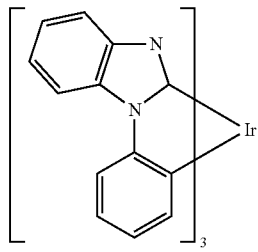 |
| 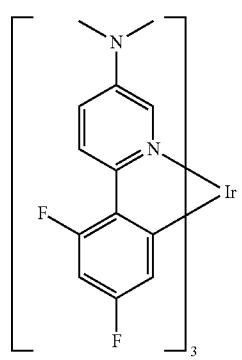 | 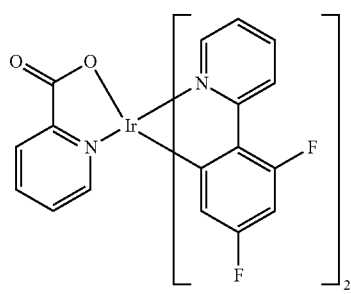 |
| 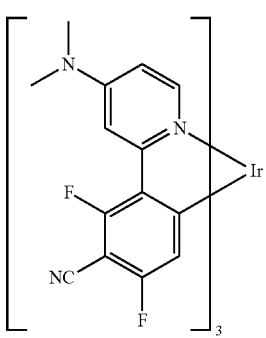 | 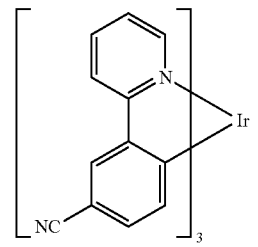 |
| | 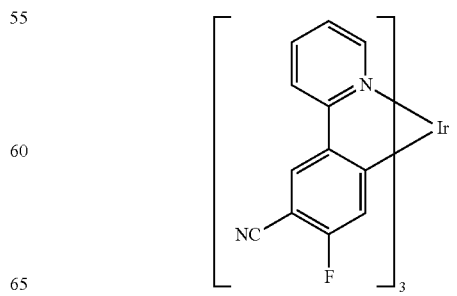 |

151
-continued
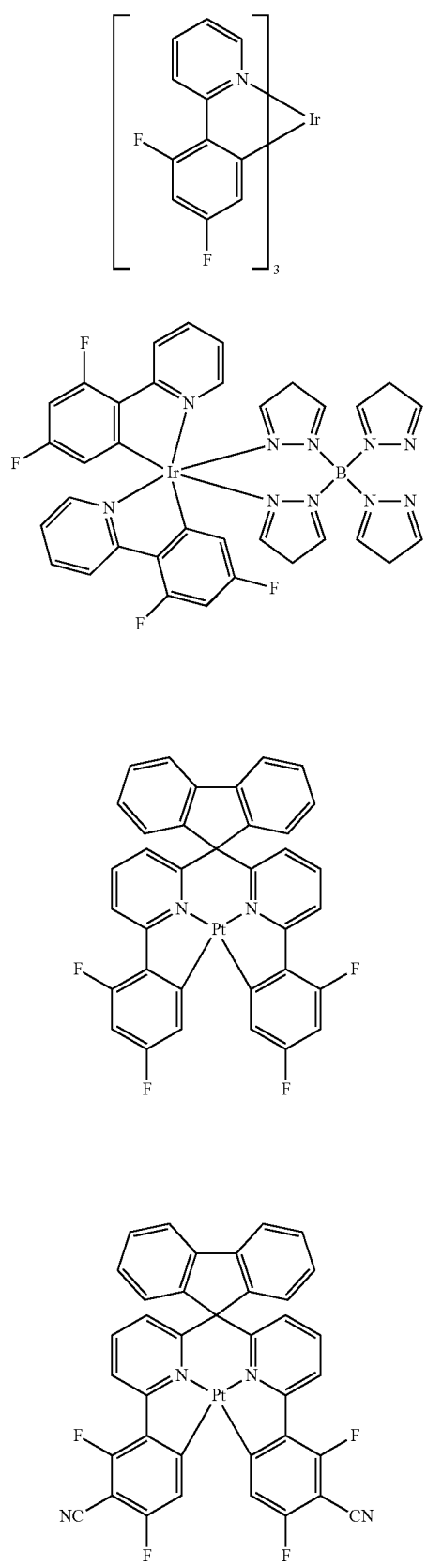
152
-continued
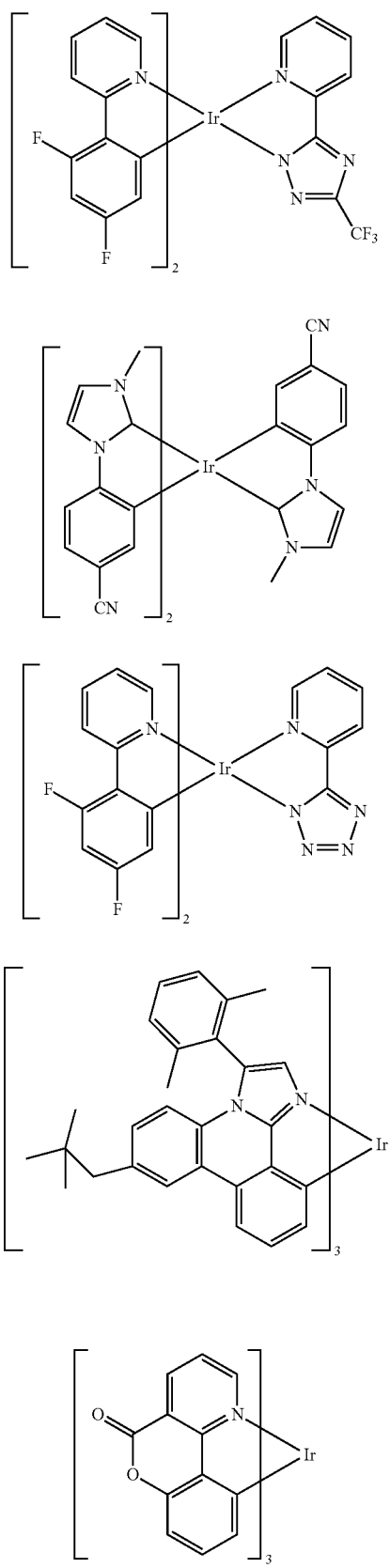

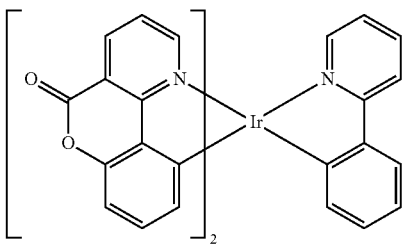
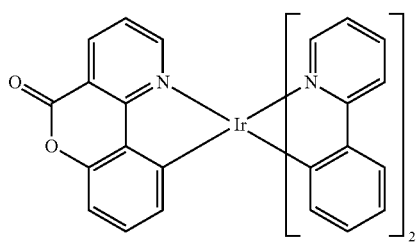
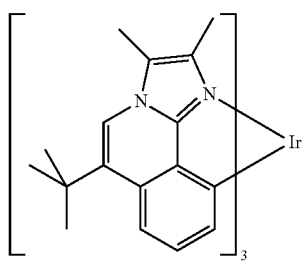
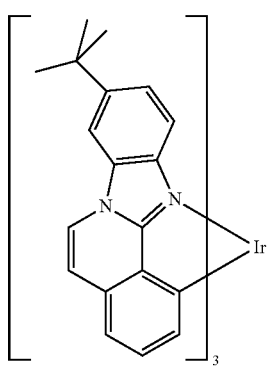
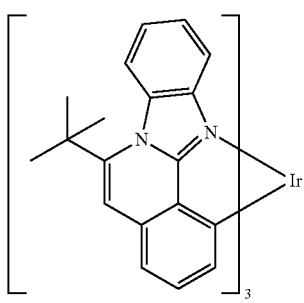
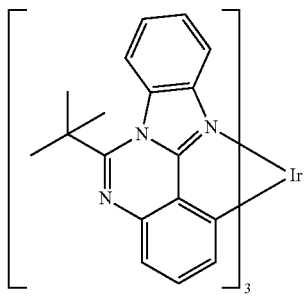
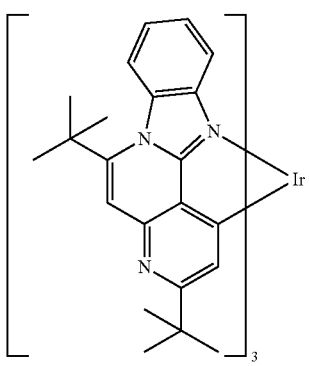
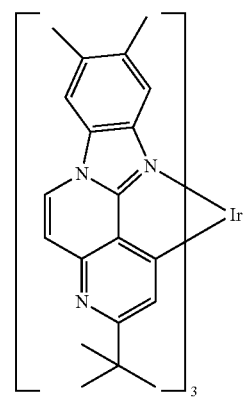

Preferred fluorescent emitters, besides the compounds of the formula (I), are selected from the class of the arylamines. An arylamine or aromatic amine in the sense of the present invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and in WO 2013/185871. Preference is likewise given to the benzoindenofluorenamines disclosed in WO 2014/037077 and the benzofluorenamines disclosed in EP 13000012.8.

Suitable matrix materials, preferably for fluorescent emitters, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154 and the pyrene compounds disclosed in EP 1749809, EP 1905754 and US 2012/0187826.

Preferred matrix materials for phosphorescent emitters are, besides the compounds of the formula (I), aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Suitable charge-transport materials, as can be used in the hole-injection or hole-transport layer or electron-blocking layer or in the electron-transport layer of the electronic device according to the invention, besides the compounds of the formula (I), are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Apart from the compounds of the formula (I), preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with WO 2014/015937, WO 2014/015938 and WO 2014/015935), spirodibenzopyranamines (for example in accordance with WO 2013/083216) and dihydroacridine derivatives (for example in accordance with WO 2012/150001).

The cathode of the electronic device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, provided with contacts and finally sealed in order to exclude harmful effects of water and air.

In a preferred embodiment, the electronic device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an electronic device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an electronic device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an electronic device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

A-1) Example 1

Synthesis of Compounds (1-1) to (1-13)

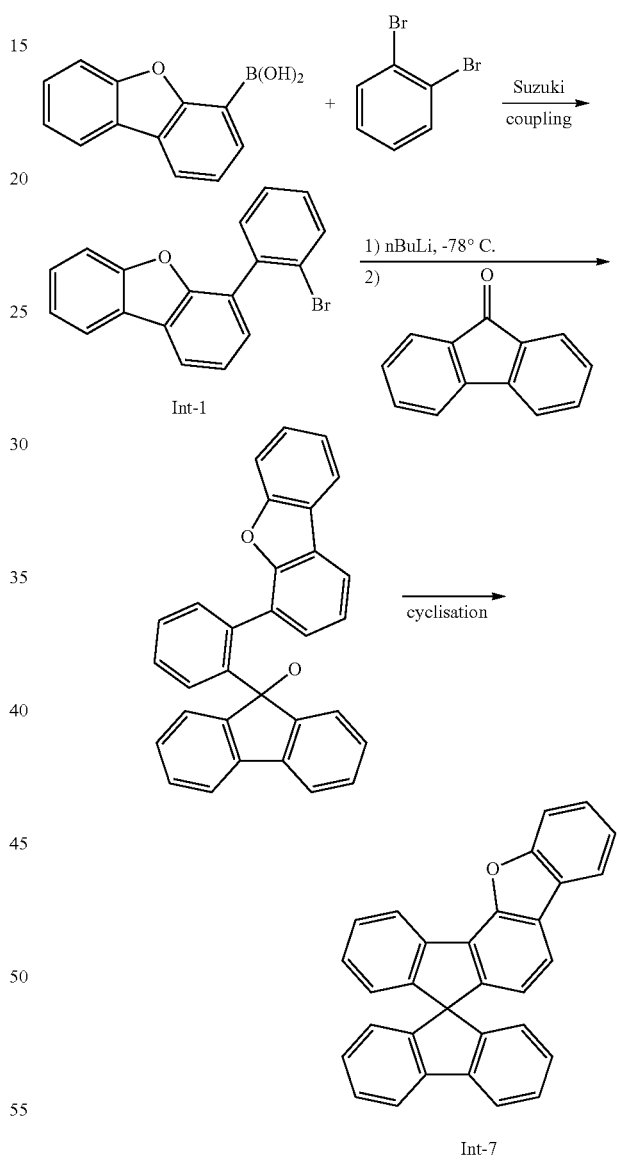

Synthesis of 4-(2-bromophenyl)dibenzofuran Int-1

100 g (462 mmol) of dibenzofuran-4-boronic acid, 106 g (439 mmol) of 1,2-dibromobenzene and 10.7 g (9.2 mmol) of Pd($Ph_3P$)$_4$ are suspended in 980 ml of dioxane. 979 ml of 2 M potassium carbonate solution are slowly added to this suspension, and the reaction mixture is heated under reflux for 16 h. After cooling, the organic phase is separated off, filtered through silica gel, washed three times with 200 ml of water and subsequently evaporated to dryness. The residue is purified by chromatography on silica gel. Yield: 87 g (270 mmol), 58% of theory, purity according to HPLC>98%.

Synthesis of Intermediate Int-7

31 g (90 mmol) of 4-(2-bromophenyl)dibenzofuran are initially introduced in 300 ml of THF at −78° C. 40 ml of BuLi (2 M in hexane) are added dropwise at this temperature. After 1 hour, 16.9 g (94 mmol) of fluoren-9-one in 200 ml of THF are added dropwise. The batch is left to stir overnight at room temperature, added to ice-water and extracted with dichloromethane. The combined organic phases are washed with water and dried over sodium sulfate. The solvent is removed in vacuo, and the residue is, without further purification, heated under reflux at 100° C. overnight with 94 ml of HCl and 1074 ml of AcOH. After cooling, the precipitated solid is filtered off with suction, washed once with 100 ml of water, three times with 100 ml of ethanol each time and subsequently recrystallised from heptane. Yield: 23.1 g (57 mmol), 58%; purity approx. 98% according to $^1$H-NMR.

The following compounds are prepared analogously to the synthesis of compound Int-1 described:

| | Starting material 1 | Starting material 2 | Product | Yield |
|---|---|---|---|---|
| Int-2 | 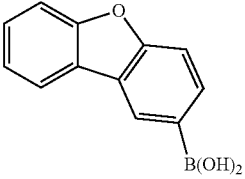 [SMILES: OB(O)c1ccc2oc3ccccc3c2c1] | 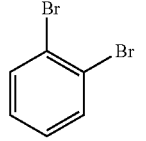 | 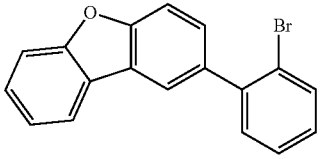 [SMILES: Brc1ccccc1-c1ccc2oc3ccccc3c2c1] | 62% |
| Int-3 | 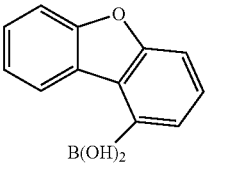 | 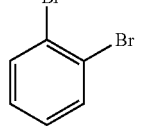 | 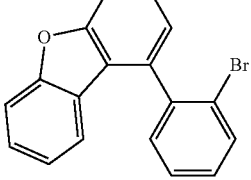 | 52% |
| Int-4 | 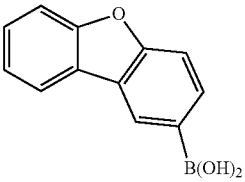 | 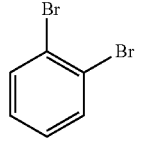 | 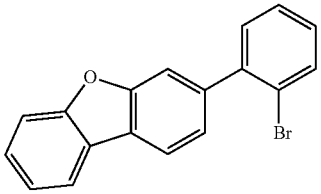 [SMILES: Brc1ccccc1-c1ccc2c(c1)oc1ccccc12] | 55% |
| Int-5 | 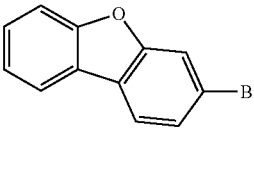 | 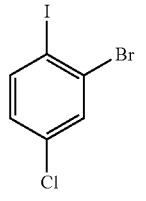 | 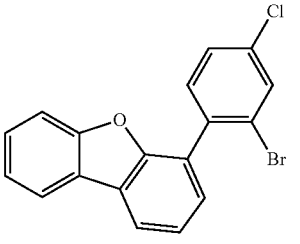 [SMILES: Clc1ccc(-c2cccc3c2oc2ccccc23)c(Br)c1] | 35% |
| Int-6 | 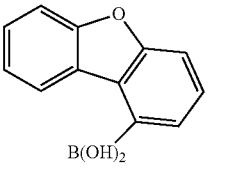 [SMILES: OB(O)c1cccc2oc3ccccc3c12] | 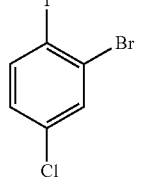 | 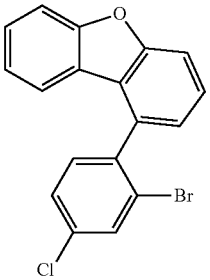 [SMILES: Clc1ccc(-c2cccc3oc4ccccc4c23)c(Br)c1] | 40% |

-continued

| | Starting material 1 | Starting material 2 | Product | Yield |
|---|---|---|---|---|
| Int-6a | | | | 60% |
| Int-6b | | | | 65% |
| Int-6c | | | | 55% |
| Int-6d | | | | 68% |
| Int-6e | | | | 60% |

-continued
| | Starting material 1 | Starting material 2 | Product | Yield |
|---|---|---|---|---|
| Int-6f | 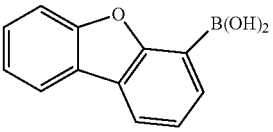 [SMILES: OB(O)c1cccc2c1oc1ccccc12] | 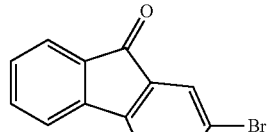 | 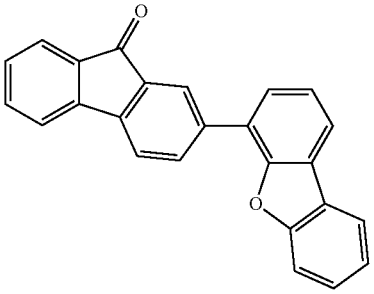 [SMILES: O=C1c2ccccc2-c2ccc(-c3cccc4c3oc3ccccc34)cc21] | 57% |
| Int-6g | 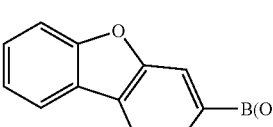 | 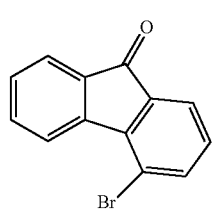 [SMILES: O=C1c2ccccc2-c2c(Br)cccc21] | 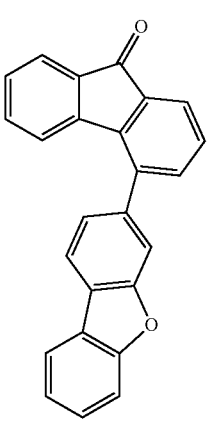 [SMILES: O=C1c2ccccc2-c2c1cccc2-c1ccc2c(c1)oc1ccccc12] | 60% |
| Int-6h | 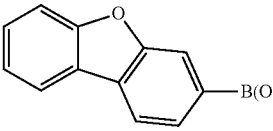 | 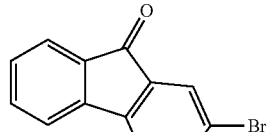 | 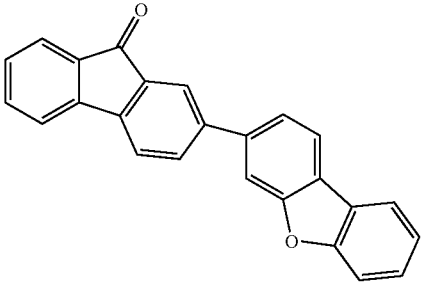 [SMILES: O=C1c2ccccc2-c2ccc(-c3ccc4c(c3)oc3ccccc34)cc21] | 65% |
The following compounds are prepared analogously to the synthesis of compound Int-7 described:
| | Starting material 1 | Starting material 2 | Product | Yield |
|---|---|---|---|---|
| Int-8 | 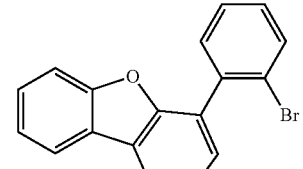 | 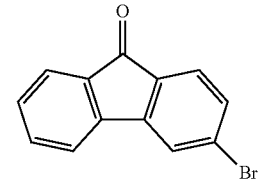[2041-19-2] | 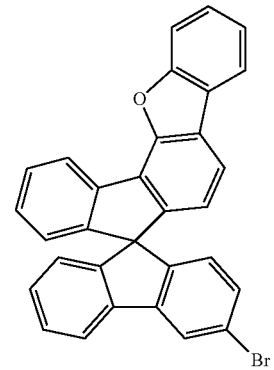 [SMILES: Brc1ccc2c(c1)-c1ccccc1C21c2ccccc2-c2c1ccc1c2oc2ccccc21] | 80% |

-continued
| Starting material 1 | Starting material 2 | Product | Yield |
|---|---|---|---|
| Int-9 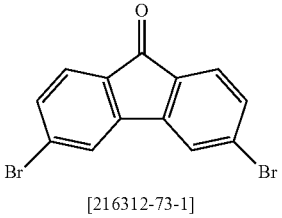 [SMILES: O=C1c2ccc(Br)cc2-c2cc(Br)ccc21] | 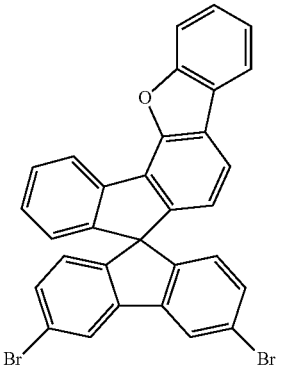 [SMILES: Brc1ccc2c(c1)-c1cc(Br)ccc1C21c2ccccc2-c2c1ccc1c2oc2ccccc21] [216312-73-1] | 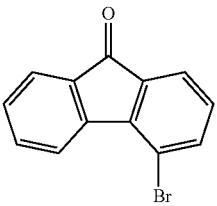 | 70% |
| Int-10 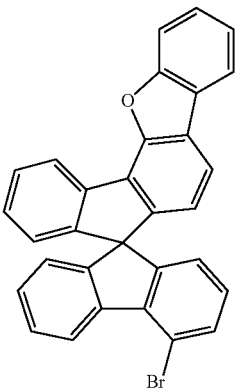 [SMILES: Brc1cccc2c1-c1ccccc1C21c2ccccc2-c2c1ccc1c2oc2ccccc21] | 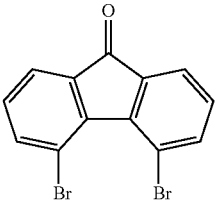 [4269-17-4] | 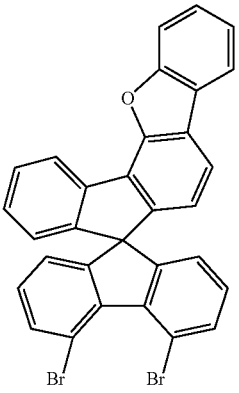 [SMILES: Brc1cccc2c1-c1c(Br)cccc1C21c2ccccc2-c2c1ccc1c2oc2ccccc21] | 70% |
| Int-11 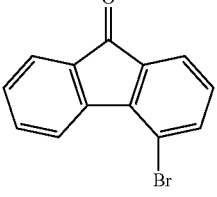 | [69414-97-7] | | 79% |
| Int-12 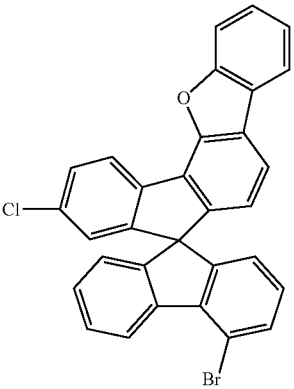 [SMILES: Clc1ccc2c(c1)C1(c3ccccc3-c3c(Br)cccc31)c1ccc3c(oc4ccccc43)c1-2] | [4269-17-4] | | 72% |

-continued

| Starting material 1 | Starting material 2 | Product | Yield |
|---|---|---|---|
| Int-13 | [486-25-9] | | 75% |
| Int-14 | [4269-17-4] | | 80% |
| Int-15 | [3096-49-9] | | 75% |
| Int-16 | [115033-91-5] | | 73% |

-continued
| Starting material 1 | Starting material 2 | Product | Yield |
|---|---|---|---|
| Int-17 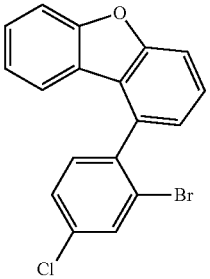 [SMILES: Clc1ccc(-c2cccc3oc4ccccc4c23)c(Br)c1] | 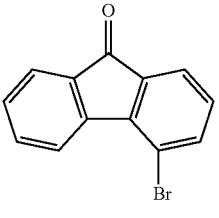 [4269-17-4] | 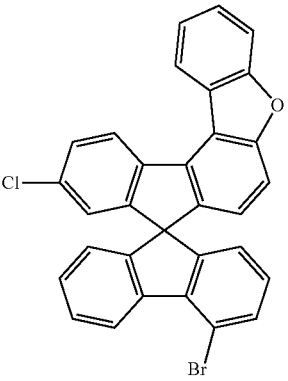 [SMILES: Clc1ccc2c(c1)C1(c3ccccc3-c3c(Br)cccc31)c1ccc3oc4ccccc4c3c1-2] | 70% |
| Int-18 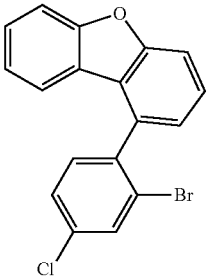 [SMILES: Clc1ccc(-c2cccc3oc4ccccc4c23)c(Br)c1] | 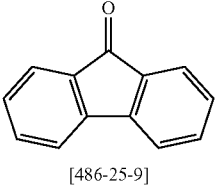 [SMILES: O=C1c2ccccc2-c2ccccc21] [486-25-9] | 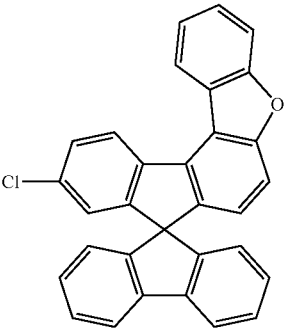 [SMILES: Clc1ccc2c(c1)C1(c3ccccc3-c3ccccc31)c1ccc3oc4ccccc4c3c1-2] | 75% |
| Int-19 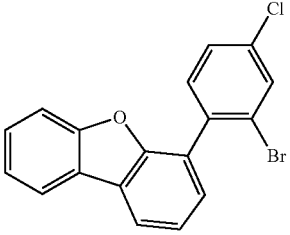 [SMILES: Clc1ccc(-c2cccc3c2oc2ccccc23)c(Br)c1] | 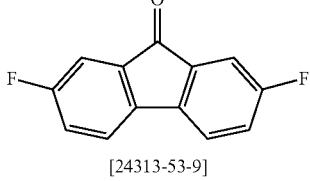 [24313-53-9] | 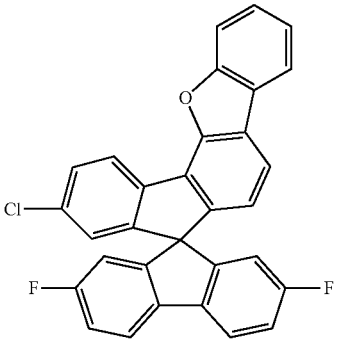 [SMILES: Fc1ccc2c(c1)C1(c3cc(F)ccc3-2)c2cc(Cl)ccc2-c2c1ccc1c2oc2ccccc21] | 65% |
| Int-20 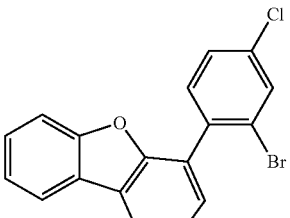 | 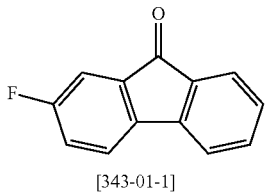 [SMILES: O=C1c2ccccc2-c2ccc(F)cc21] [343-01-1] | 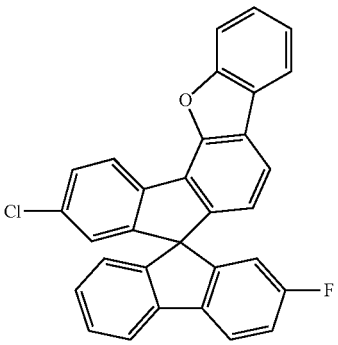 [SMILES: Fc1ccc2c(c1)C1(c3ccccc3-2)c2cc(Cl)ccc2-c2c1ccc1c2oc2ccccc21] | 58% |

-continued
| Starting material 1 | Starting material 2 | Product | Yield |
|---|---|---|---|
| Int-21 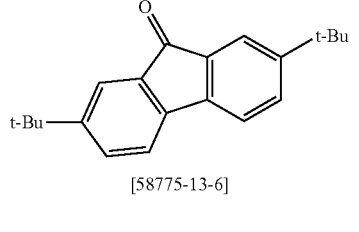 [SMILES: CC(C)(C)c1ccc2c(c1)C(=O)c1cc(C(C)(C)C)ccc1-2] | [58775-13-6] | 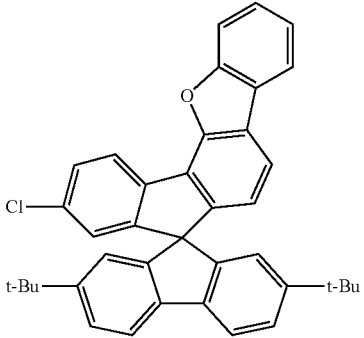 [SMILES: CC(C)(C)c1ccc2c(c1)C1(c3cc(C(C)(C)C)ccc3-2)c2cc(Cl)ccc2-c2c1ccc1c2oc2ccccc21] | 80% |
| Int-22 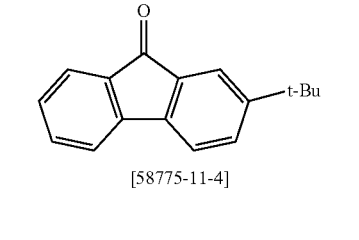 [SMILES: CC(C)(C)c1ccc2c(c1)C(=O)c1ccccc1-2] | [58775-11-4] | 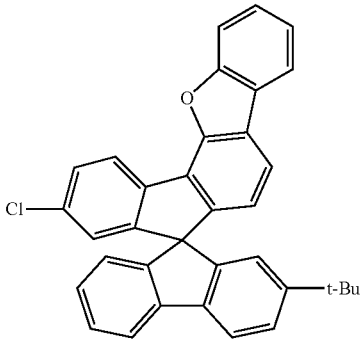 [SMILES: CC(C)(C)c1ccc2c(c1)C1(c3ccccc3-2)c2cc(Cl)ccc2-c2c1ccc1c2oc2ccccc21] | 72% |
| Int-23 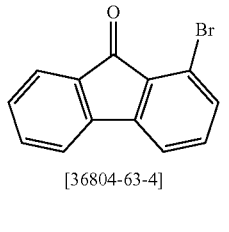 [SMILES: O=C1c2ccccc2-c2cccc(Br)c21] | [36804-63-4] | 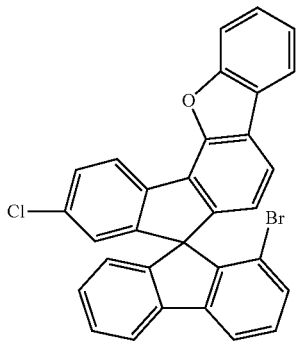 [SMILES: Clc1ccc2c(c1)C1(c3ccccc3-c3cccc(Br)c31)c1ccc3c(oc4ccccc43)c1-2] | 75% |
| Int-24 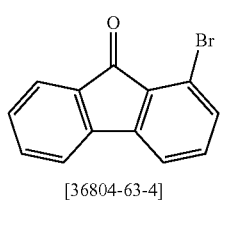 [SMILES: O=C1c2ccccc2-c2cccc(Br)c21] | [36804-63-4] | 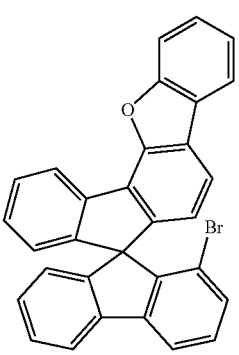 [SMILES: Brc1cccc2c1C1(c3ccccc3-2)c2ccccc2-c2c1ccc1c2oc2ccccc21] | 67% |

-continued
| Starting material 1 | Starting material 2 | Product | Yield |
|---|---|---|---|
| Int-24a 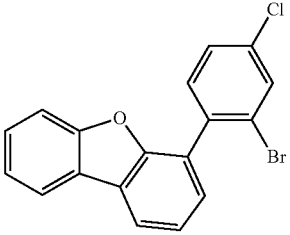 [SMILES: Clc1ccc(-c2cccc3c2oc2ccccc23)c(Br)c1] | 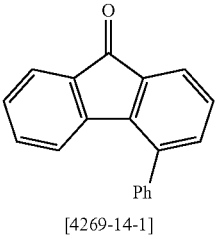 [SMILES: O=C1c2ccccc2-c2c1cccc2-c1ccccc1] [4269-14-1] | 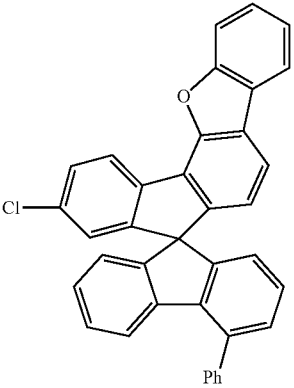 [SMILES: Clc1ccc2c(c1)C1(c3ccccc3-c3c(-c4ccccc4)cccc31)c1ccc3c(oc4ccccc43)c1-2] | 75% |
| Int-24b 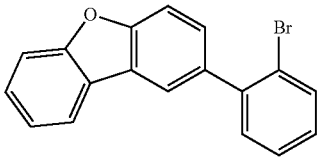 [SMILES: Brc1ccccc1-c1ccc2oc3ccccc3c2c1] | 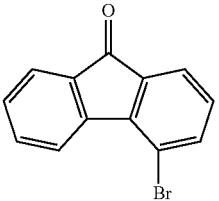 [SMILES: O=C1c2ccccc2-c2c(Br)cccc21] | 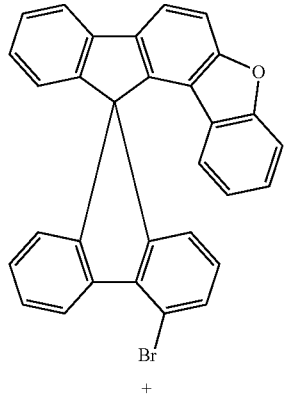 + | 70% |
| Int-24c 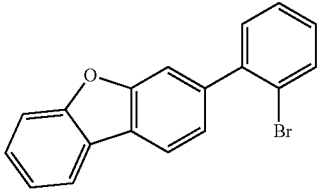 [SMILES: Brc1ccccc1-c1ccc2c(c1)oc1ccccc12] | 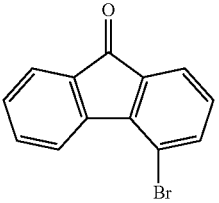 [SMILES: O=C1c2ccccc2-c2c(Br)cccc21] | 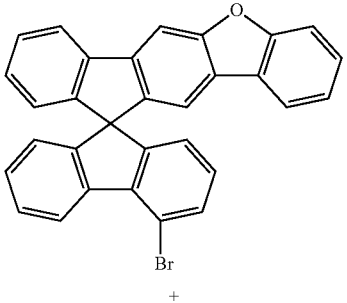 + | 65% |

-continued
| Starting material 1 | Starting material 2 | Product | Yield |
|---|---|---|---|
| | | 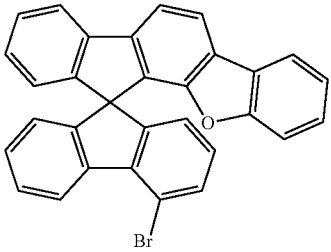 [SMILES: Brc1cccc2c1-c1ccccc1C21c2ccccc2-c2ccc3c(oc4ccccc43)c21] | |
| Int-24d 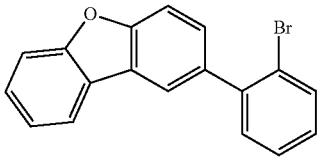 [SMILES: Brc1ccccc1-c1ccc2oc3ccccc3c2c1] | 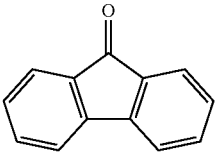 [SMILES: O=C1c2ccccc2-c2ccccc21] | 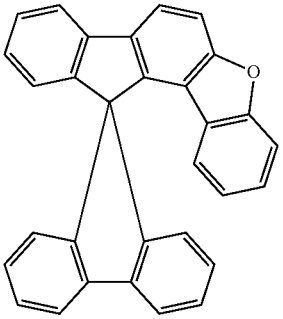 + 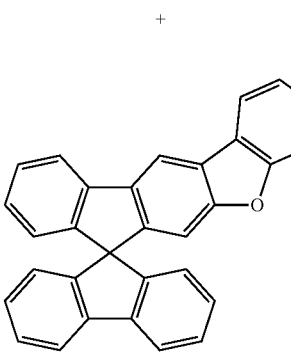 | 75% |
| Int-24e 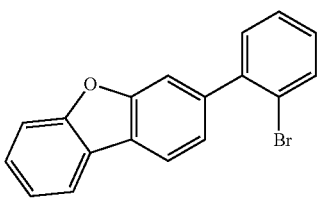 [SMILES: Brc1ccccc1-c1ccc2c(c1)oc1ccccc12] | 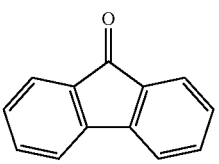 [SMILES: O=C1c2ccccc2-c2ccccc21] | 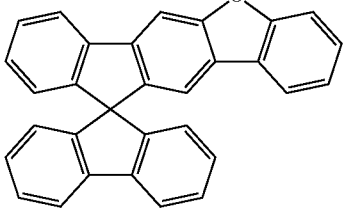 + 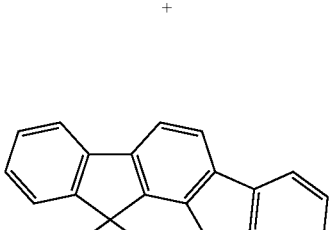 | 80% |

-continued
| Starting material 1 | Starting material 2 | Product | Yield |
|---|---|---|---|
| Int-24f 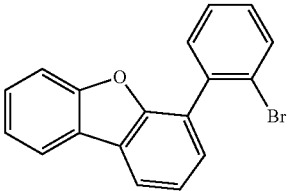 [SMILES: Brc1ccccc1-c1cccc2c1oc1ccccc12] | 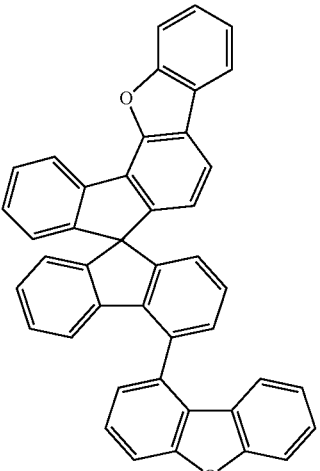 | 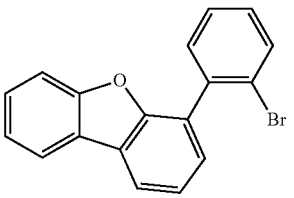 [SMILES: Brc1ccccc1-c1cccc2c1oc1ccccc12] | 70% |
| Int-24g 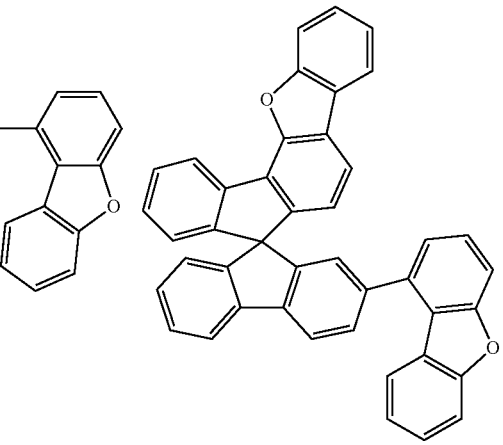 | 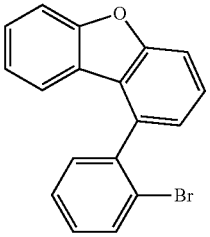 [SMILES: Brc1ccccc1-c1cccc2oc3ccccc3c12] | 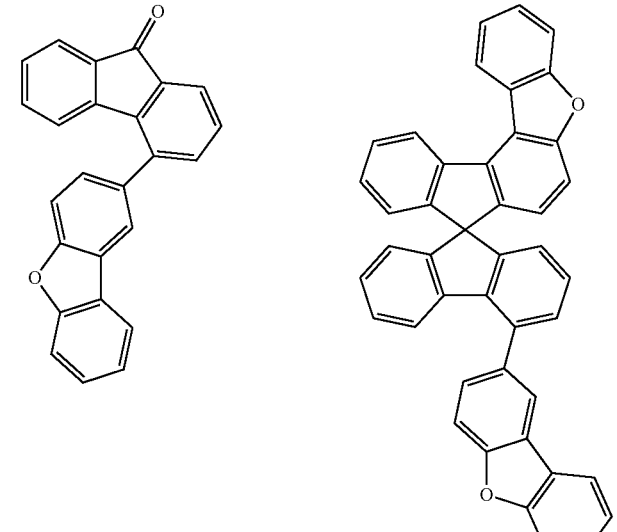 | 65% |
| Int-24h | | | 78% |

-continued
| Starting material 1 | Starting material 2 | Product | Yield |
|---|---|---|---|
| Int-24i 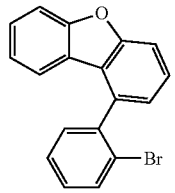 [SMILES: Brc1ccccc1-c1cccc2oc3ccccc3c12] | 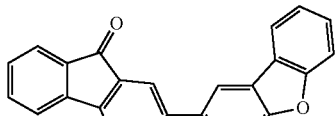 | 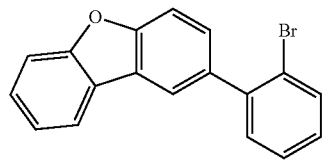 [SMILES: Brc1ccccc1-c1ccc2oc3ccccc3c2c1] | 62% |
| Int-24j 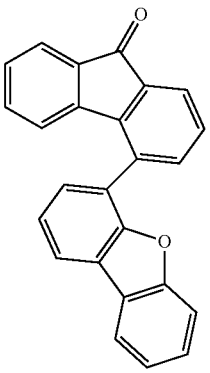 [SMILES: O=C1c2ccccc2-c2c1cccc2-c1cccc2c1oc1ccccc12] | 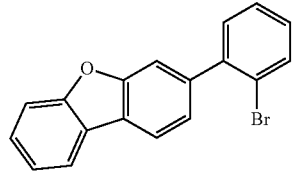 [SMILES: Brc1ccccc1-c1ccc2c(c1)oc1ccccc12] | 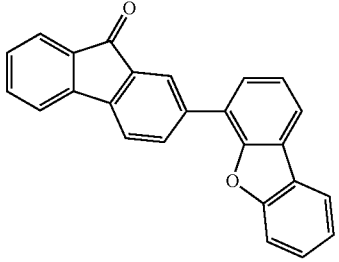 [SMILES: O=C1c2ccccc2-c2ccc(-c3cccc4c3oc3ccccc34)cc21] | 65% |
| Int-24k | | | 70% |

-continued
| Starting material 1 | Starting material 2 | Product | Yield |
|---|---|---|---|
| Int-24l | | | 81% |
| Int-24m | | | 75% |
Synthesis of Compound (1-1)
-continued
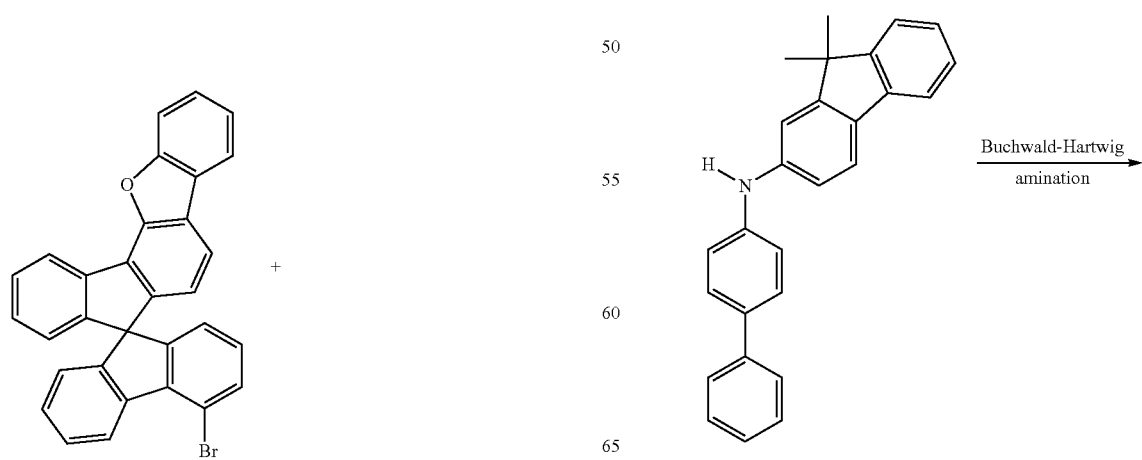

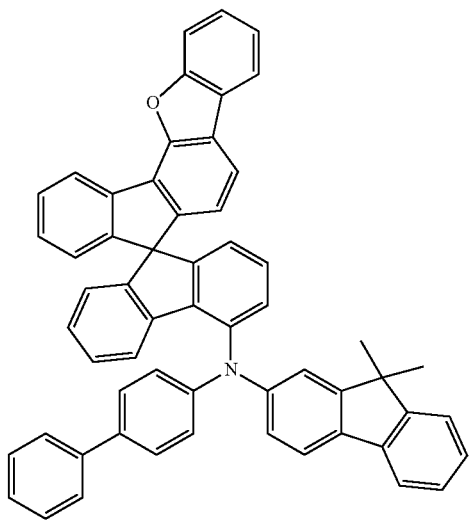

(1-1)

11.5 g (31.5 mmol) of biphenyl-4-yl-(9,9-dimethyl-9H-fluoren-2-yl)amine and 14.0 g (28.8 mol) of the bromospiro derivative are dissolved in 320 ml of toluene. The solution is degassed and saturated with $N_2$. 6.8 ml (2.88 mmol) of a 10% tri-tert-butylphosphine solution and 1.32 g (1.44 mmol) of $Pd_2(dba)_3$ are then added, and 9.5 g of sodium tert-butoxide (86.5 mmol) are subsequently added. The reaction mixture is heated at the boil under a protective atmosphere for 5 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9% (HPLC). The yield of compound (1-1) is 16.5 g (75% of theory).

Synthesis of Compounds (1-2) to (1-16)

The following compounds are also prepared analogously to the synthesis of compound (1-1) described in Example 1.

| | Starting material 1 | Starting material 2 | Product | Yield |
|---|---|---|---|---|
| 1-2 | (structure with Br) | [102113-98-4] (H-N diphenyl amine structure) | (product structure) | 78% |

| Starting material 1 | Starting material 2 | Product | Yield |
|---|---|---|---|
| 1-3 | | | 82% |
| 1-4 | [500717-23-7] | | 88% |

| Starting material 1 | Starting material 2 | Product | Yield |
|---|---|---|---|
| 1-5 | [102113-98-4] | | 67% |
| 1-6 | | | 76% |
| 1-7 | | | 80% |

-continued
| Starting material 1 | Starting material 2 | Product | Yield |
|---|---|---|---|
| 1-8 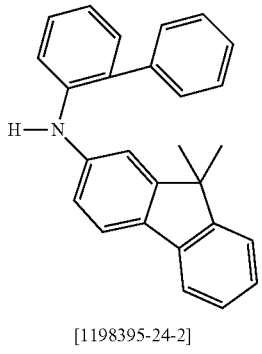 [SMILES: CC1(C)c2ccccc2-c2ccc(Nc3ccccc3-c3ccccc3)cc21] | 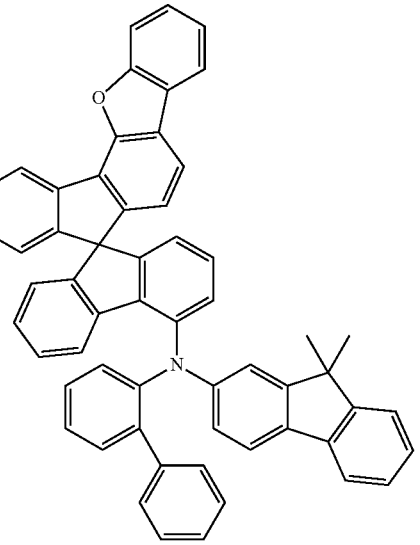 [1198395-24-2] | 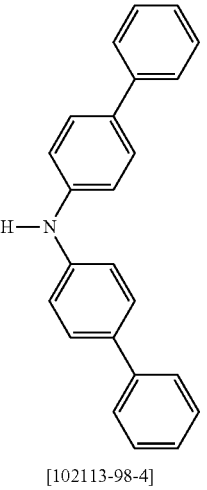 [SMILES: c1ccc(-c2ccc(Nc3ccc(-c4ccccc4)cc3)cc2)cc1] | 78% |
| 1-9 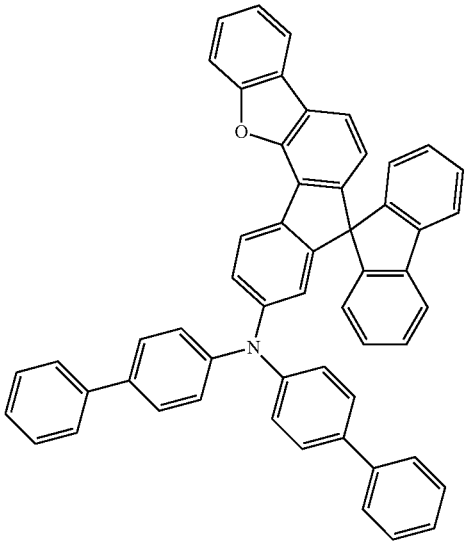 [SMILES: c1ccc(-c2ccc(N(c3ccc(-c4ccccc4)cc3)c3ccc4c(c3)C3(c5ccccc5-c5ccccc53)c3ccc5c(oc6ccccc65)c3-4)cc2)cc1] | [102113-98-4] | | 72% |

|Starting material 1|Starting material 2|Product|Yield|
|---|---|---|---|
|1-10|||83%|
|1-11||[102113-98-4] (2 eq.)|75%|
|1-12|||70%|

| Starting material 1 | Starting material 2 | Product | Yield |
|---|---|---|---|
| 1-13 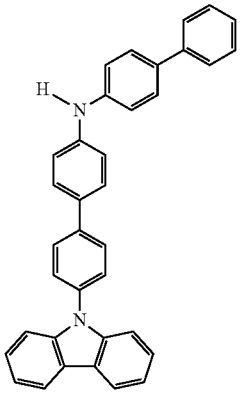 [SMILES: c1ccc(-c2ccc(Nc3ccc(-c4ccc(-n5c6ccccc6c6ccccc65)cc4)cc3)cc2)cc1] | 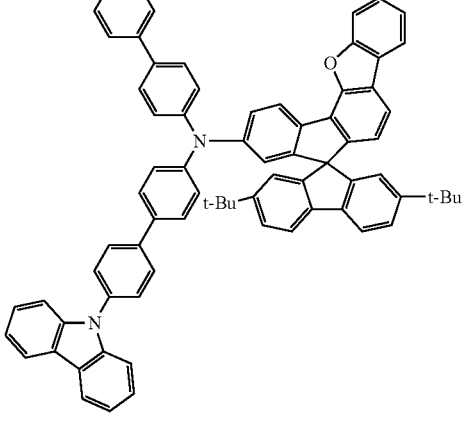 | 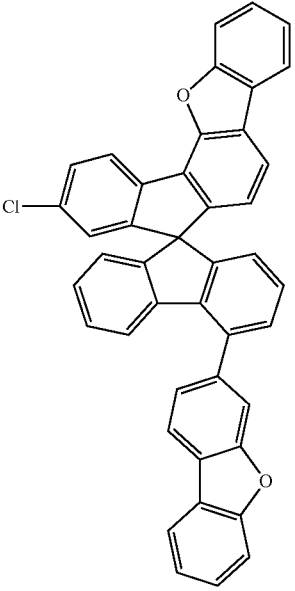 [SMILES: Clc1ccc2c(c1)C1(c3ccccc3-c3c(-c4ccc5c(c4)oc4ccccc45)cccc31)c1ccc3c(oc4ccccc43)c1-2] | 81% |
| 1-14 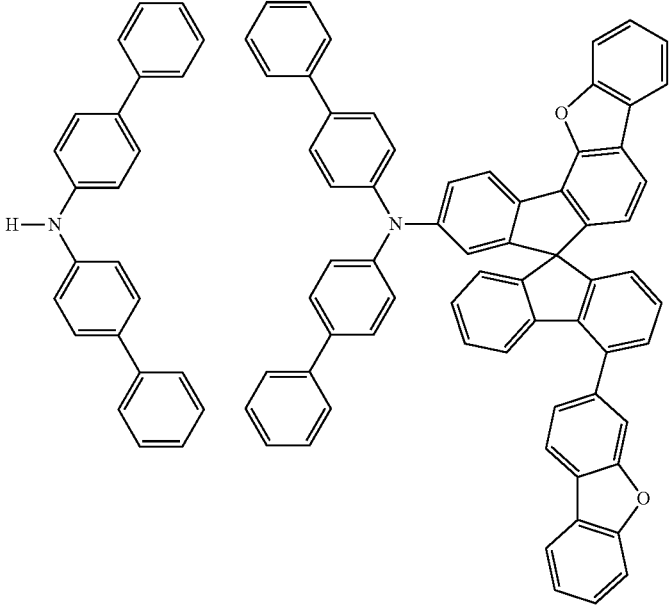 | 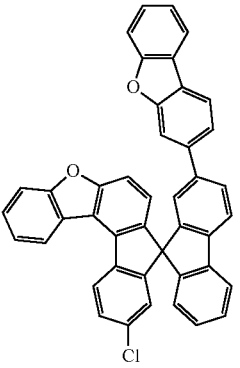 [SMILES: Clc1ccc2c(c1)C1(c3ccccc3-c3ccc(-c4ccc5c(c4)oc4ccccc45)cc31)c1ccc3oc4ccccc4c3c1-2] | 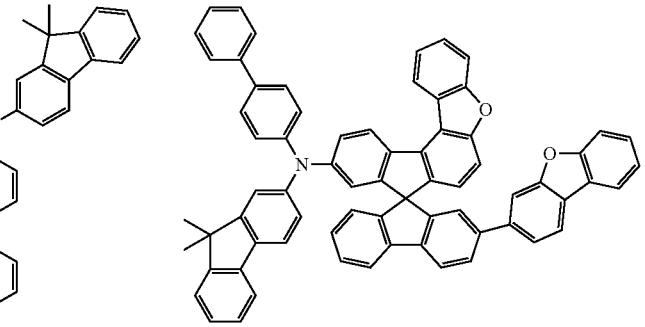 | 65% |
| 1-15 | | | 55% |

| Starting material 1 | Starting material 2 | Product | Yield |
|---|---|---|---|
| 1-16 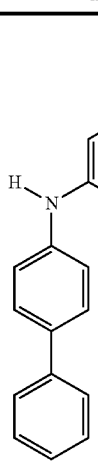 | 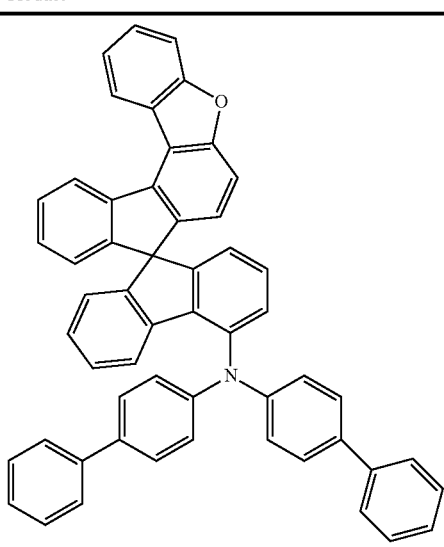 | 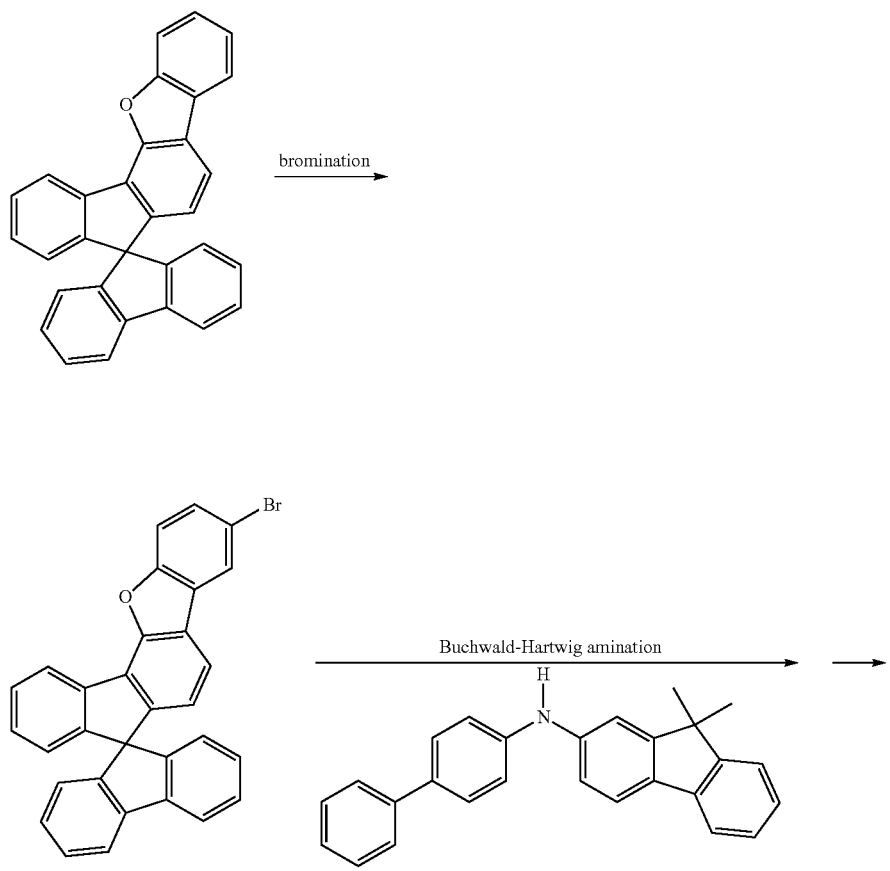 | 73% |
A-2) Example 2
Synthesis of Compounds (2-2) to (2-4)
bromination →
Buchwald-Hartwig amination →

-continued

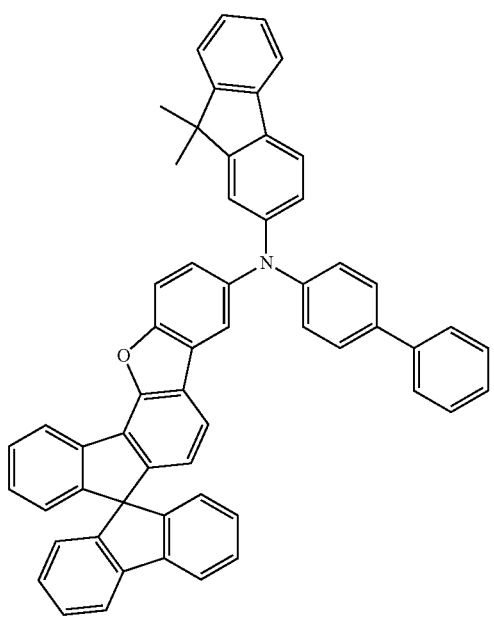

(2-1)

15.0 g (36.9 mmol) of the starting compound are dissolved in 150 ml of acetonitrile, and 5.2 g (29 mmol) of N-bromosuccinimide are added in portions at room temperature. When the reaction is complete, water and ethyl acetate are added, and the organic phase is separated off, dried and evaporated. The crude product is subsequently washed by stirring a number of times with hot MeOH/heptane (1:1). Yield: 14.3 g (80%) of the bromospiro derivative Int-25.

The following brominated compounds are prepared analogously:

| | Starting material 1 | Brominating reagent | Product | Yield |
|---|---|---|---|---|
| Int-26 | ![structure] | NBS | ![structure] | 78% |

-continued

| Starting material 1 | | Brominating reagent | Product | Yield |
|---|---|---|---|---|
| Int-27 | [structure] | 1) nBuLi, -78° C.<br>2) BrCH$_2$—CH$_2$Br | [structure with Br] | 65% |
| Int-27a | [structure] | 1) nBuLi, -78° C.<br>2) I$_2$ | [structure with I] | 75% |

Synthesis of Compounds (2-2) to (2-5)

The following compounds (2-2) to (2-5) are also prepared analogously to the synthesis of compound (1-1) described in Example 1.

| | Starting material 1 | Starting material 2 | Product | Yield |
|---|---|---|---|---|
| 2-2 | [structure with Br] | [structure] [102113-98-4] | [structure] | 82% |

-continued

| | Starting material 1 | Starting material 2 | Product | Yield |
|---|---|---|---|---|
| 2-3 | | | | 69% |
| 2-4 | | | | 88% |

| | Starting material 1 | Starting material 2 | Product | Yield |
|---|---|---|---|---|
| 2-5 | | | 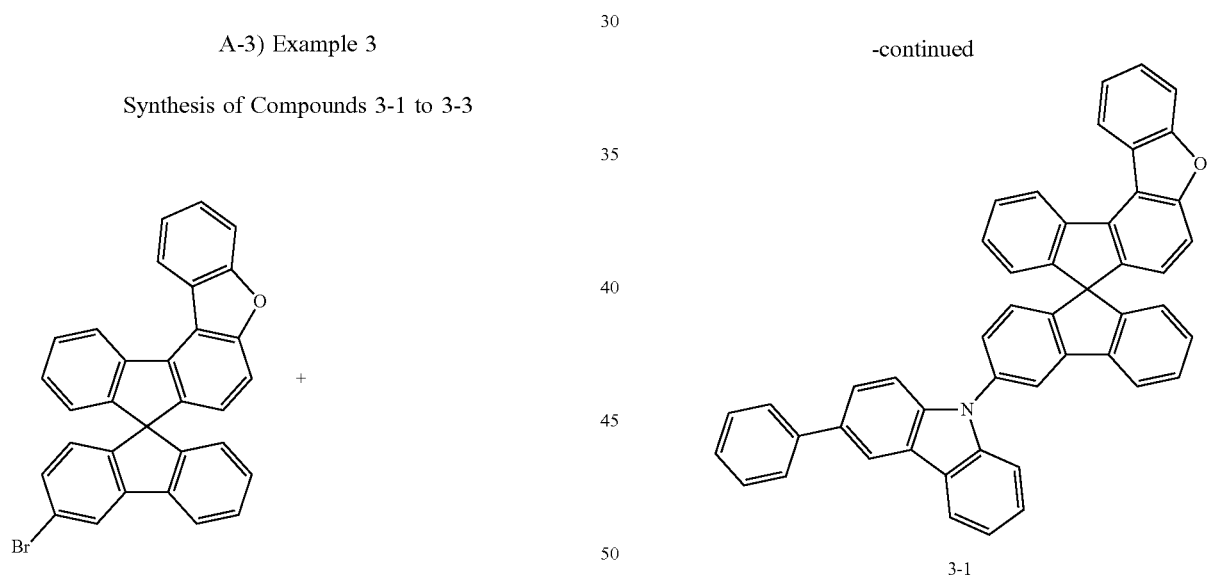 | 50% |

A-3) Example 3

Synthesis of Compounds 3-1 to 3-3

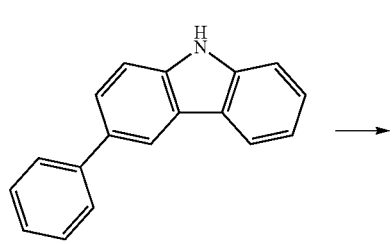

-continued 3-1

20.0 g (40.1 mmol) of bromine derivative, 9.7 g (40.1 mmol) of 3-phenyl-9H-carbazole and 24 g of $Rb_2CO_3$ are suspended in 250 ml of p-xylene. 0.95 g (4.2 mmol) of $Pd(OAc)_2$ and 12.6 ml of a 1 M tri-tert-butylphosphine solution are added to this suspension. The reaction mixture is heated under reflux for 36 h. After cooling, the organic phase is separated off, washed three times with 150 ml of water and subsequently evaporated to times from toluene and finally sublimed in a high vacuum, giving 15.9 g (24.1 mmol), corresponding to 60% of theory. The purity is 99.9%.

Synthesis of Compounds (3-2) to (3-4)

The following compounds (3-2) and (3-3) are also prepared analogously to the synthesis of compound (3-1) described in Example 1.

The following compounds are obtained analogously:

| | Starting material 1 | Starting material 2 | Product | Yield |
|---|---|---|---|---|
| 3-2 | | 1257220-47-5 | | 50% |
| 3-3 | | 1427738-11-1 | | 45% |

A-3a) Synthesis of Intermediates for Compounds Under A-4)

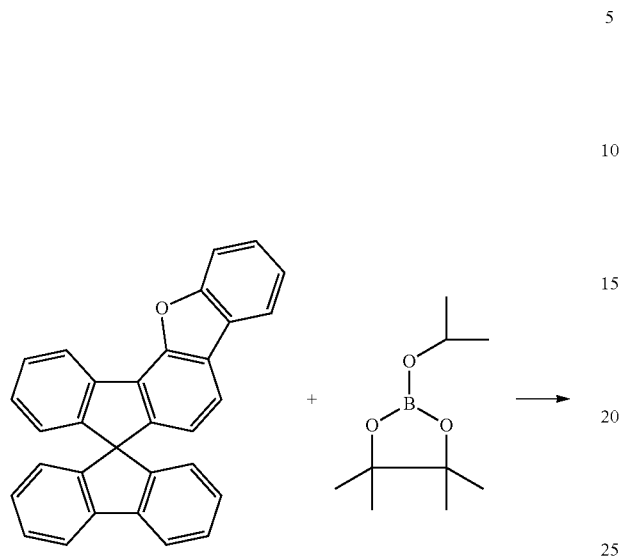 + 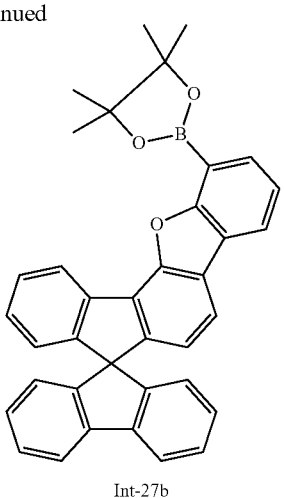

Int-27b 30 g (74 mmol) of dibenzospirofluorene are initially introduced in 400 ml of THF at −20° C. 49 ml of BuLi (2 M in hexane) are added dropwise at this temperature. After 4 hours, 33 ml (148 mmol) of isopropoxytetramethyldioxaborolane are added dropwise. The batch is left to stir overnight at room temperature. When the reaction is complete, water and ethyl acetate are added, and the organic phase is separated off, dried and evaporated. The residue is purified by chromatography on silica gel. Yield: 31 g (59 mmol), 80% of theory, purity according to HPLC>98%.

| | Starting material 1 | Borylating reagent | Product | Yield |
|---|---|---|---|---|
| Int-27c | | | | 85% |
| Int-27d | | | | 80% |

-continued

| Starting material 1 | Borylating reagent | Product | Yield |
|---|---|---|---|
| Int-27e | | | 75% |

A-4) Example 4

Synthesis of Compounds 4-1 to 4-13

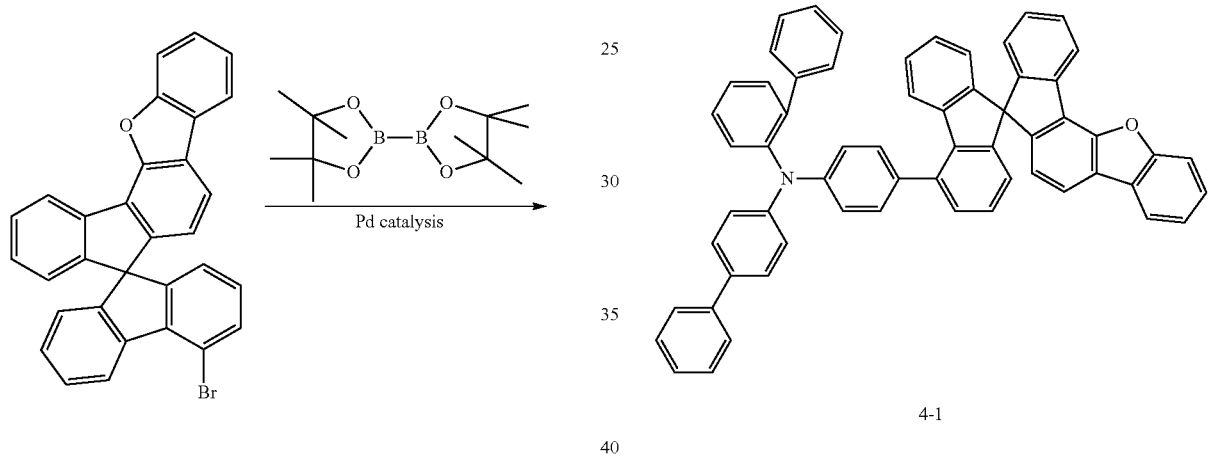

4-1

Spirofluoreneboronic Ester Derivative Int-28

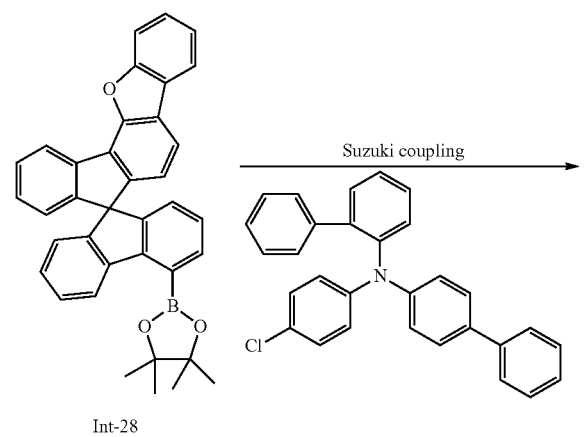

Int-28

50 g (103 mmol) of the bromospirofluorene derivative, 32 g (123 mmol) of bis(pinacolato)diborane and 30 g (309 mmol) of potassium acetate are suspended in 800 ml of dioxane. 2.5 g (3.09 mmol) of 1,1-bis(diphenylphosphino)ferrocenepalladium(II) dichloride complex with DCM are added to this suspension. The reaction mixture is heated under reflux for 16 h. After cooling, the organic phase is separated off, washed three times with 400 ml of water and subsequently evaporated to dryness. The residue is recrystallised from toluene (52 g, 95% yield).

The following compounds are prepared analogously:

| Starting material 1 | Product | Yield |
|---|---|---|
| Int-29 | | 90% |
| Int-30 | | 80% |
| Int-31 | | 88% |

| Starting material 1 | Product | Yield |
|---|---|---|
| Int-32 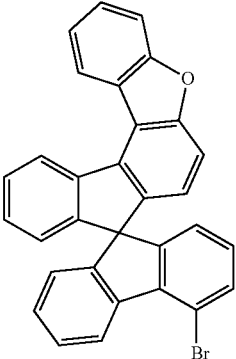 [SMILES: Brc1cccc2c1-c1ccccc1C21c2ccccc2-c2c1ccc1oc3ccccc3c21] | 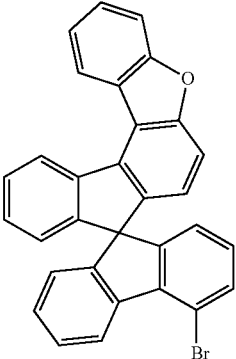 [SMILES: Brc1cccc2c1-c1ccccc1C21c2ccccc2-c2c1ccc1oc3ccccc3c21] | 88% |
| Int-33 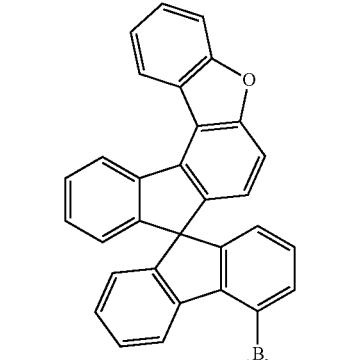 [SMILES: Brc1cccc2c1-c1ccccc1C21c2ccccc2-c2c1ccc1oc3ccccc3c21] | 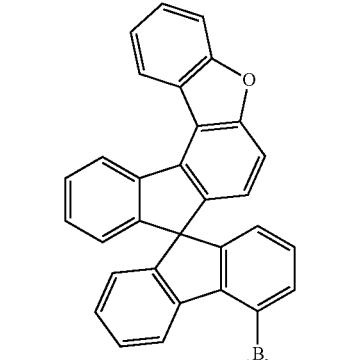 [SMILES: Brc1cccc2c1-c1ccccc1C21c2ccccc2-c2c1ccc1oc3ccccc3c21] | 91% |
| Int-34 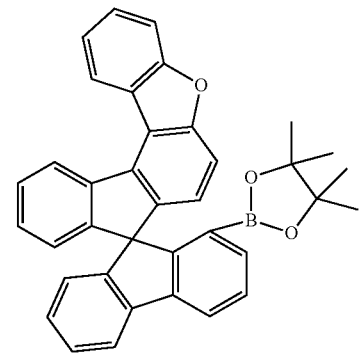 [SMILES: CC1(C)OB(c2cccc3c2C2(c4ccccc4-3)c3ccccc3-c3c2ccc2oc4ccccc4c32)OC1(C)C] | 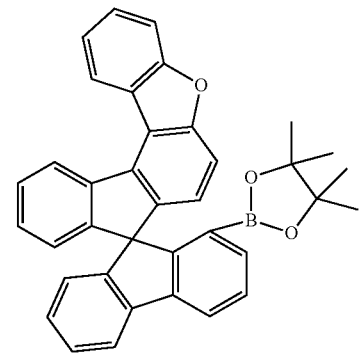 [SMILES: CC1(C)OB(c2cccc3c2C2(c4ccccc4-3)c3ccccc3-c3c2ccc2oc4ccccc4c32)OC1(C)C] | 85% |
| Int-34a 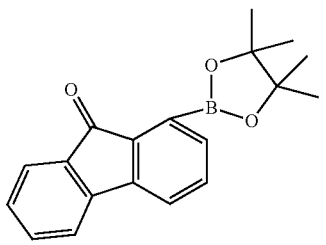 [SMILES: CC1(C)OB(c2cccc3c2C(=O)c2ccccc2-3)OC1(C)C] | 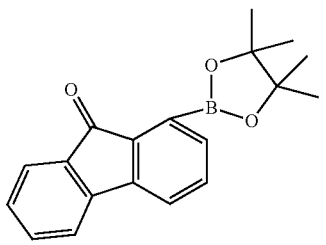 [SMILES: CC1(C)OB(c2cccc3c2C(=O)c2ccccc2-3)OC1(C)C] | 80% |

| Starting material 1 | Product | Yield |
|---|---|---|
| Int-34b  | | 85% |

Biphenyl-2-ylbiphenyl-4-yl-(4-chlorophenyl)amine
Int-35

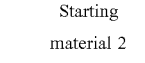

23.8 g of biphenyl-2-ylbiphenyl-4-ylamine (74 mmol) and 21.2 g of 4-chloroiodobenzene (89 mmol) are dissolved in 500 ml of toluene. The solution is degassed and saturated with $N_2$. 3 ml (3 mmol) of a 1 M tri-tert-butylphosphine solution and 0.33 g (1.48 mmol) of palladium(II) acetate are then added, and 10.7 g of sodium tert-butoxide (111 mmol) are subsequently added. The reaction mixture is heated at the boil under a protective atmosphere for 12 h. The mixture is subsequently partitioned between toluene and water, and the organic phase is washed three times with water and dried over $Na_2SO_4$ and evaporated in rotary evaporator. After filtration of the crude product through silica gel with toluene, the residue which remains is recrystallised from heptane/toluene. The yield is 29 g (90% of theory).

The following compounds are prepared analogously:

| | Starting material 1 | Starting material 2 | Product | Yield |
|---|---|---|---|---|
| Int-36 | 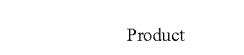 | | | 78% |

-continued

| | Starting material 1 | Starting material 2 | Product | Yield |
|---|---|---|---|---|
| Int-37 | | | | 80% |
| Int-38 | | | | 81% |
| Int-39 | | | | 92% |
| Int-40 | | | | 85% |

-continued

| | Starting material 1 | Starting material 2 | Product | Yield |
|---|---|---|---|---|
| Int-41 | [structure: H-N with 4-biphenyl and 4'-phenyl-biphenyl substituents] | [structure: 1-iodo-2-chlorobenzene] | [structure: N with 2-chlorophenyl, 4-biphenyl, and 4'-phenyl-biphenyl substituents] | 75% |

Synthesis of Compound (4-1)

24.6 g (46.3 mmol) of spirofluorene pinacoleboronic ester derivative and 20.0 g (46.3 mmol) of chlorine derivative are suspended in 300 ml of dioxane and 14.1 g of caesium fluoride (92.6 mmol). 4.1 g (5.56 mmol) of bis(tricyclohexylphosphine)palladium dichloride are added to this suspension, and the reaction mixture is heated under reflux for 24 h. After cooling, the organic phase is separated off, filtered through silica gel, washed three times with 100 ml of water and subsequently evaporated to dryness. After filtration of the crude product through silica gel with toluene, the residue which remains is recrystallised from heptane/toluene and finally sublimed in a high vacuum. The purity is 99.9%. The yield is 29.7 g (80% of theory).

Synthesis of Compounds (4-2) to (4-11) and
Int-41a to Int-41c

The following compounds are also prepared analogously to the synthesis of compound (4-1) described in Example 1.

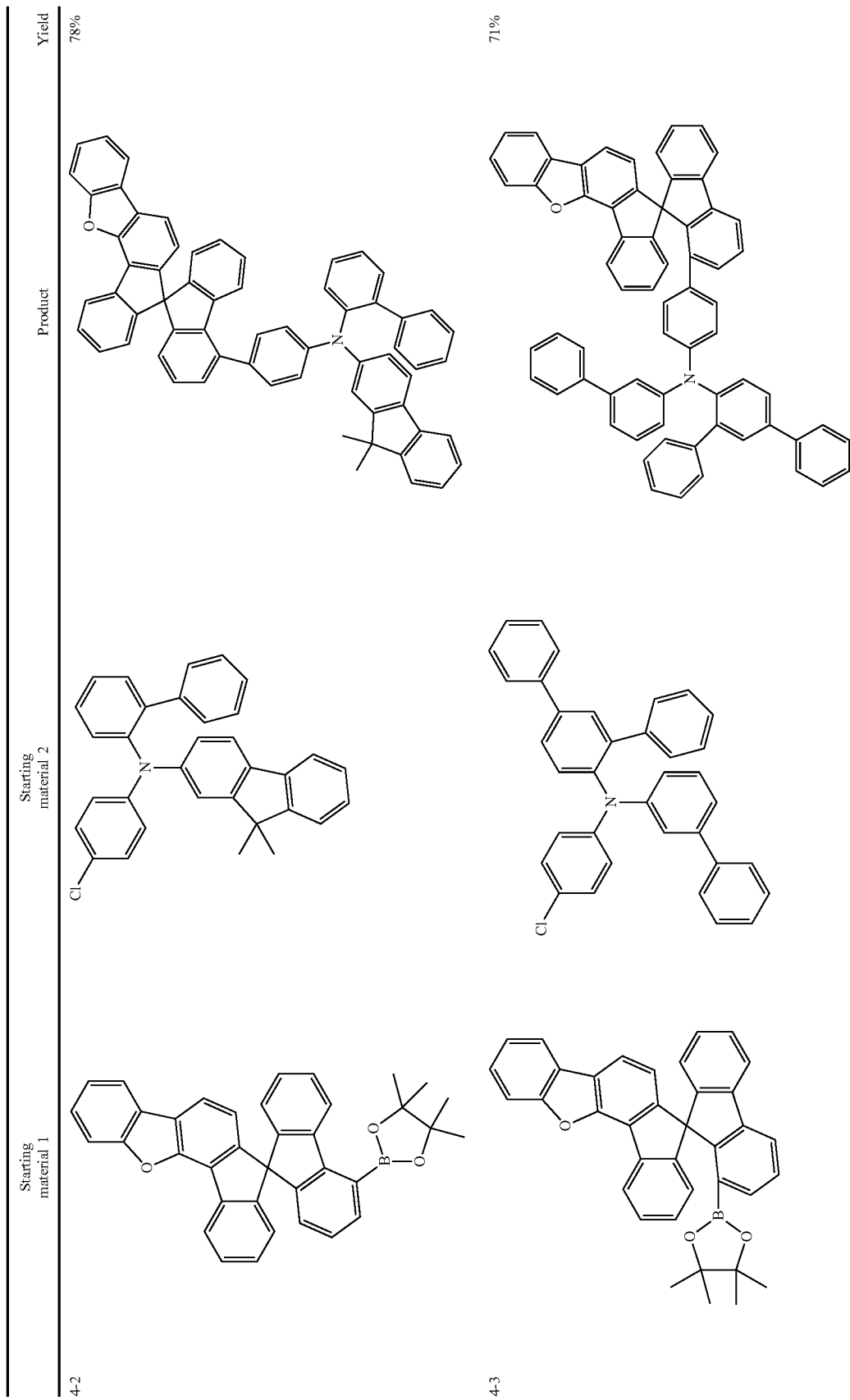

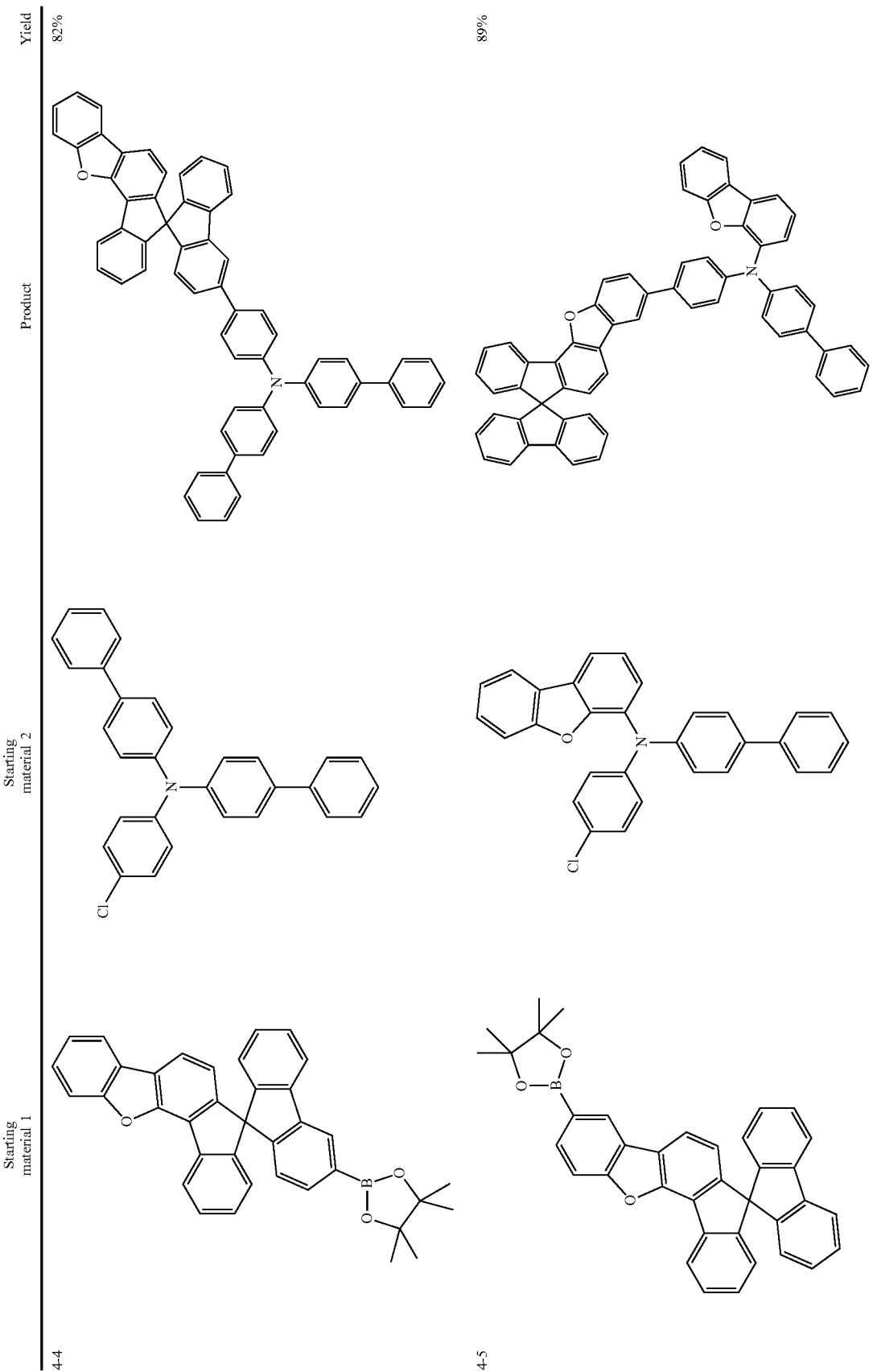

-continued

| | Starting material 1 | Starting material 2 | Product | Yield |
|---|---|---|---|---|
| 4-6 | | | | 69% |
| 4-7 | | | | 55% |

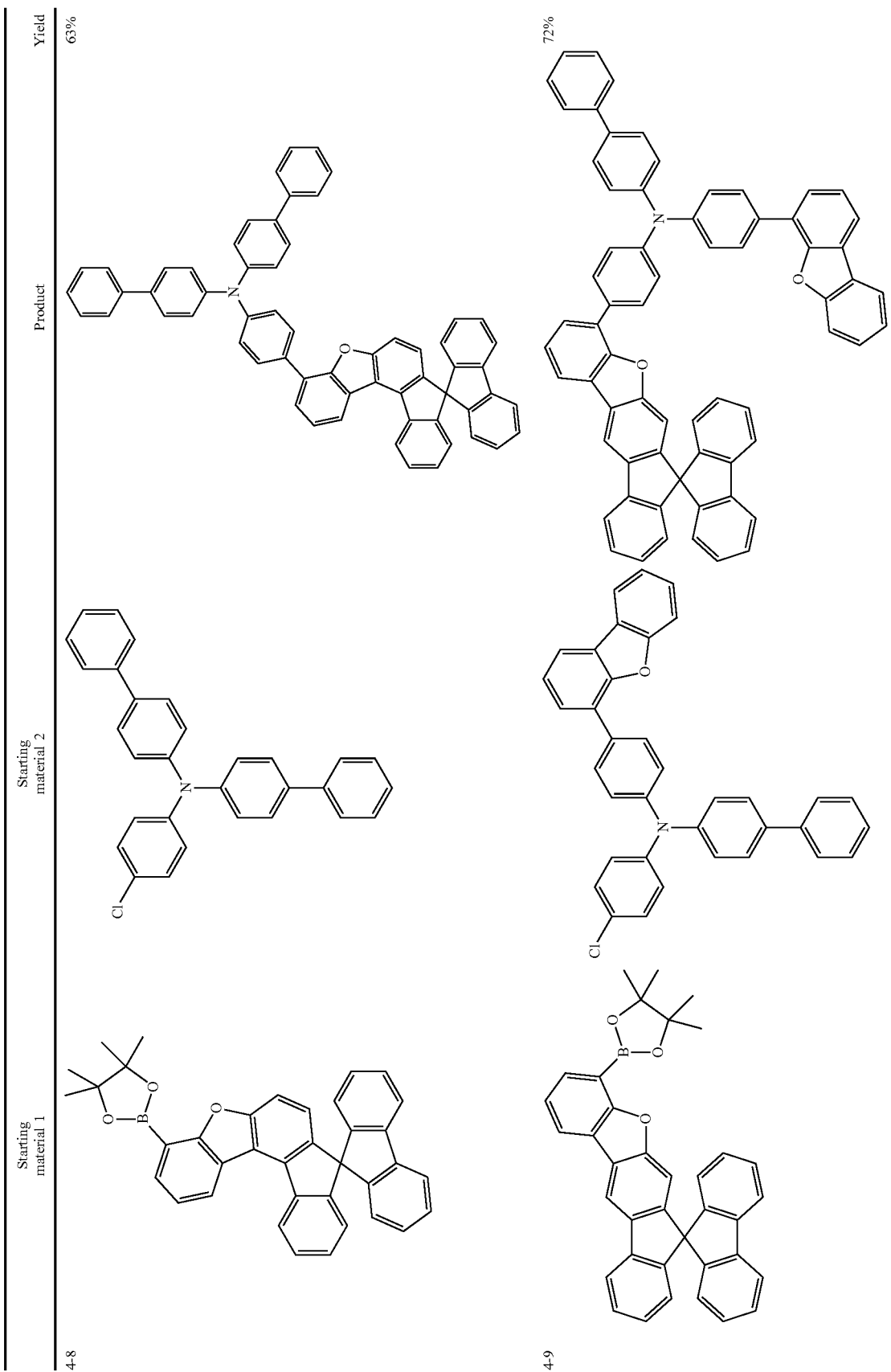

-continued
| | Starting material 1 | Starting material 2 | Product | Yield |
|---|---|---|---|---|
| 4-10 | 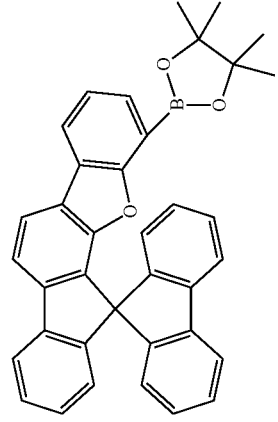 | 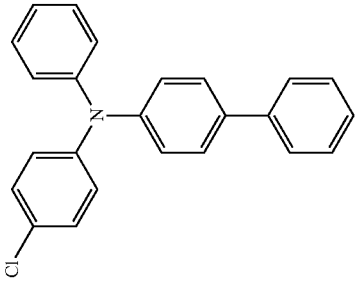 | 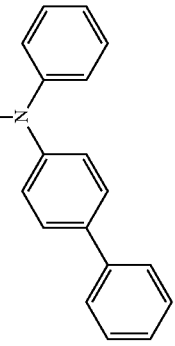 | 57% |
| Int-41a | 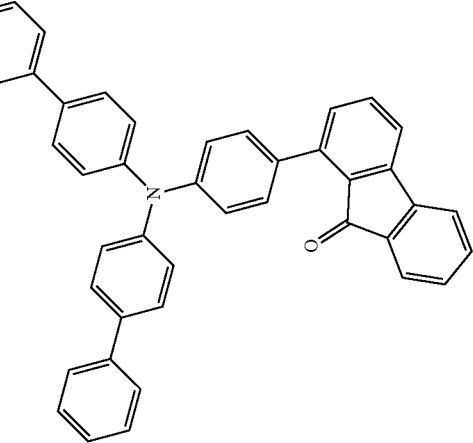 | | | 75% |

-continued

| Starting material 1 | Starting material 2 | Product | Yield |
|---|---|---|---|
| Int-41b | | | 80% |
| Int-41c | | | 82% |

| Starting material 1 | Starting material 2 | Product | Yield |
|---|---|---|---|
| 4-11 | | | 50% |

A-5) Synthesis of Compounds 5-1 to 5-8

Synthesis of Intermediates Int-42 to Int-47

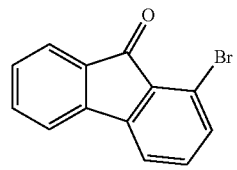

+

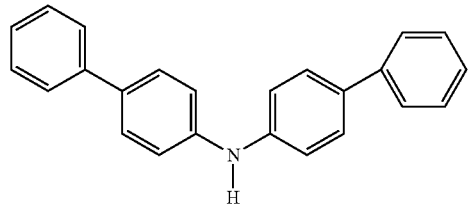

→

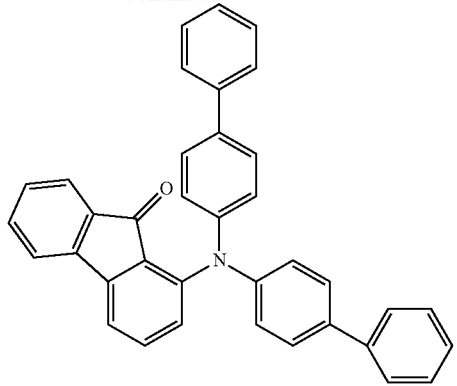

Int-42

27 g (85 mmol) of bisbiphenylamine and 22.0 g (85 mmol) of 1-bromo-fluorenone are dissolved in 170 ml of toluene. The solution is degassed and saturated with $N_2$. 4 ml (1.7 mmol) of a 10% tri-tert-butylphosphine solution and 0.2 g (0.89 mmol) of $Pd(AcO)_2$ are then added, and 12.2 g of sodium tert-butoxide (127 mmol) are subsequently added. The reaction mixture is heated at the boil under a protective atmosphere for 12 h. The mixture is subsequently partitioned between toluene and water, and the organic phase is washed three times with water and dried over $Na_2SO_4$ and evaporated in a rotary evaporator. After filtration of the crude product through silica gel with toluene, the residue which remains is recrystallised from heptane/toluene. The purity is 99% (NMR). The yield is 34 g (80% of theory).

The following compounds are prepared analogously:

| | Starting material 1 | Starting material 2 | Product | Yield |
|---|---|---|---|---|
| Int-43 | | | | 67% |
| Int-44 | | | | 75% |

| Starting material 1 | Starting material 2 | Product | Yield |
|---|---|---|---|
| Int-45 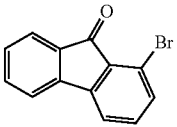 | 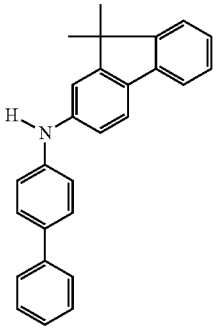 [SMILES: CC1(C)c2ccccc2-c2ccc(Nc3ccc(-c4ccccc4)cc3)cc21] | 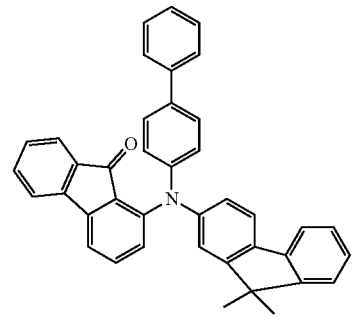 [SMILES: CC1(C)c2ccccc2-c2ccc(N(c3ccc(-c4ccccc4)cc3)c3cccc4c3C(=O)c3ccccc3-4)cc21] | 68% |
| Int-46 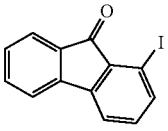 [SMILES: O=C1c2ccccc2-c2cccc(I)c21] | 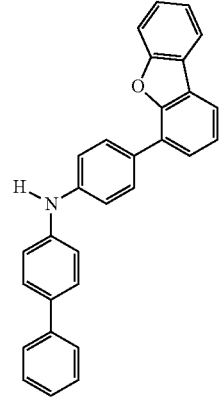 [SMILES: c1ccc(-c2ccc(Nc3ccc(-c4cccc5c4oc4ccccc45)cc3)cc2)cc1] | 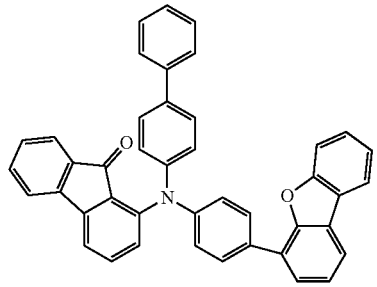 [SMILES: O=C1c2ccccc2-c2cccc(N(c3ccc(-c4ccccc4)cc3)c3ccc(-c4cccc5c4oc4ccccc45)cc3)c21] | 80% |
| Int-47 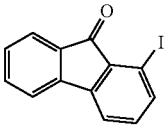 [SMILES: O=C1c2ccccc2-c2cccc(I)c21] | 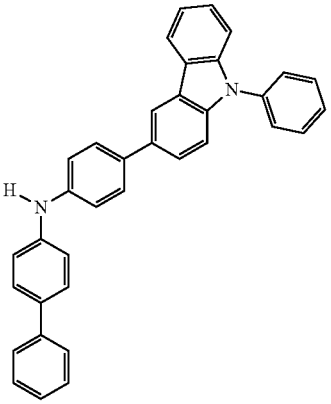 [SMILES: c1ccc(-c2ccc(Nc3ccc(-c4ccc5c(c4)c4ccccc4n5-c4ccccc4)cc3)cc2)cc1] | 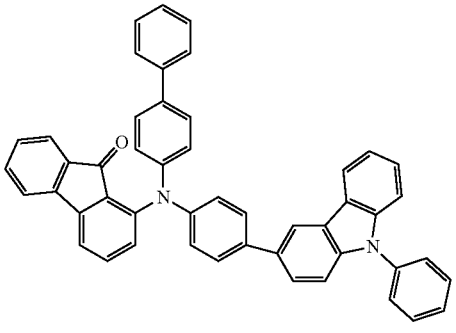 [SMILES: O=C1c2ccccc2-c2cccc(N(c3ccc(-c4ccccc4)cc3)c3ccc(-c4ccc5c(c4)c4ccccc4n5-c4ccccc4)cc3)c21] | 78% |
| Int-48 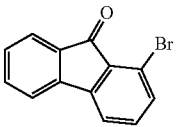 [SMILES: O=C1c2ccccc2-c2cccc(Br)c21] | 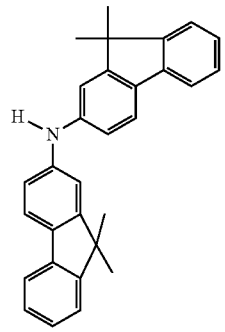 [SMILES: CC1(C)c2ccccc2-c2ccc(Nc3ccc4c(c3)C(C)(C)c3ccccc3-4)cc21] | 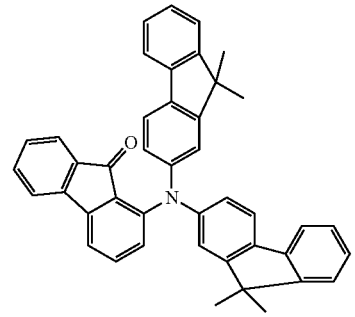 [SMILES: CC1(C)c2ccccc2-c2ccc(N(c3ccc4c(c3)C(C)(C)c3ccccc3-4)c3cccc4c3C(=O)c3ccccc3-4)cc21] | 76% |

Synthesis of Compounds 5-1 to 5-8

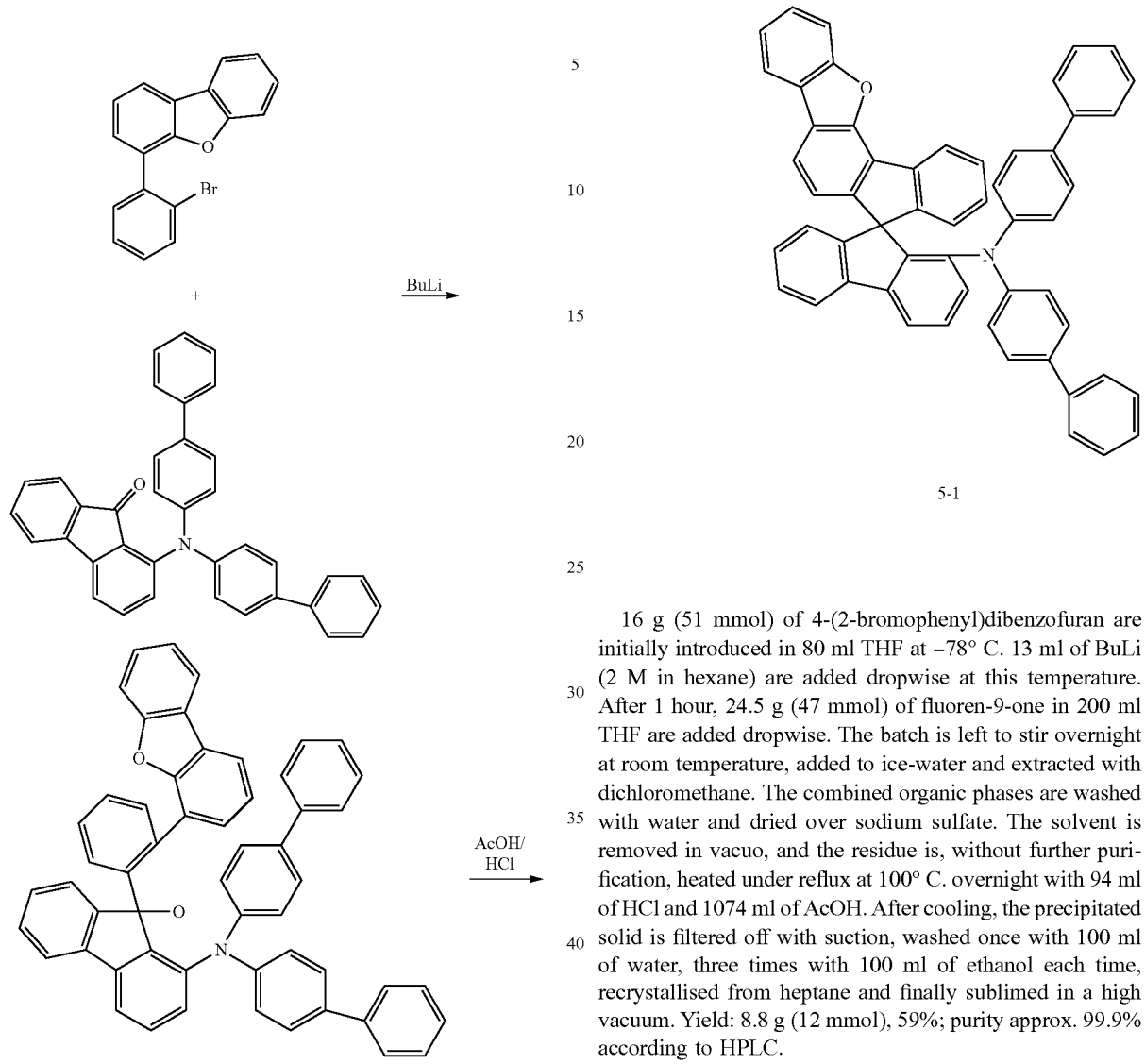

5-1

16 g (51 mmol) of 4-(2-bromophenyl)dibenzofuran are initially introduced in 80 ml THF at −78° C. 13 ml of BuLi (2 M in hexane) are added dropwise at this temperature. After 1 hour, 24.5 g (47 mmol) of fluoren-9-one in 200 ml THF are added dropwise. The batch is left to stir overnight at room temperature, added to ice-water and extracted with dichloromethane. The combined organic phases are washed with water and dried over sodium sulfate. The solvent is removed in vacuo, and the residue is, without further purification, heated under reflux at 100° C. overnight with 94 ml of HCl and 1074 ml of AcOH. After cooling, the precipitated solid is filtered off with suction, washed once with 100 ml of water, three times with 100 ml of ethanol each time, recrystallised from heptane and finally sublimed in a high vacuum. Yield: 8.8 g (12 mmol), 59%; purity approx. 99.9% according to HPLC.

The following compounds are prepared analogously:

| | Starting material 1 | Starting material 2 | Product | Yield |
|---|---|---|---|---|
| 5-2 | | | | 55% |

| Starting material 1 | Starting material 2 | Product | Yield |
|---|---|---|---|
| 5-3 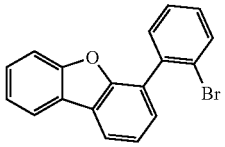 [SMILES: Brc1ccccc1-c1cccc2c1oc1ccccc12] | 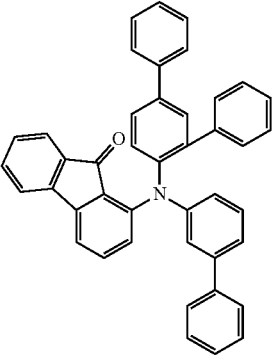 [SMILES: O=C1c2ccccc2-c2cccc(N(c3cccc(-c4ccccc4)c3)c3ccc(-c4ccccc4)cc3-c3ccccc3)c21] | 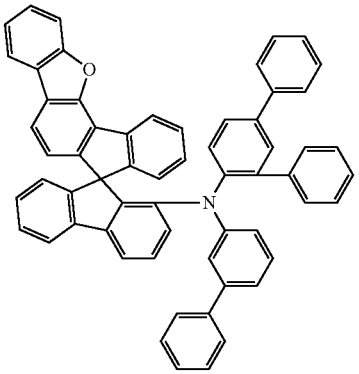 [SMILES: c1ccc(-c2cccc(N(c3ccc(-c4ccccc4)cc3-c3ccccc3)c3cccc4c3C3(c5ccccc5-4)c4ccccc4-c4c3ccc3c4oc4ccccc43)c2)cc1] | 67% |
| 5-4 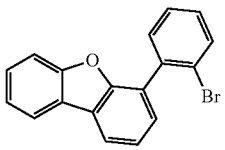 [SMILES: Brc1ccccc1-c1cccc2c1oc1ccccc12] | 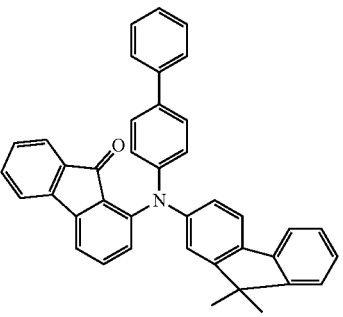 [SMILES: CC1(C)c2ccccc2-c2ccc(N(c3ccc(-c4ccccc4)cc3)c3cccc4c3C(=O)c3ccccc3-4)cc21] | 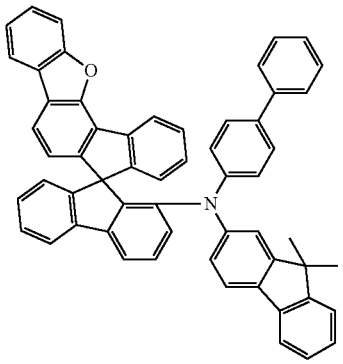 [SMILES: CC1(C)c2ccccc2-c2ccc(N(c3ccc(-c4ccccc4)cc3)c3cccc4c3C3(c5ccccc5-4)c4ccccc4-c4c3ccc3c4oc4ccccc43)cc21] | 70% |
| 5-5 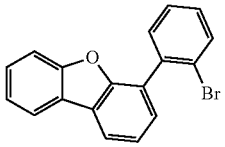 [SMILES: Brc1ccccc1-c1cccc2c1oc1ccccc12] | 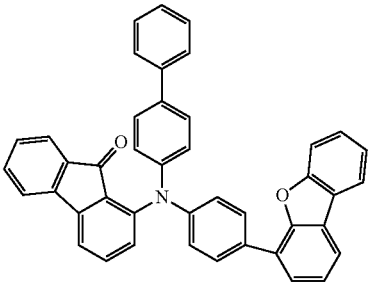 [SMILES: O=C1c2ccccc2-c2cccc(N(c3ccc(-c4ccccc4)cc3)c3ccc(-c4cccc5c4oc4ccccc45)cc3)c21] | 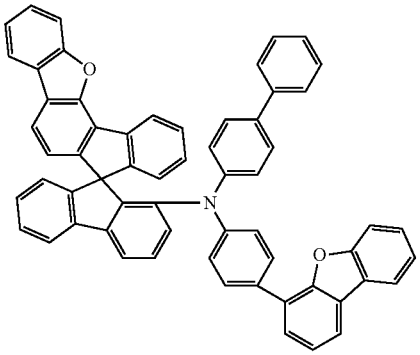 [SMILES: c1ccc(-c2ccc(N(c3ccc(-c4cccc5c4oc4ccccc45)cc3)c3cccc4c3C3(c5ccccc5-4)c4ccccc4-c4c3ccc3c4oc4ccccc43)cc2)cc1] | 49% |
| 5-6 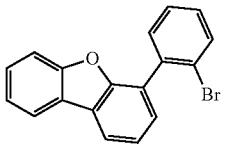 [SMILES: Brc1ccccc1-c1cccc2c1oc1ccccc12] | 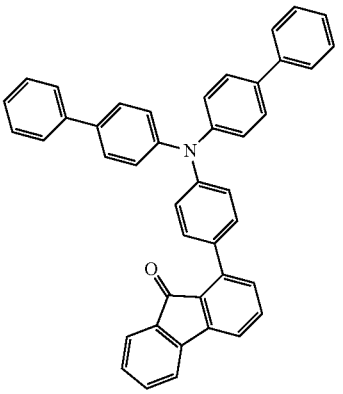 [SMILES: O=C1c2ccccc2-c2cccc(-c3ccc(N(c4ccc(-c5ccccc5)cc4)c4ccc(-c5ccccc5)cc4)cc3)c21] | 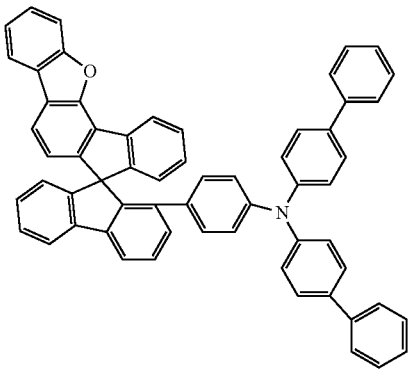 [SMILES: c1ccc(-c2ccc(N(c3ccc(-c4ccccc4)cc3)c3ccc(-c4cccc5c4C4(c6ccccc6-5)c5ccccc5-c5c4ccc4c5oc5ccccc54)cc3)cc2)cc1] | 60% |

| | Starting material 1 | Starting material 2 | Product | Yield |
|---|---|---|---|---|
| 5-7 | | | | 58% |
| 5-8 | | | | 65% |
| 5-9 | | | | 70% |

B) Device Examples

OLEDs according to the invention and OLEDs in accordance with the prior art are produced by a general process in accordance with WO 04/058911, which is adapted to the circumstances described here (for example materials).

The data of various OLEDs are presented in the following device examples E1 to E13 and E16 to E18 (inventive examples) and V1 to V4 (comparative examples). The substrates used are glass plates coated with structured ITO (indium tin oxide) in a thickness of 50 nm. The OLEDs have in principie the following layer structure: substrate/p-doped hole-transport layer (HIL1)/hole-transport layer (HTL)/p-doped hole-transport layer (HIL2)/hole-transport layer (EBL)/emission layer (EML)/electron-transport layer (ETL)/electron-injection layer (EIL) and finally a cathode. The cathode is formed by an aluminium layer with a thickness of 100 nm.

The materials required for the production of the OLEDs are shown in Table 1, the various component structures are shown in Table 2.

All materials are applied by thermal vapour deposition in a vacuum chamber. The emission layer here always consists of at least one matrix material (host material) and an emitting dopant (emitter), which is admixed with the matrix material or the matrix materials in a certain proportion by volume by co-evaporation. An expression such as H1:SEB (95%:5%) here means that material H1 is present in the layer in a proportion by volume of 95% and SEB is present in the layer in a proportion of 5%. Analogously, the electron-transport layer or the hole-injection layers may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term EQE @ 10 mA/cm$^2$ denotes the external quantum efficiency at a current density of 10 mA/cm$^2$. LT80 @ 60 mA/cm$^2$ is the lifetime by which the OLED has dropped to 80% of the initial intensity at a constant current of 60 mA/cm$^2$.

TABLE 1

Structures of the materials used

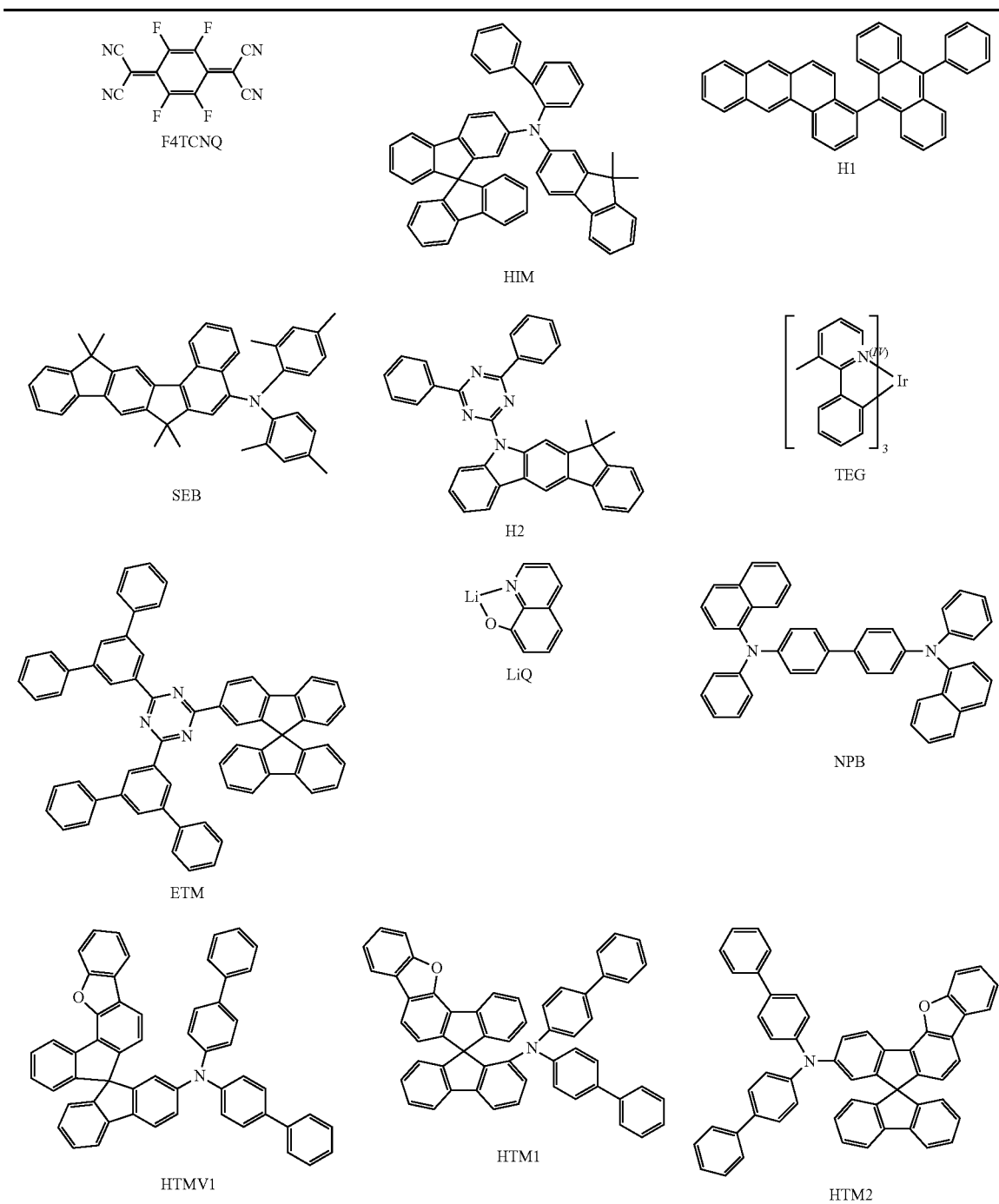

TABLE 1-continued

Structures of the materials used

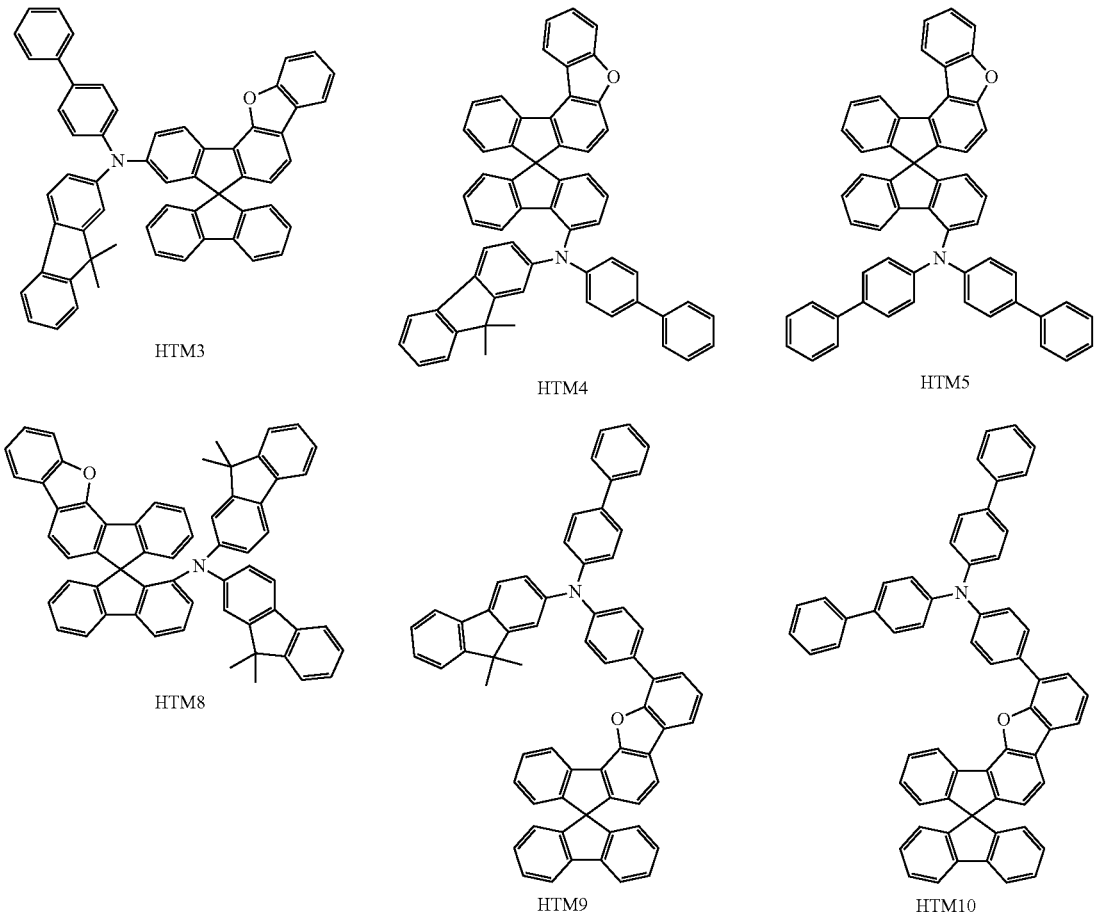

TABLE 2

Structure of the OLEDs

| Exp. | HIL1 Thickness/nm | HTL Thickness/nm | HIL2 Thickness/nm | EBL Thickness/nm | EML Thickness/nm | ETL Thickness/nm | EIL Thickness/nm |
|---|---|---|---|---|---|---|---|
| V1 | HIM:F4TCNQ(5%) 20 nm | HIM 155 nm | NPB:F4TCNQ(5%) 20 nm | NPB 20 nm | H1:SEB(5%) 20 nm | ETM:LiQ(50%) 30 nm | LiQ 1 nm |
| V2 | HIM:F4TCNQ(5%) 20 nm | HIM 155 nm | HTMV1:F4TCNQ(5%) 20 nm | HTMV1 20 nm | H1:SEB1(5%) 20 nm | ETM:LiQ(50%) 30 nm | LiQ 1 nm |
| E1 | HIM:F4TCNQ(5%) 20 nm | HIM 155 nm | HTM1:F4TCNQ(5%) 20 nm | HTM1 20 nm | H1:SEB1(5%) 20 nm | ETM:LiQ(50%) 30 nm | LiQ 1 nm |
| E2 | HIM:F4TCNQ(5%) 20 nm | HIM 155 nm | HTM2:F4TCNQ(5%) 20 nm | HTM2 20 nm | H1:SEB1(5%) 20 nm | ETM:LiQ(50%) 30 nm | LiQ 1 nm |
| E3 | HIM:F4TCNQ(5%) 20 nm | HIM 155 nm | HTM3:F4TCNQ(5%) 20 nm | HTM3 20 nm | H1:SEB1(5%) 20 nm | ETM:LiQ(50%) 30 nm | LiQ 1 nm |
| E4 | HIM:F4TCNQ(5%) 20 nm | HIM 155 nm | HTM4:F4TCNQ(5%) 20 nm | HTM4 20 nm | H1:SEB1(5%) 20 nm | ETM:LiQ(50%) 30 nm | LiQ 1 nm |
| E5 | HIM:F4TCNQ(5%) 20 nm | HIM 155 nm | HTM5:F4TCNQ(5%) 20 nm | HTM5 20 nm | H1:SEB1(5%) 20 nm | ETM:LiQ(50%) 30 nm | LiQ 1 nm |
| E6 | HIM:F4TCNQ(5%) 20 nm | HIM 155 nm | HTM8:F4TCNQ(5%) 20 nm | HTM8 20 nm | H1:SEB1(5%) 20 nm | ETM:LiQ(50%) 30 nm | LiQ 1 nm |
| E7 | HIM:F4TCNQ(5%) 20 nm | HIM 155 nm | HTM9:F4TCNQ(5%) 20 nm | HTM9 20 nm | H1:SEB1(5%) 20 nm | ETM:LiQ(50%) 30 nm | LiQ 1 nm |
| E8 | HIM:F4TCNQ(5%) 20 nm | HIM 155 nm | HTM10:F4TCNQ(5%) 20 nm | HTM10 20 nm | H1:SEB1(5%) 20 nm | ETM:LiQ(50%) 30 nm | LiQ 1 nm |
| V3 | HIM:F4TCNQ(5%) 20 nm | HIM 210 nm | NPB:F4TCNQ(5%) 20 nm | NPB 20 nm | H2:TEG(10%) 30 nm | ETM:LiQ(50%) 40 nm | LiQ 1 nm |

TABLE 2-continued

Structure of the OLEDs

| Exp. | HIL1 Thickness/nm | HTL Thickness/nm | HIL2 Thickness/nm | EBL Thickness/nm | EML Thickness/nm | ETL Thickness/nm | EIL Thickness/nm |
|---|---|---|---|---|---|---|---|
| V4 | HIM:F4TCNQ(5%) 20 nm | HIM 210 nm | HTMV1:F4TCNQ(5%) 20 nm | HTMV1 20 nm | H2:TEG(10%) 30 nm | ETM:LiQ(50%) 40 nm | LiQ 1 nm |
| E9 | HIM:F4TCNQ(5%) 20 nm | HIM 210 nm | HTM1:F4TCNQ(5%) 20 nm | HTM1 20 nm | H2:TEG(10%) 30 nm | ETM:LiQ(50%) 40 nm | LiQ 1 nm |
| E10 | HIM:F4TCNQ(5%) 20 nm | HIM 210 nm | HTM2:F4TCNQ(5%) 20 nm | HTM2 20 nm | H2:TEG(10%) 30 nm | ETM:LiQ(50%) 40 nm | LiQ 1 nm |
| E11 | HIM:F4TCNQ(5%) 20 nm | HIM 210 nm | HTM3:F4TCNQ(5%) 20 nm | HTM3 20 nm | H2:TEG(10%) 30 nm | ETM:LiQ(50%) 40 nm | LiQ 1 nm |
| E12 | HIM:F4TCNQ(5%) 20 nm | HIM 210 nm | HTM4:F4TCNQ(5%) 20 nm | HTM4 20 nm | H2:TEG(10%) 30 nm | ETM:LiQ(50%) 40 nm | LiQ 1 nm |
| E13 | HIM:F4TCNQ(5%) 20 nm | HIM 210 nm | HTM5:F4TCNQ(5%) 20 nm | HTM5 20 nm | H2:TEG(10%) 30 nm | ETM:LiQ(50%) 40 nm | LiQ 1 nm |
| E16 | HIM:F4TCNQ(5%) 20 nm | HIM 210 nm | HTM8:F4TCNQ(5%) 20 nm | HTM8 20 nm | H2:TEG(10%) 30 nm | ETM:LiQ(50%) 40 nm | LiQ 1 nm |
| E17 | HIM:F4TCNQ(5%) 20 nm | HIM 210 nm | HTM9:F4TCNQ(5%) 20 nm | HTM9 20 nm | H2:TEG(10%) 30 nm | ETM:LiQ(50%) 40 nm | LiQ 1 nm |
| E18 | HIM:F4TCNQ(5%) 20 nm | HIM 210 nm | HTM10:F4TCNQ(5%) 20 nm | HTM10 20 nm | H2:TEG(10%) 30 nm | ETM:LiQ(50%) 40 nm | LiQ 1 nm |

Compounds HTM1 to HTM5 and HTM8 to HTM10 according to the invention are very highly suitable for use as OLED materials, as shown by Examples E1 to E13 and E16 to E18 (E1 to E8: singlet components; E9 to E13 and E16 to E18: triplet components). Improved performance data of the OLEDs are obtained with the compounds compared with the reference compounds HTMV1 and NPB (Comparative Examples V1 and V2: singlet components; V3 and V4: triplet components).

In a singlet blue component, samples E2 (7.9%), E3 (8.6%), E4 (7.9%) and E5 (8.3%) according to the invention exhibit higher quantum efficiencies at 10 mA/cm$^2$ compared with reference samples V1 and V2 (6.2% and 7.7%). The lifetime LT80 at 60 mA/cm$^2$ in the case of samples E1 (356 h), E2 (312 h), E4 (403 h), E6 (275 h), E7 (316 h) and E8 (408 h) according to the invention is also significantly better than in the case of reference samples V1 (125 h) and V2 (257 h).

In a triplet green component, reference samples V3 (11.7%) and V4 (18.6%) exhibit lower or the same quantum efficiencies at 2 mA/cm$^2$ than samples E10 (18.6%), E12 (19.8%), E16 (19.6%), E17 (19.4%) and E18 (18.6%) according to the invention. The lifetimes (80%) at 20 mA/cm$^2$ of samples E9 (220 h), E0 (96 h), E11 (109 h), E12 (172 h), E13 (111 h), E16 (150 h), E17 (144 h) and E18 (160 h) according to the invention are also greater than in the case of reference samples V3 (80 h) and V4 (84 h).

The invention claimed is:
1. A compound of the formula (I)

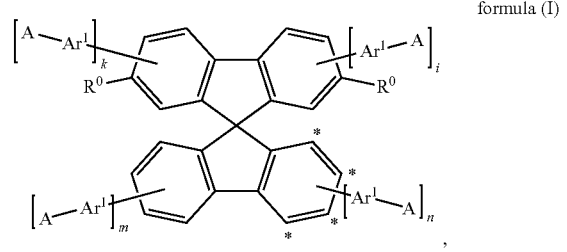

formula (I)

which contains a group of the formula (B)

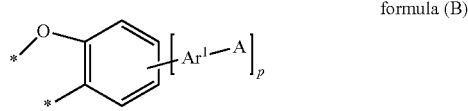

formula (B)

bonded to the basic structure of the formula (I) at two adjacent positions marked by *, where the condensation is such that a bond marked by * in formula (B) in each case links to a position marked by * on the basic structure of the formula (I);
  which is optionally substituted by a radical R$^1$ at one or more positions on the basic structure of the formula (I) and the group of the formula (B) which are depicted as unsubstituted; and
  which has the following definitions of the variables:
  A is on each occurrence, identically or differently, a group of the formula (A1), (A2) or (A3), which is bonded via the bond marked by #;

formula (A1)

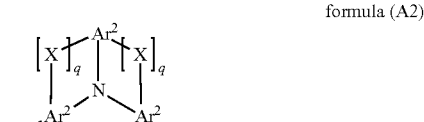

formula (A2)

formula (A3)

Ar$^1$ is on each occurrence, identically or differently, a single bond or an aromatic or heteroaromatic ring system having 6 to 30 aromatic ring atoms, which is optionally substituted by one or more radicals R$^2$;

Ar² is on each occurrence, identically or differently, an aromatic or heteroaromatic ring system having 6 to 30 aromatic ring atoms, which is optionally substituted by one or more radicals R²;

X is on each occurrence, identically or differently, a single bond or a group selected from BR², C(R²)₂, Si(R²)₂, C=O, O, S, S=O, SO₂, NR², PR² or P(=O)R²;

R⁰ is on each occurrence, identically or differently, H, D, F, CN, Si(R³)₃, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R³ and where one or more CH₂ groups in the above-mentioned groups is optionally replaced by —R³C=CR³—, —C≡C—, Si(R³)₂, C=O, C=NR³, —C(=O)O—, —C(=O)NR³—, NR³, P(=O)(R³), —O—, —S—, SO or SO₂;

R¹, R² are on each occurrence, identically or differently, H, D, F, C(=O)R³, CN, Si(R³)₃, N(Ar³)₂, N(R³)₂, P(=O)(R³)₂, OR³, S(=O)R³, S(=O)₂R³, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R³ and where one or more CH₂ groups in the above-mentioned groups is optionally replaced by —R³C=CR³—, —C≡C—, Si(R³)₂, C=O, C=NR³, —C(=O)O—, —C(=O)NR³—, NR³, P(=O)(R³), —O—, —S—, SO or SO₂, or an aromatic or heteroaromatic ring system having 5 to 30 aromatic ring atoms, which is optionally substituted by one or more radicals R³; two or more radicals R¹ or R² is optionally linked to one another and may form a ring;

Ar³ is on each occurrence, identically or differently, an aromatic or heteroaromatic ring system having 5 to 30 aromatic ring atoms, which is optionally substituted by one or more radicals R³;

R³ is on each occurrence, identically or differently, H, D, F, C(=O)R⁴, CN, Si(R⁴)₃, N(Ar³)₂, N(R⁴)₂, P(=O)(R⁴)₂, OR⁴, S(=O)R⁴, S(=O)₂R⁴, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R⁴ and where one or more CH₂ groups in the above-mentioned groups is optionally replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂, or an aromatic or heteroaromatic ring system having 5 to 30 aromatic ring atoms, which is optionally substituted by one or more radicals R⁴; two or more radicals R³ is optionally linked to one another and may form a ring;

R⁴ is on each occurrence, identically or differently, H, D, F, CN or an aliphatic, aromatic or heteroaromatic organic radical having 1 to 20 C atoms, in which, in addition, one or more H atoms is optionally replaced by D, F or CN; two or more substituents R⁴ is optionally linked to one another and may form a ring;

q is on each occurrence, identically or differently, 0 or 1, where at least one q in formula (A2) is equal to 1;

i, k, m, n and p are on each occurrence, identically or differently, 0 or 1, wherein the sum of the indices p and m is equal to 1.

2. The compound according to claim 1, wherein A is a group of the formula (A-1).

3. The compound according to claim 1, wherein X is selected on each occurrence, identically or differently, from a single bond or C(R²)₂, C=O, O, S or NR².

4. The compound according to claim 1, wherein X is a single bond.

5. The compound according to claim 1, wherein R⁰ is on each occurrence, identically or differently, H, D, F, a straight-chain alkyl or alkoxy group having 1 to 10 C atoms or a branched or cyclic alkyl or alkoxy group having 3 to 10 C atoms, where the above-mentioned groups may each be substituted by one or more radicals R³.

6. The compound according to claim 1, wherein R¹ and R² are on each occurrence, identically or differently, H, D, F, CN, a straight-chain alkyl group having 1 to 10 C atoms or a branched or cyclic alkyl group having 3 to 10 C atoms, where the above-mentioned groups may each be substituted by one or more radicals R³, or an aromatic or heteroaromatic ring system having 6 to 25 aromatic ring atoms, which may in each case be substituted by one or more radicals R³.

7. The compound according to claim 1, wherein p is equal to 1.

8. The compound according to claim 1, wherein k is equal to 1.

9. The compound according to claim 1, wherein the sum of the indices i, k, m, n and p is equal to 1 or 2.

10. A compound of one of the formulae (II-1) to (II-6)

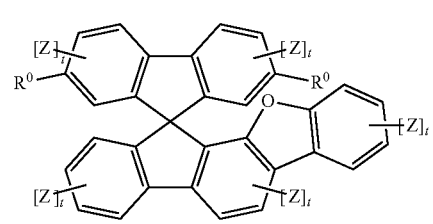

formula (II-1)

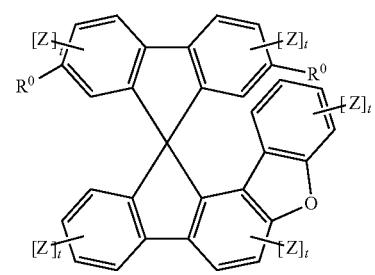

formula (II-2)

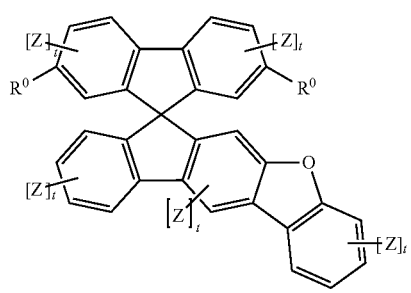

formula (II-3)

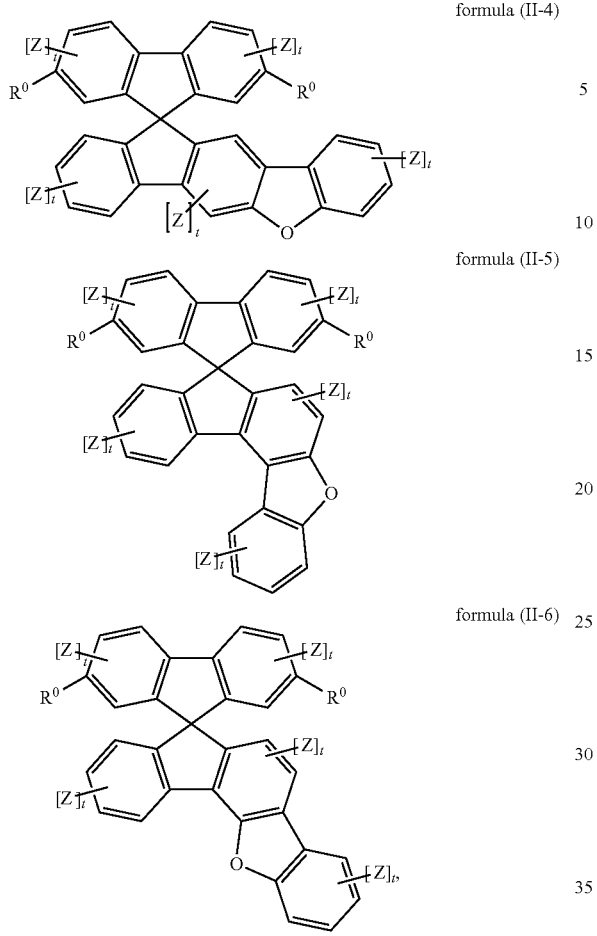

formula (II-4)

formula (II-5)

formula (II-6)

each of which is optionally substituted at one or more free positions by a radical $R^1$, wherein $R^1$ are on each occurrence, identically or differently, H, D, F, $C(=O)R^3$, CN, $Si(R^3)_3$, $N(Ar^3)_2$, $N(R^3)_2$, $P(=O)(R^3)_2$, $OR^3$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by $-R^3C=CR^3-$, $-C\equiv C-$, $Si(R^3)_2$, $C=O$, $C=NR^3$, $-C(=O)O-$, $-C(=O)NR^3-$, $NR^3$, $P(=O)(R^3)$, $-O-$, $-S-$, SO or $SO_2$, or an aromatic or heteroaromatic ring system having 5 to 30 aromatic ring atoms, which is optionally substituted by one or more radicals $R^3$; two or more radicals $R^1$ or $R^2$ is optionally linked to one another and may form a ring;

$Ar^3$ is on each occurrence, identically or differently, an aromatic or heteroaromatic ring system having 5 to 30 aromatic ring atoms, which is optionally substituted by one or more radicals $R^3$;

$R^0$ is on each occurrence, identically or differently, H, D, F, CN, $Si(R^3)_3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by $-R^3C=CR^3-$, $-C\equiv C-$, $Si(R^3)_2$, $C=O$, $C=NR^3$, $-C(=O)O-$, $-C(=O)NR^3-$, $NR^3$, $P(=O)(R^3)$, $-O-$, $-S-$, SO or $SO_2$;

$R^3$ is on each occurrence, identically or differently, H, D, F, $C(=O)R^4$, CN, $Si(R^4)_3$, $N(Ar^3)_2$, $N(R^4)_2$, $P(=O)(R^4)_2$, $OR^4$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups is optionally replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$, or an aromatic or heteroaromatic ring system having 5 to 30 aromatic ring atoms, which is optionally substituted by one or more radicals $R^4$; two or more radicals $R^3$ is optionally linked to one another and may form a ring;

$R^4$ is on each occurrence, identically or differently, H, D, F, CN or an aliphatic, aromatic or heteroaromatic organic radical having 1 to 20 C atoms, in which, in addition, one or more H atoms is optionally replaced by D, F or CN; two or more substituents $R^4$ is optionally linked to one another and may form a ring;

Z is selected on each occurrence, identically or differently, from F, Cl, Br, I, $B(OR^3)_2$, $OSO_2R^3$, $S(=O)R^3$ and $S(=O)_2R^3$;

t is on each occurrence, identically or differently, 0 or 1, where at least one index t per formula is equal to 1.

11. A process for the preparation of the compound according to claim 1, which comprises preparing firstly the spirobifluorene basic structure, and, in a later step, an arylamino or carbazole group or an aryl or heteroaryl group which is substituted by an arylamino or carbazole group is introduced via an organometallic coupling reaction.

12. An oligomer, polymer or dendrimer containing one or more compounds according to claim 1, where the bond(s) to the polymer, oligomer or dendrimers is optionally localised at any desired positions in formula (I) that are substituted by $R^0$, $R^1$ or $R^2$.

13. A formulation comprising at least one compound according to claim 1 and at least one solvent.

14. An electronic device comprising at least one compound according to claim 1.

15. The electronic device according to claim 14, wherein the device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes and organic electroluminescent devices.

16. An organic electroluminescent device wherein the compound according to claim 1 is present as hole-transport material or as matrix material of the emitting layer.

17. The compound as claimed in claim 10, wherein $R^0$ is on each occurrence, identically or differently, H, D, CN, $Si(R^3)_3$, a straight-chain alkyl or alkoxy group having 1 to 20 C atoms or a branched or cyclic alkyl or alkory group having 3 to 20 C atoms or an alkenyl or alkynyl group having 2 to 20 atoms, where the above-mentioned groups may each be substituted by one or more radicals $R^3$ and where one or more $CH_2$ groups in the above mentioned groups is optionally replaced by —R$^3$C=CR$^3$—, —C≡C—, Si(R$^3$)$_2$, C=O, C=NR$^3$, —C(=O)O—, —C(=O)NR$^3$, NR$^3$, P(=O)(R$^3$), —O—, —S—, SO or SO$_2$.

* * * * *